United States Patent [19]
Nagata et al.

[11] Patent Number: 5,719,152
[45] Date of Patent: Feb. 17, 1998

[54] TRICYCLIC QUINOXALINEDIONE DERIVATIVES

[75] Inventors: Ryu Nagata, Kyoto; Norihiko Tanno, Ibaraki; Toru Kodo; Hiroshi Yamaguchi, both of Osaka; Nobuyuki Ae, Toyonaka, all of Japan

[73] Assignee: Sumitomo Pharmaceuticals Co., Ltd., Osaka-fu, Japan

[21] Appl. No.: 611,973

[22] Filed: Mar. 6, 1996

Related U.S. Application Data

[63] Continuation of Ser. No. 231,468, Apr. 22, 1994, abandoned.

[30] Foreign Application Priority Data

Apr. 22, 1993 [JP] Japan ................................ 5-120725

[51] Int. Cl.$^6$ .................. A61K 31/495; C07D 487/06; C07D 471/06; C07D 215/48
[52] U.S. Cl. .......................... 514/250; 544/250; 562/426; 562/439; 562/451
[58] Field of Search .................. 544/344; 514/250

[56] References Cited

U.S. PATENT DOCUMENTS

| | | | |
|---|---|---|---|
| 3,813,392 | 5/1974 | Sellstedt et al. | 260/250 R |
| 4,075,206 | 2/1978 | Holmes | 260/250 Q |
| 5,616,586 | 4/1997 | Nagata | 544/344 |

FOREIGN PATENT DOCUMENTS 90 15058  12/1990  WIPO.

OTHER PUBLICATIONS

Frontiers in Excitatory Amino Acid Research, pp. 203–210 (1988).
Brain's Diseases of the Nervous System, seventh edition, Oxford University Press, pp. 926–927 (1969).
Annual Reports in Medicinal Chemistry–21, Academic Press, Inc., Chapter 27, Bioisosterism in Drug Design, pp. 283–291 (1986).
Annual Reports in Medicinal Chemistry–10, Academic Press, Inc., Chapter 31, Prodrug Approach in Drug Design, pp. 306–316 (1975).
The New England Journal of Medicine, 330, 613–622, 1994.
The Journal of Pharmacology and Experimental Therapeutics, 264, 1248–1252, 1993.
Stroke, 25, 255, 1994.
Journal of Cerebral Blood Flow and Metabolism, 11, 786–793, 1991.
Eckard Webber, Antagonist at the Glycine Coagonist Site of the NMDA Receptor—In Vivo Efficacy Profiles in Animal Models of Stroke, Cambridge Healthtech Institute, Waltham, MA (1994).
Richardson et al. (1959) *J. Org. Chem.* 25:1138–47.
Pellegrini–Giampietro et al. (1989) *Br. J. Pharmacol* 98:1281–86.
Sheardown et al. (1989) *Eur. J. of Pharmacology* 174:197–204.
Yoneda et al. (1989) *Biochem. and Biophys. Research Comm.* 164(2):841–49.
Sheardown et al. (1990) *Science* 247:571–74.
Isoda et al. (1980) *Chem. Pharm. Bull.* 28(8):2337–46.
Journal of Cerebral Blood Flow and Metabolism, 11, (Suppl. 2), S304, 1992.
Pain, 51, No. 2, 249–253, 1992.
Br. J. Clin. Pharmac., 34, 106–114, 1992.
The Journal of Pharmacology and Experimental Therapeutics, 264, 256–264, 1993.
A. Richardson (1965) *Journal of Organic Chemistry* 30(8):2589–93.
D. J. McNamara et al., J. Med. Chem. vol. 33, No. 7, 1990, pp. 2045–2051.

*Primary Examiner*—Mark L. Berch
*Attorney, Agent, or Firm*—Birch, Stewart, Kolasch & Birch, LLP

[57] ABSTRACT

A tricyclic quinoxalinedione derivative represented by the formula 1:

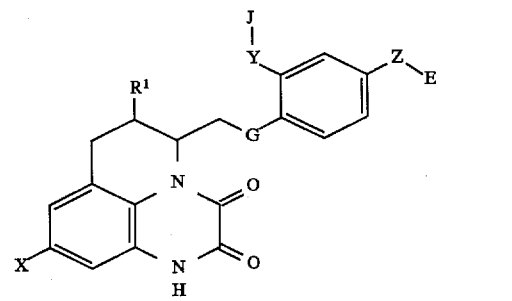

wherein X represents hydrogen, alkyl, halogen, cyano, trifluoromethyl, or nitro;

$R^1$ represents hydrogen, alkyl, cycloalkyl, or cycloalkylalkyl;

G represents —$CONR^2$— or —$NR^2CO$—, wherein $R^2$ represents hydrogen or alkyl;

J represents an acidic group or a group which is convertible thereto in vivo;

E represents an basic group or a group which is convertible thereto in vivo;

Y represents a single bond, alkylene, alkenylene, substituted alkylene, or $Y^1$—Q—$Y^2$, wherein $Y^1$ represents a single bond or alkylene, $Y^2$ represents alkylene, and Q represents a heteroatom selected from oxygen or sulfur;

Z represents alkylene, or a pharmaceutically acceptable salt thereof, these compounds are selective antagonists of glycine binding site of the NMDA receptor.

16 Claims, No Drawings

TRICYCLIC QUINOXALINEDIONE DERIVATIVES

This application is a continuation of application Ser. No. 08/231,468 filed on Apr. 22, 1994, now abandoned.

This invention relates to a new class of tricyclic quinoxalinedione derivatives which are selective antagonists of glycine binding site of the NMDA (N-methyl-D-aspartate) receptor. Particularly, the compounds provided by the present invention show in vivo antagonism against the excitation of the NMDA receptors under systemic administrations and therefore, are especially useful for minimizing damage of central nervous system induced by ischemic or hypoxic conditions such as stroke, hypoglycemia, cardiac arrest, and physical trauma, (see, J. McCulloch, Br. J. clin. Pharmacol., 34, 106 (1992)). The compounds are also useful in treatment of a number of neurodegenerative disorders including epilepsy, Huntington's chorea, Parkinson's disease, and Alzheimer's disease (reviews: G. Johnson, Annu. Rep. Med. Chem., 24, 41 (1989) and G. Johson and C. F. Bigge, ibid., 26, 11, (1991)). The present compounds may also have analgesic, antidepressant, anxiolytic, and anti-schizophrenic activities, by virtue of these NMDA-glycine antagonism, as indicated by recent reports, e.g. A. H. Dickenson and E. Aydar, Neuroscience Lett., 121, 263 (1991), R. Trullas and P. Skolnick, Eur. J. Pharmacol., 185, 1 (1990), J. H. Kehne, et al., Eur. J. Pharmacol., 193, 283 (1991), P. H. Hutson, et al., Br. J. Pharmacol., 103, 2037 (1991), in which the reagents affecting glycine—binding site of NMDA receptors have shown such activities. Excessive release of glutamic acid and/or glycine from neuronal and glial cells results in overexcitation of NMDA receptor-$Ca^{2+}$ channel complexes and successive massive amount of $Ca^{2+}$ influx into the cell, which leads to neuronal cell death. NMDA-glycine antagonist described in the present invention would obviously regulate the amount of $Ca^{2+}$ influx from the glycine modulatory site of NMDA receptor-channel complex to maintain normal activities of neuronal cell. Therefore, the compounds of the present invention may be potential therapeutic agents for any diseases of animals including human caused by excessive glutamic acid and/or glycine release in addition to the diseases indicated above.

Tricyclic quinoxalinediones, 6,7-dihydro-1H, 5H-pyrido [1,2,3,-de]-quinoxaline- 2,3-diones and 5,6-dihydro-1H-pyrrolo[1,2,3-de]quinoxaline-2,3-diones are disclosed in WO 93/08188, published after the priority date of this application, as selective antagonists of glutamate receptors such as NMDA receptors and AMPA (2-amino-3-hydroxy-5-methyl-4-isoxazole-propionic acid) receptors. The compounds of the present invention, however, exhibit much higher in vivo activities under systemic administrations compared to the compounds of examples in WO 93/08188.

The present invention provides novel tricyclic quinoxalinedione derivatives depicted by formula 1 and pharmaceutically acceptable salts thereof:

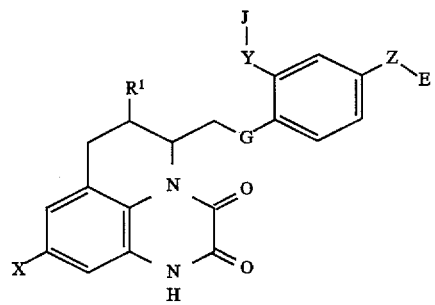

wherein X represents hydrogen, alkyl, halogen, cyano, trifluoromethyl, or nitro;

$R^1$ represents hydrogen, alkyl, cycloalkyl, or cycloalkylalkyl;

G represents —$CONR^2$— or —$NR^2CO$—, wherein $R^2$ represents hydrogen or alkyl;

J represents an acidic group or a group which is convertible thereto in vivo;

E represents an basic group or a group which is convertible thereto in vivo;

Y represents a single bond, alkylene, alkenylene, substituted alkylene, or $Y^1$—Q—$Y^2$, wherein $Y^1$ represents a single bond or alkylene, $Y^2$ represents alkylene, and Q represents a heteroatom selected from oxygen or sulfur;

Z represents alkylene.

The compounds of the present invention possess both the groups represented by J and E simultaneously in the same molecule and provide much higher in vivo activities compared to the compounds which possess one of the groups represented by J and E in the molecule.

This invention further relates to aniline derivatives depicted by formula 6, which are useful intermediates for preparation of compounds 1:

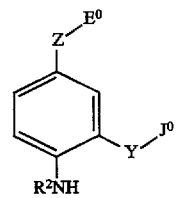

wherein $R^2$, Y and Z are as defined above;

$J^0$ represents a protected carboxyl group;

$E^0$ represents —$NHL^1$ or —$NHC(=NL^1)NHL^1$, wherein $L^1$ represents a protecting group for amino or guanidino function.

The term "protected carboxyl group" includes —$CO_2R^6$, wherein $R^6$ represents alkyl, substituted alkyl, cycloalkyl, cycloalkylalkyl, arylalkyl, substituted arylalkyl, or alkenyl. A preferable example is —$CO_2Me$.

The term "protecting group for amino or guanidino function" as used herein includes —$CO_2R^0$, wherein $R^0$ represents alkyl, cycloalkyl, cycloalkylalkyl, aryl, substituted aryl, arylalkyl, substituted arylalkyl, or alkenyl. A preferable example is t-butoxycarbonyl.

The term "arylalkyl" as used herein includes straight-chained or branched alkyl groups attached with aryl group, which contains up to 15 carbon atoms. Typical examples are benzyl, phenylethyl, 1- or 2-naphthylmethyl, and 1- or 2-naphthylpropyl.

The term "aryl" as used herein includes aryl groups containing up to 10 carbon atoms. Typical examples are phenyl, and naphthyl.

The number of the substituents of substituted aryl or substituted arylalkyl as used herein may be permitted to be up to 3, and the substituents include alkyl, halogen, trifluoromethyl, and alkoxy.

The number of the substituents of substituted alkyl as used herein may be permitted to be up to 3, and the substituents include alkoxy, halogen and trimethylsilyl.

The term "alkyl" as used herein includes straight-chained or branched alkyl groups containing from 1 to 6 carbon atoms. Typical examples are methyl, ethyl, n-propyl, isopropyl, sec-butyl, tert-butyl, neopentyl, n-pentyl, and n-hexyl.

The term "halogen" as used herein includes fluorine, chlorine, bromine, and iodine. Typical examples are chlorine and bromine.

The term "alkoxy" as used herein includes straight-chained or branched alkoxy groups containing from 1 to 6 carbon atoms. Typical examples are methoxy, ethoxy, propoxy, isopropoxy, sec-butoxy, tert-butoxy, neopentoxy, pentoxy, and hexoxy.

The term "cycloalkyl" as used herein includes cycloalkyl groups containing from 3 to 7 carbon atoms. Typical examples are cyclopropyl, cyclobutyl, cyclopentyl, cyclohexyl, and cycloheptyl.

The term "cycloalkylalkyl" as used herein includes a straight-chain or branched-chain alkyl to which a cycloalkyl group is attached, which contains up to 13 carbon atoms. Typical examples are cyclopropylmethyl, 2-cyclopentylethyl, cyclohexylmethyl, and 3-cyclohexylpropyl.

The term "basic group" as used herein means the group which is readily protonated in vivo to provide cation. Typical examples are $-NH_2$, $-NHR^{3E}$, $-NR^{3E}R^{4E}$, $-NH-C(=NH)-NH_2$, $-NH-C(=NH)-NHR^{3E}$, and $-NH-C(=NH)-NR^{3E}R^{4E}$. Herein, $R^{3E}$ and $R^{4E}$ independently represent alkyl, cycloalkyl, alkenyl, or cycloalkylalkyl, or $R^{3E}$ and $R^{4E}$ are joined to form a cyclic amine.

The term "alkenyl" as used herein includes straight-chained or branched alkenyl groups containing from 3 to 6 carbon atoms, of which an olefinic carbon atom may not be connected directly with nitrogen atom or oxygen atom. Typical examples are allyl, 2-butenyl, and 3-butenyl.

The term "group which is convertible to a basic group in vivo" as used herein includes $-NHL$, $-NLR^{3E}$, $-NH-C(=NL)-NH_2$, $-NH-C(=NL)-NHR^{3E}$, and $-NH-C(=NL)-NR^{3E}R^{4E}$. Herein, L means a hydrolyzable group in vivo, such as alkanoyl group or alkoxycarbonyl group.

The term "alkanoyl" as used herein includes straight-chained or branched alkanoyl groups containing from 1 to 6 carbon atoms. Typical examples are formyl, acetyl, propanoyl, n-butanoyl, and pivaloyl.

The term "alkoxycarbonyl" as used herein includes straight-chained or branched alkoxycarbonyl groups containing from 2 to 6 carbon atoms. Typical examples are methoxycarbonyl, ethoxycarbonyl, propoxycarbonyl, isopropoxycarbonyl, sec-butoxycarbonyl, and tert-butoxycarbonyl.

The term "acidic group" as used herein means the group which is readily deprotonated in vivo to provide anion. Typical examples are carboxyl and tetrazolyl.

The term "group which is convertible to an acidic group in vivo" as used herein means the group which generates the acidic group in vivo by hydrolysis. Typical examples are $-COOR^{3J}$, $-CONH_2$, $-CON(OH)H$, $-CONHR^{3J}$, $-CON(OH)R^{3J}$, $-CON(OR^{5J})R^{3J}$, or $-CONR^{3J}R^{4J}$, wherein $R^{3J}$ and $R^{4J}$ independently represent alkyl, cycloalkyl, alkenyl, arylalkyl, substituted arylalkyl, or cycloalkylalkyl, or $R^{3J}$ and $R^{4J}$ are joined to form a cyclic amine, and $R^{5J}$ represents alkyl.

The term "cyclic amine" which $R^{3E}$ and $R^{4E}$, or $R^{3J}$ and $R^{4J}$ are joined to form includes 3 to 7 membered cyclic amine such as azetidine, pyrrolidine, or piperidine, and 5 to 7 membered cyclic amine that contains an additional heteroatom, which is an oxygen or nitrogen atom, wherein the additional oxygen or nitrogen atom is always bonded to an adjacent alkylene group, such as piperazine, N-methylpiperazine, or morpholine.

The term "alkylene" as used herein includes straight-chained or branched alkylene groups containing from 1 to 6 carbon atoms. Typical examples are methylene, dimethylene, trimethylene, tetramethylene, 2-methyltrimethylene, 3-methyltrimethylene, 1,1-dimethylmethylene, pentamethylene, and hexamethylene.

The term "alkenylene" as used herein includes straight-chained or branched alkenylene groups containing from 2 to 6 carbon atoms. Typical examples are vinylene, 1-propenylene, 2-propenylene, 3-butenylene, 2-ethyl-3-butenylene, 4-pentenylene, 3-methyl-4-pentenylene, and 1-hexenylene.

The substituent of the term "substituted alkylene" includes hydroxy, $-OR^{3S}$, $-OCOR^{3S}$, amino, $-NHCOR^{3S}$, $-NHCO_2R^{3S}$, carboxyl, and $CO_2R^{3S}$, wherein $R^{3S}$ represents alkyl, cycloalkyl, alkenyl or cycloalkylalkyl. Typical examples of the "substituted alkylene" are $-CH(OH)-$, $-CH(OAc)-$, $-CH(CO_2\text{-tert-Bu})-$, and $-CH_2-CH_2-CH(CO_2Et)-$. Preferably, the substituent and J group may be attached to the same carbon atom.

Typical examples of $Y^1-Q-Y^2$ are $-O-CH_2-$, $-S-CH_2-$, $-CH_2-O-CH_2-$, $-CH_2-S-CH_2-$, and $-CH_2CH_2-O-CH(CH_3)-$.

The expression "pharmaceutically acceptable salts thereof" represents either non-toxic acid addition salts or base addition salts.

The acid which forms non-toxic salts with the compounds provided by formula 1 include inorganic acid such as hydrochloric, hydrobromic, sulfuric, and phosphoric acid or organic acid such as acetic, oxalic, citric, lactic, tartaric, malonic, fumaric, maleic acid, and methanesulfonic acid. On the other hand, the non-toxic base addition salts include inorganic metal salt such as lithium, sodium, potassium, magnesium, aluminum, and barium salt or organic quaternary ammonium salt such as ammonium, triethylammonium, tetrabutylammonium, pyridinium, pyrrolidinium, and piperidinium salts.

The compounds provided by the present invention have an asymmetric center at C-5 position. Although the enantiomixtures of the compounds regarding the C-5 position are encompassed in the scope of the present invention, the preferable configuration of the C-5 position may be "S". When the compounds according to the invention have more than two asymmetric centers, they additionally exist as diastereomers. Such diastereomeric pure compounds and diastereo-mixtures of these compounds are also encompassed within the scope of the present invention.

The tricyclic quinoxalinedione derivatives of the present invention can be formulated to conventional pharmaceutical preparations such as tablets, pills, capsules, powders, granules, suspensions, or emulsions all for oral administration, and such as sterile parenteral solutions or suppositories for parenteral or rectal administration, respectively. The solid compositions such as tablets can be routinely prepared by mixing the active ingredient with conventional pharmaceutical carrier or diluent such as lactose, sucrose or cornstarch, binder such as hydroxypropylcellulose, polyvinylpyrrolidone or hydroxypropylmethylcellulose, disintegrating agent such as sodium carboxymethylcellulose or sodium starch glycolate, lubricants such as stearic acid and magnesium stearate, or preservatives. For parenteral administration, the active compound is dissolved or suspended in a physiologically acceptable pharmaceutical carrier such as water, saline, oil or dextrose solution, which may contain auxiliary agent such as emulsifier, stabilizer, salt for influencing osmotic pressure or buffer, if desired. The dosage range can be varied widely depending on the severity of the particular disease, age, weight, and sex of the patient, and the route of administration. Typically, effective dosages are in the range of 1 to 1000 mg/day, or preferably of 10 to 500 mg/day orally for adult patients, which may be given in a single dose or in multiple doses. For parenteral administration, the dosage range of 0.1 to 500 rag/day, or more suitably of 3 to 100 mg/day/patient can be employed with a single dose or with multiple doses.

Examples of compounds within the scope of the invention include:

(S)-9-chloro-5-[p-tert-butoxycarbonylaminomethyl-o-(methoxycarbonyl)phenylcarbamoylmethyl]-6,7-dihydro-1H, 5H-pyrido[1,2,3-de]quinoxaline-2,3-dione;

(S)-9-chloro-5-(p-tert-butoxycarbonylaminomethyl-o-carboxyphenylcarbamoylmethyl)-6,7-dihydro-1H, 5H-pyrido[1,2,3-de]quinoxaline-2,3-dione;

(S)-9-chloro-5-(p-aminomethyl-o-carboxyphenylcarbamoylmethyl)-6,7-dihydro-1H, 5H-pyrido[1,2,3-de]quinoxaline-2,3-dione hydrochloride;

(S)-9-bromo-5-[p-tert-butoxycarbonylaminomethyl-o-(methoxycarbonyl)phenylcarbamoylmethyl]-6,7-dihydro-1H, 5H-pyrido[1,2,3-de]quinoxaline-2,3-dione;

(S)-9-bromo-5-(p-tert-butoxycarbonylaminomethyl-o-carboxyphenylcarbamoylmethyl)-6,7-dihydro-1H, 5H-pyrido[1,2,3-de]quinoxaline-2,3-dione;

(S)-9-bromo-5-(p-aminomethyl-o-carboxyphenylcarbamoylmethyl)-6,7-dihydro-1H, 5H-pyrido[1,2,3-de]quinoxaline-2,3-dione hydrochloride;

(±)-9-bromo-5-[p-tert-butoxycarbonylaminomethyl-o-(methoxycarbonyl)phenylcarbamoylmethyl]-6,7-dihydro-1H, 5H-pyrido[1,2,3-de]quinoxaline-2,3-dione;

(±)-9-bromo-5-[p-aminomethyl-o-(methoxycarbonyl)phenylcarbamoylmethyl]-6,7-dihydro-1H, 5H-pyrido[1,2,3-de]quinoxaline-2,3-dione;

(S)-9-chloro-5-[p-tert-butoxycarbonylaminomethyl-o-(methoxycarbonylmethyl)phenylcarbamoylmethyl]-6,7-dihydro-1H, 5H-pyrido[1,2,3-de]quinoxaline-2,3-dione;

(S)-9-chloro-5-[p-tert-butoxycarbonylaminomethyl-o-(carboxymethyl)phenylcarbamoylmethyl]-6,7-dihydro-1H, 5H-pyrido[1,2,3-de]quinoxaline-2,3-dione;

(S)-9-chloro-5-[p-aminomethyl-o-(carboxymethyl)phenylcarbamoylmethyl]-6,7-dihydro-1H, 5H-pyrido[1,2,3-de]quinoxaline-2,3-dione hydrochloride;

(S)-9-bromo-5-[p-tert-butoxycarbonylaminomethyl-o-(methoxycarbonylmethyl)phenylcarbamoylmethyl]-6,7-dihydro-1H, 5H-pyrido[1,2,3-de]quinoxaline-2,3-dione;

(S)-9-bromo-5-[p-tert-butoxycarbonylaminomethyl-o-(carboxymethyl)phenylcarbamoylmethyl]-6,7-dihydro-1H, 5H-pyrido[1,2,3-de]quinoxaline-2,3-dione;

(S)-9-bromo-5-[p-aminomethyl-o-(carboxymethyl)phenylcarbamoylmethyl]-6,7-dihydro-1H, 5H-pyrido[1,2,3-de]quinoxaline-2,3-dione hydrochloride (±)-9-bromo-5-[p-(2,3-di-tert-butoxycarbonylguanidinomethyl)-o-(methoxycarbonylmethyl)phenylcarbamoylmethyl]-6,7-dihydro-1H, 5H-pyrido[1,2,3-de]quinoxaline-2,3-dione;

(±)-9-bromo-5-[p-(2,3-di-tert-butoxycarbonylguanidinomethyl)-o-(carboxymethyl)phenylcarbamoylmethyl]-6,7-dihydro-1H, 5H-pyrido[1,2,3-de]quinoxaline-2,3-dione;

(±)-9-bromo-5-[p-guanidinomethyl-o-(carboxymethyl)phenylcarbamoylmethyl]-6,7-dihydro-1H, 5H-pyrido[1,2,3-de]quinoxaline-2,3-dione;

(S)-9-chloro-5-[p-tert-butoxycarbonylaminomethyl-o-(2-methoxycarbonylethyl)phenylcarbamoylmethyl]-6,7-dihydro-1H, 5H-pyrido[1,2,3-de]quinoxaline-2,3-dione;

(S)-9-chloro-5-[p-tert-butoxycarbonylaminomethyl-o-(2-carboxyethyl)phenylcarbamoylmethyl]-6,7-dihydro-1H, 5H-pyrido[1,2,3-de]quinoxaline-2,3-dione;

(S)-9-chloro-5-[p-aminomethyl-o-(2-carboxyethyl)phenylcarbamoylmethyl]-6,7-dihydro-1H, 5H-pyrido[1,2,3-de]quinoxaline-2,3-dione hydrochloride (S)-9-bromo-5-[p-tert-butoxycarbonylaminomethyl-o-(3-methoxycarbonylpropyl)phenylcarbamoylmethyl]-6,7-dihydro-1H, 5H-pyrido[1,2,3-de]quinoxaline-2,3-dione;

(S)-9-bromo-5-[p-tert-butoxycarbonylaminomethyl-o-(3-carboxypropyl)phenylcarbamoylmethyl]- 6,7-dihydro-1H, 5H-pyrido[1,2,3-de]quinoxaline-2,3-dione;

(S)-9-bromo-5-[aminomethyl-o-(3-carboxypropyl)phenylcarbamoylmethyl]-6,7-dihydro-1H, 5H-pyrido[1,2,3-de]quinoxaline-2,3-dione hydrochloride;

(5S)-9-bromo-5-[p-tert-butoxycarbonylaminomethyl-o-(1-methoxycarbonyl-1-acetoxymethyl)phenylcarbamoylmethyl]-6,7-dihydro-1H, 5H-pyrido[1,2,3-de]quinoxaline-2,3-dione;

(5S)-9-bromo-5-[p-tert-butoxycarbonylaminomethyl-o-(1-carboxy-1-hydroxymethyl)phenylcarbamoylmethyl]-6,7-dihydro-1H, 5H-pyrido[1,2,3-de]quinoxaline -2,3-dione;

(5S)-9-bromo-5-[p-aminomethyl-o-(1-carboxy-1-hydroxymethyl)phenylcarbamoylmethyl]-6,7-dihydro-1H, 5H-pyrido[1,2,3-de]quinoxaline-2,3-dione hydrochloride;

(5S)-9-chloro-5-[p-tert-butoxycarbonylaminomethyl-o-(1-methoxycarbonyl-1-acetoxymethyl)phenylcarbamoylmethyl]-6,7-dihydro-1H, 5H -pyrido[1,2,3-de]quinoxaline-2,3-dione;

(5S)-9-chloro-5-[p-tert-butoxycarbonylaminomethyl-o-(1-carboxy-1-hydroxymethyl)

phenylcarbamoylmethyl]-6,7-dihydro-1H, 5H-pyrido[1,2,3-de]quinoxaline-2,3-dione;

(5S)-9-chloro-5-[p-aminomethyl-o-(1-carboxy-1-hydroxymethyl)phenylcarbamoylmethyl]-6,7-dihydro-1H, 5H-pyrido[1,2,3-de]quinoxaline-2,3-dione hydrochloride;

(S)-9-chloro-5-[p-tert-butoxycarbonylaminomethyl-o-(tert-butoxycarbonylmethoxy)phenylcarbamoylmethyl]-6,7-dihydro-1H, 5H-pyrido[1,2,3-de]quinoxaline-2,3-dione;

(S)-9-chloro-5-[p-aminomethyl-o-(carboxymethoxy)phenylcarbamoylmethyl]-6,7-dihydro-1H, 5H-pyrido[1,2,3-de]quinoxaline-2,3-dione hydrochloride;

(S)-9-chloro-5-[p-tert-butoxycarbonylaminomethyl-o-(ethoxycarbonylmethoxy)phenylcarbamoylmethyl]-6,7-dihydro-1H, 5H-pyrido[1,2,3-de]quinoxaline-2,3-dione;

(S)-9-chloro-5-[p-aminomethyl-o-(ethoxycarbonylmethoxy)phenylcarbamoylmethyl]-6,7-dihydro-1H, 5H-pyrido[1,2,3-de]quinoxaline-2,3-dione hydrochloride;

(S)-9-bromo-5-[p-tert-butoxycarbonylaminomethyl-o-(tert-butoxycarbonylmethoxy)phenylcarbamoylmethyl]-6,7-dihydro-1H, 5H-pyrido[1,2,3-de]quinoxaline-2,3-dione;

(S)-9-bromo-5-[p-aminomethyl-o-(carboxymethoxy)phenylcarbamoylmethyl]-6,7-dihydro-1H, 5H-pyrido[1,2,3-de]quinoxaline-2,3-dione hydrochloride;

(S)-9-bromo-5-[p-tert-butoxycarbonylaminomethyl-o-(4-ethoxycarbonylbutyl)phenylcarbamoylmethyl]-6,7-dihydro-1H, 5H-pyrido[1,2,3-de]quinoxaline-2,3-dione;

(S)-9-bromo-5-[p-tert-butoxycarbonylaminomethyl-o-(4-carboxybutyl)phenylcarbamoylmethyl]-6,7-dihydro-1H, 5H-pyrido[1,2,3-de]quinoxaline-2,3-dione;

(S)-9-bromo-5-[p-aminomethyl-o-(4-carboxybutyl)phenylcarbamoylmethyl]-6,7-dihydro-1H, 5H-pyrido[1,2,3-de]quinoxaline-2,3-dione hydrochloride;

(S)-9-chloro-5-[p-tert-butoxycarbonylaminomethyl-o-(3,3-diethoxycarbonylpropyl)phenylcarbamoylmethyl]-6,7-dihydro-1H, 5H-pyrido[1,2,3-de]quinoxaline-2,3-dione;

(S)-9-chloro-5-[p-tert-butoxycarbonylaminomethyl-o-(3,3-dicarboxypropyl)phenylcarbamoylmethyl]-6,7-dihydro-1H, 5H-pyrido[1,2,3-de]quinoxaline-2,3-dione;

(S)-9-chloro-5-[aminomethyl-o-(3,3-dicarboxypropyl)phenylcarbamoylmethyl]-6,7-dihydro-1H, 5H-pyrido[1,2,3-de]quinoxaline-2,3-dione hydrochloride;

(S)-9-chloro-5-[aminomethyl-o-(3-carboxypropyl)phenylcarbamoylmethyl]-6,7-dihydro-1H, 5H-pyrido[1,2,3-de]quinoxaline-2,3-dione hydrochloride;

(S)-9-bromo-5-[p-tert-butoxycarbonylaminomethyl-o-(3,3-diethoxycarbonylpropyl)phenylcarbamoylmethyl]-6,7-dihydro-1H, 5H-pyrido[1,2,3-de]quinoxaline-2,3-dione;

(S)-9-bromo-5-[p-tert-butoxycarbonylaminomethyl-o-(3,3-dicarboxypropyl)phenylcarbamoylmethyl]- 6,7-dihydro-1H, 5H-pyrido[1,2,3-de]quinoxaline-2,3-dione;

(S)-9-bromo-5-[aminomethyl-o-(3,3-dicarboxypropyl)phenylcarbamoylmethyl]-6,7-dihydro-1H, 5H-pyrido[1,2,3-de]quinoxaline-2,3-dione hydrochloride;

and salts thereof;

wherein the numbering used for the tricyclic quinoxalinedione system is as shown in the following figure.

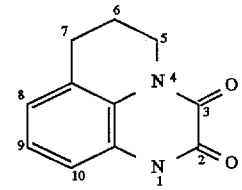

Process A-1

Compounds of formula 1 may generally be derived from key intermediates 3, which themselves are comprised of the invention;

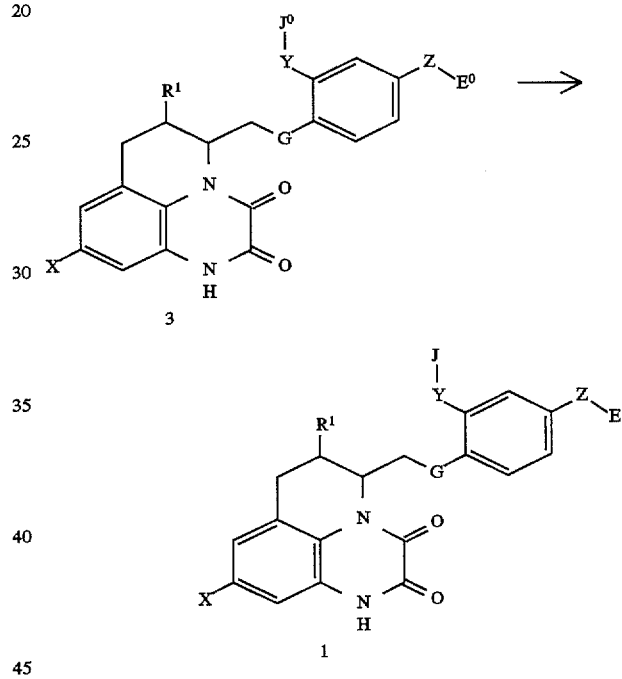

wherein X, $R^1$, G, Y, Z, J, E, $E^0$ and $J^0$ are as defined above.

Process A-2

The key intermediates of formula 3a may be prepared by condensation of 4 with 6;

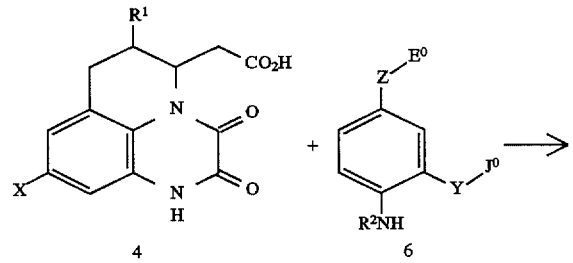

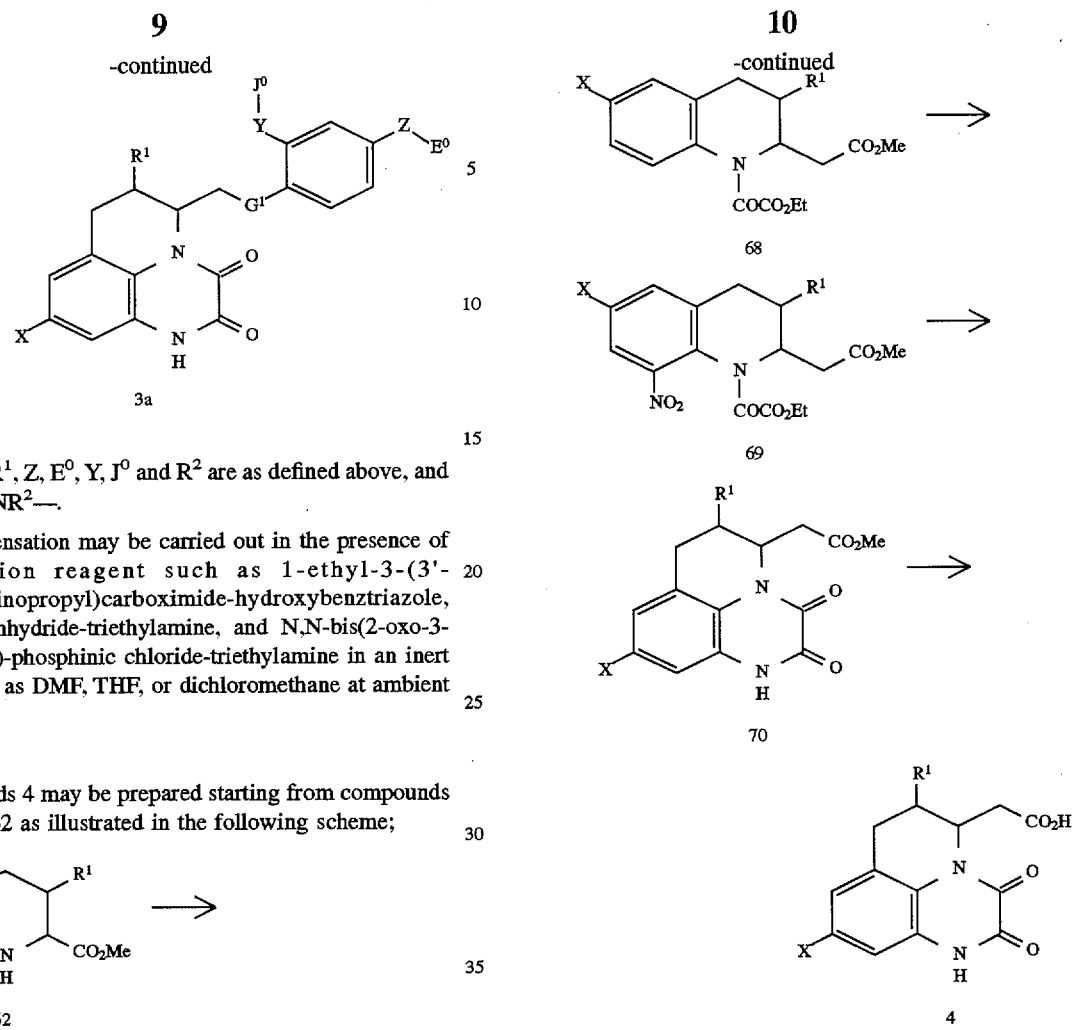

wherein X, $R^1$, Z, $E^0$, Y, $J^0$ and $R^2$ are as defined above, and $G^1$ is —$CONR^2$—.

The condensation may be carried out in the presence of condensation reagent such as 1-ethyl-3-(3'-dimethylaminopropyl)carboximide-hydroxybenztriazole, isobutyric anhydride-triethylamine, and N,N-bis(2-oxo-3-oxazolidinyl)-phosphinic chloride-triethylamine in an inert solvent such as DMF, THF, or dichloromethane at ambient temperature.

Process A-3

Compounds 4 may be prepared starting from compounds of formula 62 as illustrated in the following scheme;

wherein X and $R^1$ are as defined above.

Compounds of formula 62 may be readily prepared by a method described in literatures. For example, tetrahydroquinoline-2-carboxylic acid methyl ester may conveniently be prepared by hydrogenation of quinaldinic acid over $PtO_2$ in methanol followed by treatment of thionyl chloride in methanol at ambient to refluxing temperature, or by direct hydrogenation of quinaldinic acid methyl ester in acetic acid. Alternatively, tetrahydroquinoline-2-carboxylic acid methyl ester may be prepared by reduction of quinaldinic acid methyl ester with combination of $NiCl_2$ and sodium borohydride in methanol at 0° C. to room temperature. $R^1$ substituted tetrahydroquinoline-2-carboxylic acid methyl esters comprised in compounds 62 can be prepared by following sequence: a) Carboxyl group can be introduced into C-2 position of $R^1$ substituted corresponding quinolines by using Reissert reaction followed by hydrolysis (W. E. McEwen and R. L. Cobb, Chem. Rev., 55, 511 (1955)); and b) the resulting substituted quinoline-2-carboxylic acids were methylated, and then reduced to the corresponding tetrahydroquinoline-2-carboxylic acid methyl esters as mentioned above. The $R^1$ substituted quinolines may be commercially available or readily prepared by using Skraup reaction (R. H. F. Manske and M. Kulka, Org. React., 7, 59 (1953)). When $R^1$ is not hydrogen, compounds 62 may exist as a diastereomixture. Such a diastereomer can be conveniently separated to a pure isomer by a conventional column chromatography technique.

1) Compounds 62 are reduced to the corresponding alcohols 64 by using lithium aluminum hydride in an inert solvent such as diethyl ether or THF at 0° C. to refluxing temperature.

2) Compounds 64 can be converted into 65 by two step sequences: a) treatment with triphenyl phosphine-imidazole-iodine in toluene or in a mixed solvent of toluene-acetonitrile at 0° C. to ambient temperature to form the corresponding iodides, and b) replacement of the iodide to the cyanide with sodium cyanide in DMF at ambient temperature to around 80° C. to provide 65.

3) Hydrolysis of compounds 65 with a strong acid such as 12N hydrochloric acid at elevated temperature followed by methylation of the resulting carboxylic acid with thionyl chloride in methanol gives compounds 66.

4) Compounds of formula 66 are transformed to compounds 67 by reaction with ethyl chloroglyoxalate in an inert solvent such as methylene chloride, chloroform, tetrahydrofuran (THF), and ethyl acetate, at temperature range of −10° to 30° C.

5) Compounds 67 are converted to compounds 68 by using conventional aromatic electrophilic substitution technique (see, for example Advanced Organic Chemistry, Jerry March ed., Chapter 13, 576). In the case of X=Br, compounds 67 are reacted with bromine in halogenated solvent such as methylene chloride in the presence or absence of a catalyst such as Fe powder to give the brominated compounds comprised in 68. In the case of X=Cl, compounds 67 are reacted with N-chlorosuccinimide in dimethylformamide (DMF) at ambient temperature to give the chlorinated compounds comprised in 68. When X is Br, compounds 68 can also be synthesized by direct bromination of compounds 66 with N-bromosuccinimide in dimethylformamide (DMF) followed by acylation with ethyl chloroglyoxalate.

6) Compounds 68 can be transformed to compounds 69 by conventional nitration conditions including treatment with fuming nitric acid at 0° C. to ambient temperature, nitric acid or isopropyl nitrate in concentrated sulfuric acid at 0° C. to ambient temperature, a mixed reagent of trifluoroacetic anhydride and ammonium nitrate in halogenated solvent such as chloroform and methylene chloride at ambient to refluxing temperature, and nitronium tetrafluoroborate in halogenated solvent such as chloroform and methylene chloride at ambient temperature.

7) Reductive ring closure of compounds 69 to 70 are effected by aqueous titanium trichloride in protic solvent such as methanol, ethanol, and acetic acid or in aprotic solvent such as acetone, THF, or DMF at 0° C. to ambient temperature. Other reducing reagents including stannous dichloride, zinc, iron powder, and formate-palladium on carbon may be utilizable for the ring closure. The compounds of formula 70 wherein X is Br may be especially useful, since the Br substituent of X can be readily displaced to various substituents such as Cl, I, CN, alkyl, and $CF_3$ under conditions such as CuCl-dimethyl sulfoxide-150° C., CuI-Kl-hexamethylphosphorous triamide-150° C., CuCN-dimethyl sulfoxide-150° C., alkyl-copper reagent-THF-0° C., and $CF_3CO_2Na$—CuI-N-methylpyrrolidone-160° C., respectively. Compounds of formula 70 wherein X is hydrogen may be obtained by catalytic hydrogenation of compounds of formula 70 wherein X is Br by using Pd/C in methanol. Compounds of formula 70 wherein X is nitro may be obtained by standard nitration of compounds of formula 70 wherein X is hydrogen.

8) Carboxylic acids 4 can be prepared by hydrolysis of 70. The hydrolytic conditions include treatment with alkaline metal hydroxide or carbonate such as lithium hydroxide, sodium hydroxide, potassium carbonate in a mixed solvent of water and protic or aprotic solvent such as methanol, ethanol, or THF at temperature range of 0° to 50° C., or treatment with aqueous strong acid such as 1N~12N hydrochloric acid, or 5~48% hydrobromic acid in protic or aprotic solvent such as acetic acid or dioxane at temperature range of ambient temperature to 100° C.

Similarly, optically active 4 wherein $R^1$ is hydrogen may be prepared, if desired, starting from optically active 62 wherein $R^1$ is hydrogen of which synthesis is described in J. Chem. Soc. Perkin I 1977, 596.

Process A-4

Compounds 6 (6a and 6b) may be prepared as illustrated in the following scheme;

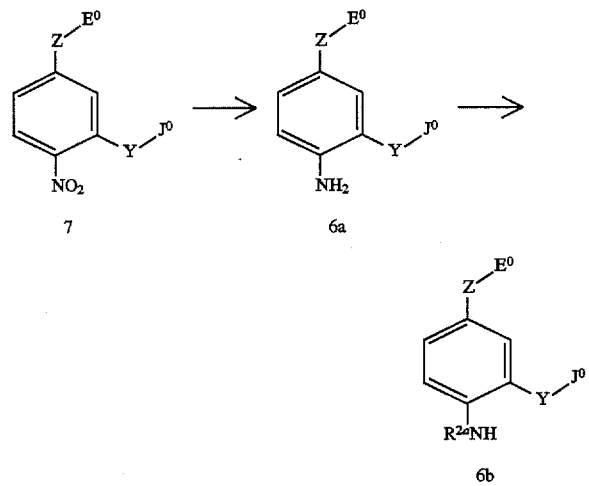

wherein Z, $E^0$, Y and $J^0$ are as defined above, and $R^{2a}$ is alkyl.

Compounds 6a may be obtained by reduction of the corresponding nitrobenzene derivatives 7. The reduction may be performed with conventional catalytic hydrogenation on palladium/charcoal or palladium hydroxide in an inert solvent such as ethyl acetate, methanol, or ethanol. Compounds 6b may be prepared by alkylation of compounds 6a with $R^{2a}I$ in the presence of a base such as potassium carbonate or sodium hydride. Reductive amination using an appropriate aldehydes or ketones in the presence of sodium borohydride or sodium cyanoborohydride in an alcoholic solvent such as methanol at ambient temperature may also be utilized for the alkylation.

Process B

Compounds of formula 7a may be prepared starting from readily available 8;

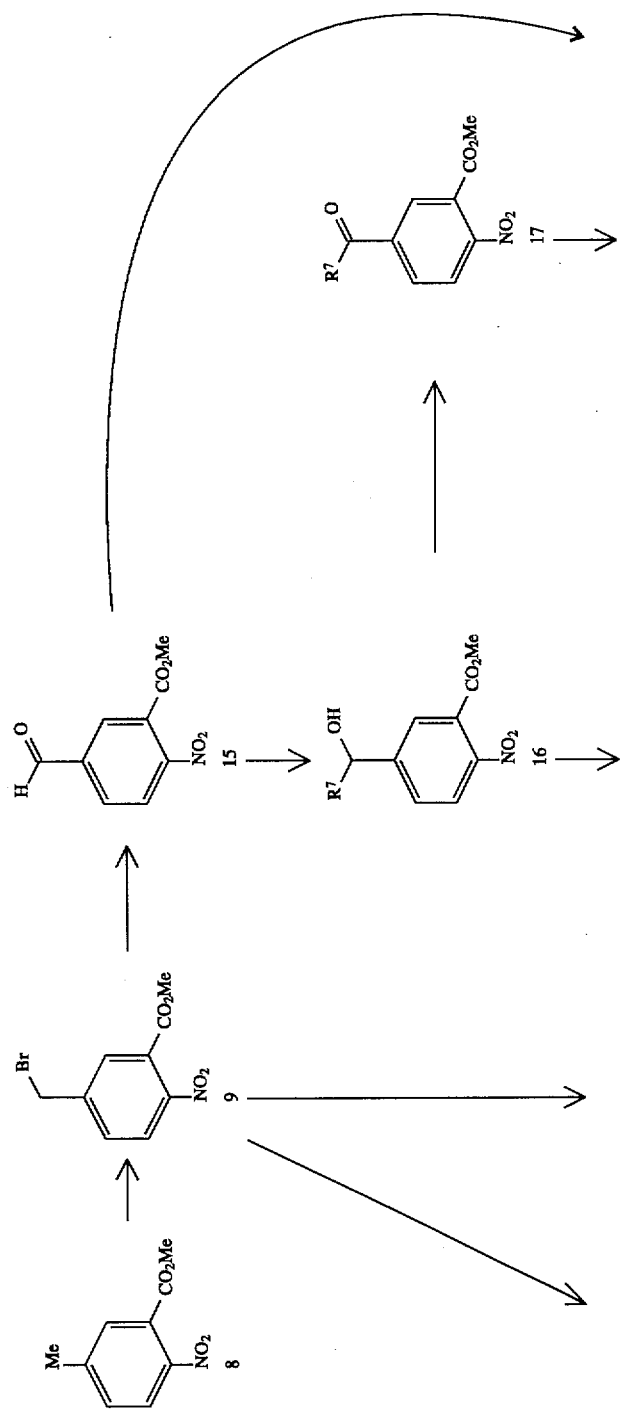

-continued
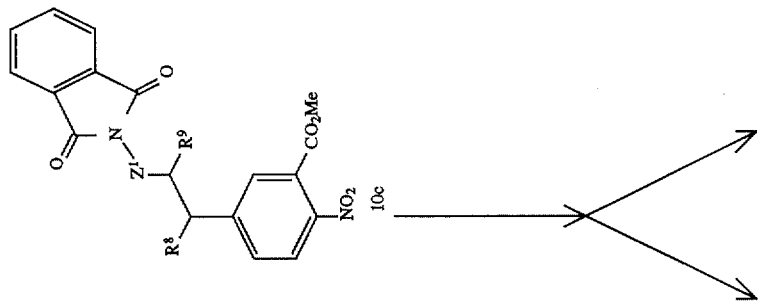
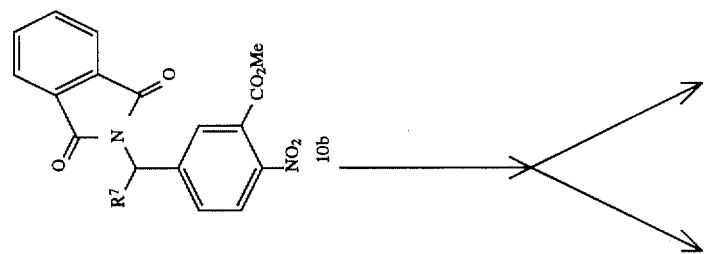
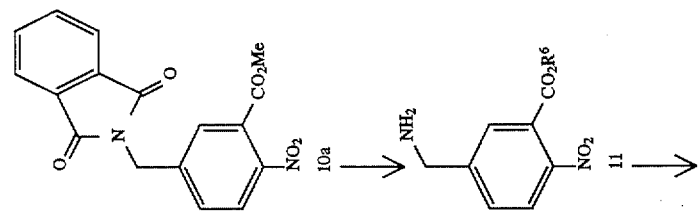
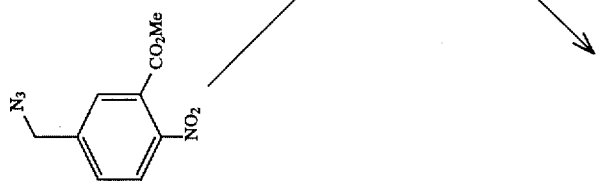

-continued
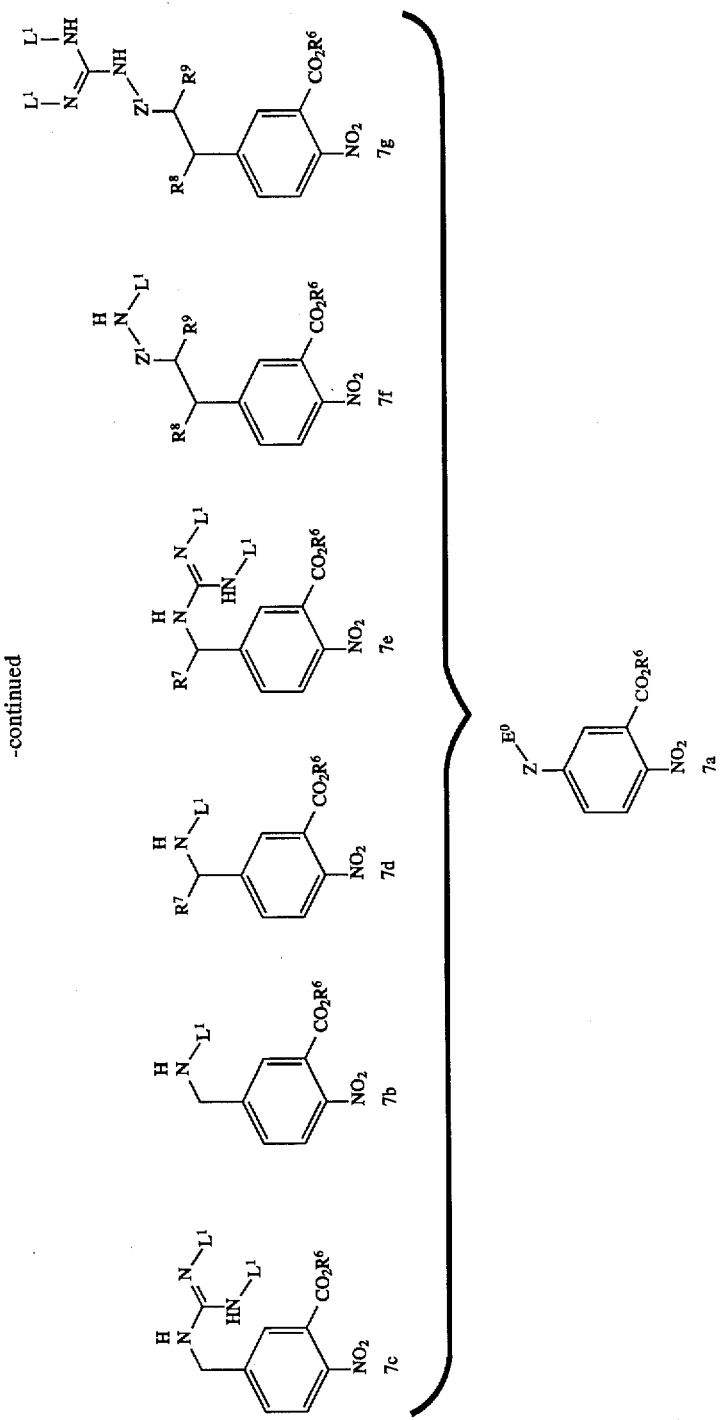

wherein Z, $E^0$, $L^1$ and $R^6$ are the same as defined above, $R^7$ is alkyl, $R^8$ is hydrogen or alkyl, $R^9$ is hydrogen or alkyl, and $Z^1$ is a single bond or alkylene.

Process B-1

Compounds 8 may be converted into compounds of formula 7b and 7c, as outlined below.

1) Compounds 8 may be brominated with N-bromosuccinimide in the presence of azobisisobutyronitrile (AIBN) or benzoyl peroxide (BPO) in an inert solvent such as carbon tetrachloride or chlorobenzene under reflux to provide 9.

2) Treatment of 9 with potassium phthalimide in an aprotic solvent such as DMF at temperature range of 50° to 80° C. may provide 10a.

3) Hydrolysis of 10a under acidic conditions followed by re-esterification with $R^6OH$ in the presence of acid promoter such as thionyl chloride or hydrogen chloride may afford compounds 11. The hydrolytic conditions include treatment with aqueous strong acid such as 6N~12N hydrochloric acid, or 25~48% hydrobromic acid in protic or aprotic solvent such as acetic acid or dioxane at temperature range of 50° to 100° C. Hydrolysis of phthalimide group of 10a may be utilized by hydrazine or methylhydrazine in protic solvent such as methanol at temperature range of 0° to 60° C. Compounds 11 may also be obtained by reaction of 9 with sodium azide in an aprotic solvent such as DMF at temperature range of 20° to 80° C. followed by hydrogenation over palladium/charcoal in an inert solvent such as ethyl acetate.

4) Free amines 11 may be protected with $L^1$ group to afford compounds of formula 7b. For example, reaction of 11 with di-t-butyl-dicarbonate in the presence of an organic base such as triethylamine in an inert solvent such as dichloromethane or ethyl acetate at ambient temperature affords compounds of formula 7b wherein $L^1$ is t-butoxycarbonyl. Treatment of 11 with MeSC(=$NL^1$) $NHL^1$ in the presence of an organic base such as triethylamine in an inert solvent such as dichloromethane or ethyl acetate at ambient temperature may afford compounds of formula 7c.

Process B-2

Compounds of formula 7d and 7e may be prepared as outlined below.

1) Bromides 9 can be oxidized to aldehydes 15 by an appropriate oxidation conditions. The conditions include reaction with dimethyl sulfoxide and trimethylamine N-oxide in dichloromethane at temperature range of 20° to 40° C.

2) Treatment of 15 with an alkylating reagent such as $R^7MgBr$ or $R^7Li$ in diethyl ether or THF at temperature range of -20° to 0° C. provides alcohols 16.

3) Mitsunobu reaction of 16 by using phthalimide, triphenylphosphine, and diethyl azodicarboxylate in THF at ambient temperature may afford compounds 10b, which may be converted into compounds of formula 7d and 7e, as described in the conversion of 10a into the compounds of formula 7b and 7c.

Process B-3

Compounds of formula 7f and 7g, may be prepared as outlined below.

1) Alcohols 16 may be oxidized to the corresponding ketones 17 by an appropriate oxidation conditions. The conditions include treatment with manganese oxide in dichloromethane at room temperature, treatment with DMSO-ClCOCOCl-triethylamine in dichloromethane at -70° C., treatment with pyridinium chlorocromate in dichloromethane at ambient temperature, and treatment with Dess-Martin reagent.

2) Reaction of aldehydes 15 or ketones 17 with Wittig reagent $PPh_3$=$CR^9$—$Z^1$-phthalimide in an inert solvent such as THF at temperature range of -70° to 60° C. followed by reduction with diimine generated from reaction of potassium azodicarboxylate with acetic acid in acetonitrile at temperature range of -20° to 0° C. affords compounds 10c, which may be converted into compounds of formula 7f and 7g as described in the conversion 10a into the compounds of formula 7b and 7c.

Process C-1 and C-2

Compounds of formula 7h and 7i, may be prepared as illustrated in the following scheme;

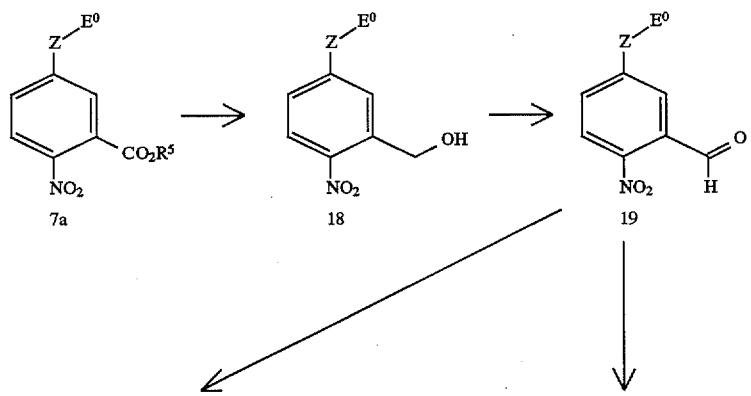

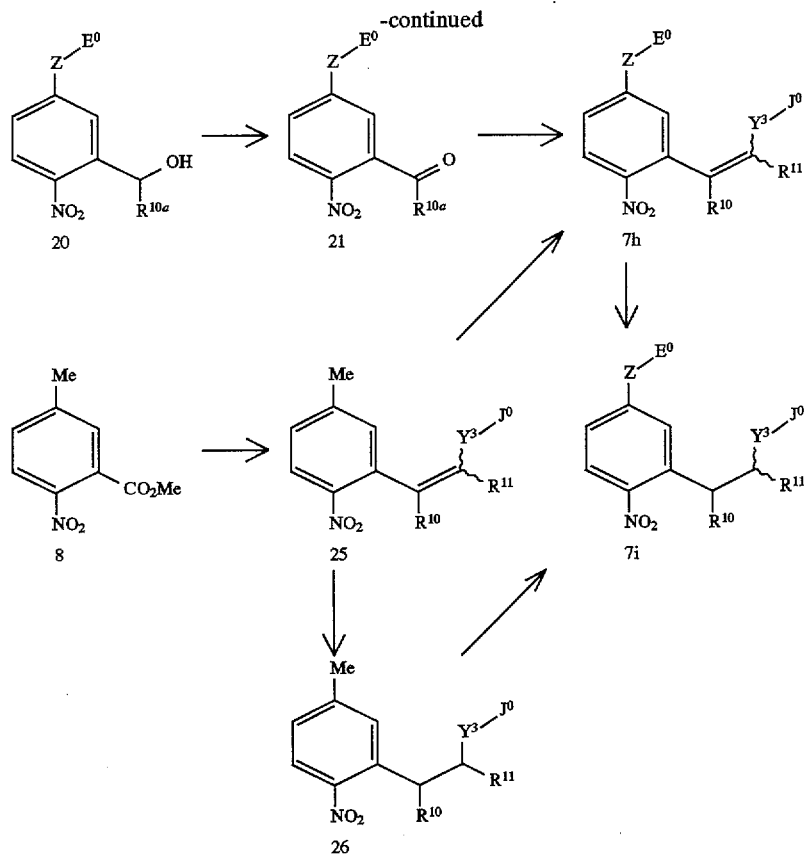

wherein $R^{10}$ and $R^{11}$ are independently hydrogen or alkyl, $Y^3$ is a single bond or alkylene, $R^{10a}$ is alkyl, and $Z$, $E^0$ and $J^0$ are as defined above.

Process C-1

1) Compounds 7a may be reduced to alcohols 18 by using sodium borohydride-methanol in THF at ambient to refluxing temperature.

2) Alcohols 18 may be oxidized to the corresponding aldehydes 19 under the conditions described in the conversion of 16 to 17.

3) Treatment of 19 with alkylating reagent such as $R^{10a}MgBr$ or $R^{10a}Li$ in diethyl ether or THF at temperature range of $-20°$ to $0°$ C. provides alcohols 20.

4) Alcohols 20 may be oxidized to the corresponding ketones 21 by an appropriate oxidation conditions. The conditions include treatment with DMSO-ClCOCOCl-triethylamine in dichloromethane at $-70°$ C., treatment with pyridinium chlorocromate in dichloromethane at ambient temperature, and treatment with Dess-Martin reagent.

5) Reaction of aldehydes 19 or ketones 21 with Wittig reagent $PPh_3=CR^{11}-Y^3-J^0$ in an inert solvent such as THF at temperature range of $-70°$ to $60°$ C. affords compounds of formula 7h, which may be selectively reduced to compounds of formula 7i, by catalytic hydrogenation using palladium/charcoal or by diimine reduction.

Process C-2

Alternatively, compounds of formula 7h and 7i may be prepared starting from compounds 8 as described below.

1) Compounds 8 may be converted into compounds 25 and 26 according to a sequence analogous to that used in the conversion of compounds 7a into compounds 7h and 7i, respectively (process C-1).

2) Compounds 25 and 26 may be converted into the corresponding compounds 7h and 7i, respectively, according to a sequence analogous to that used in the conversion of 8 into compounds 7a (process B).

Process C-3

Convenient methods for making a $-Y-J^0$ part of formula 7 may be a use of malonate anion.

Compounds of formula 32 and 7j, may be prepared as illustrated in the following scheme;

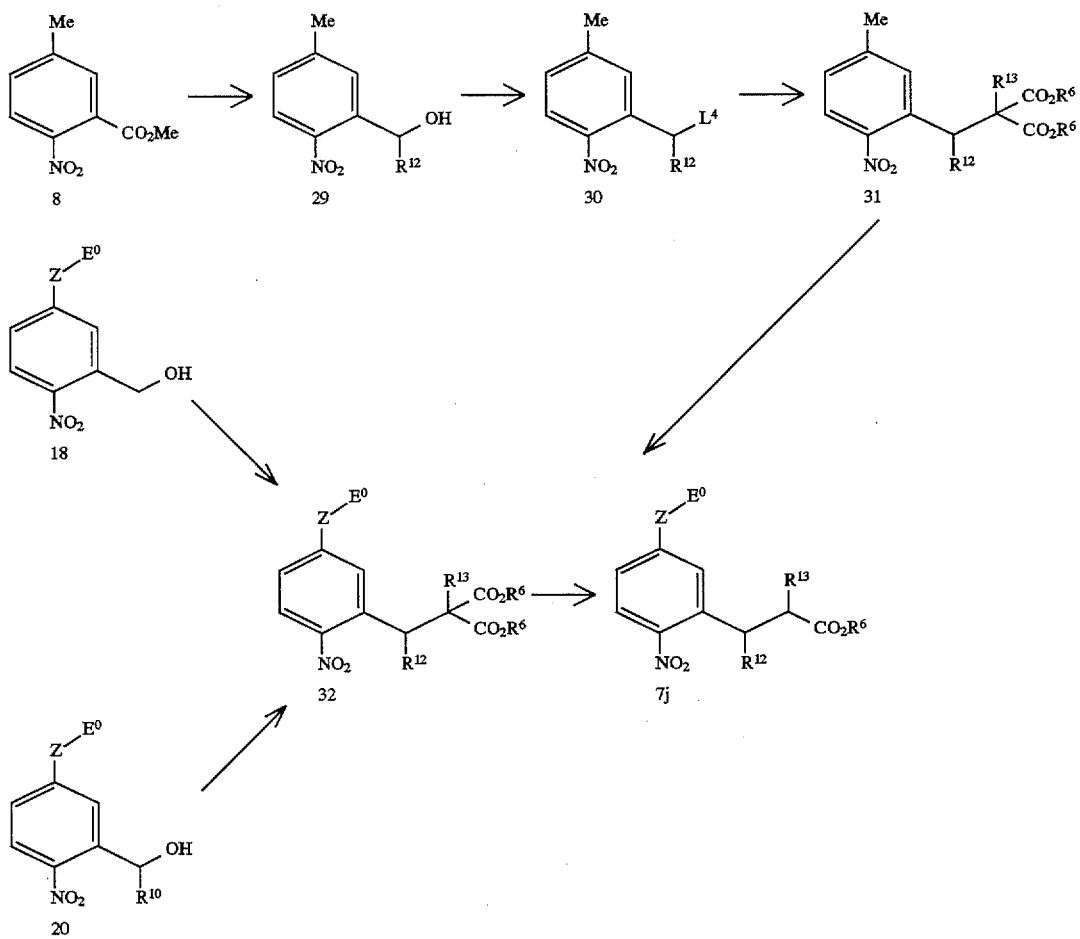

wherein Z, $E^0$, $R^6$ and $R^{10}$ are as defined above, $R^{12}$ is hydrogen or alkyl, $R^{13}$ is hydrogen or alkyl, and $L^4$ is a leaving group such as Cl, Br, I, $OSO_2Ph$, and $OSO_2CF_3$.

Compounds 8 may be converted into alcohols 29 by a sequence analogous to that used in the conversion of compounds 7a into 18 and 20 (process C-1, 1)–3)). Compounds 29 may be converted to 30. Herein, Cl and Br may be introduced by reaction with $SOCl_2$ or $SOBr_2$, and $CCl_4$—$PPh_3$ or $CBr_4$—$PPh_3$, respectively and I may be introduced by reaction of $I_2$—$PPh_3$-imidazole in an inert solvent at temperature range of 0° to 50° C. $PhSO_2O$— and $CF_3SO_2O$— groups may be prepared by reaction with $PhSO_2Cl$-triethylamine and $(CF_3SO_2)_2O$-triethylamine, respectively in an inert solvent such as dichloromethane at 0° C. to ambient temperature. Treatment of 30 with $R^6OCOCHR^{13}CO_2R^6$ in the presence of a base such as sodium hydride, potassium t-butoxide, and lithium hexamethyldisilazide in an aprotic solvent such as THF, DMF, or DMSO at temperature range of 0° to 60° C. provide 31. Compounds 31 may be converted into compounds 32, which are comprised of compounds of formula 7, according to a sequence analogous to that used in the conversion of 8 into compounds of formula 7a (process B). In some cases, an alkoxycarbonyl group of 32 may be simultaneously decarboxylated during the hydrolysis step of the phthalimide group to afford compounds of formula 7j. Alternatively, 18 and 20 may be converted into compounds 32 by a sequence similar to that described in the conversion of 29 to 31.

Process C-4

Compounds of formula 36 and 7k, may be prepared as illustrated in the following scheme;

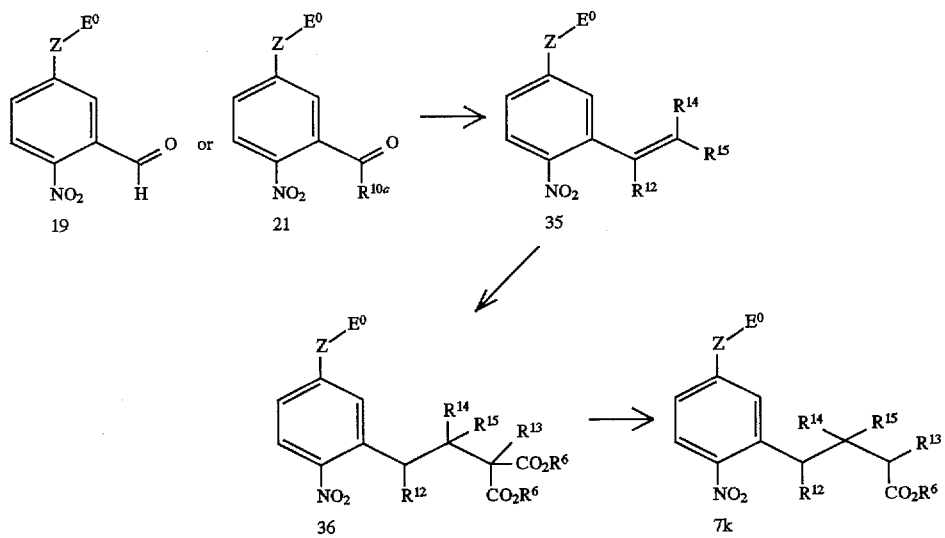

wherein Z, $E^0$, $R^6$, $R^{10a}$, $R^{12}$ and $R^{13}$ are as defined above, $R^{14}$ and $R^{15}$ are independently hydrogen or alkyl.

Compounds 19 and 21 may be converted into 35 by Wittig reaction with $PPh_3=CR^{14}R^{15}$ in an inert solvent such as THF at temperature range of $-70°$ to $60°$ C. Reaction of 35 with anion of $R^6OCOCHR^{13}CO_2R^6$ under conditions similar to those mentioned in the conversion of 30 into 31 may provide compounds 36 which are comprised of compounds of formula 7. An alkoxycarbonyl group of compounds 36 may be decarboxylated to hydrogen, if necessary, to provide compounds of formula 7k, under certain conditions such as heating in DMSO at elevated temperature in the presence of a salt such as sodium chloride.

Process C-5

Compounds of formula 7m and 7n, may be prepared as illustrated in the following scheme;

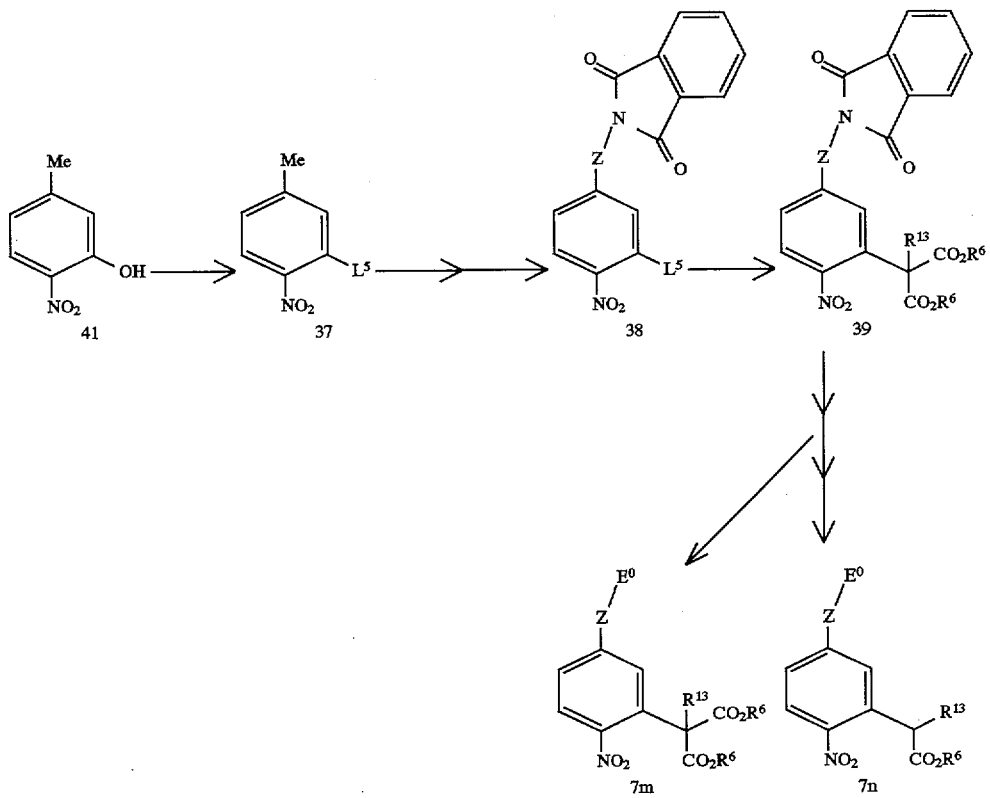

wherein Z, $E^0$, $R^6$ and $R^{13}$ are as defined above, and $L^5$ is a leaving group such as $OSO_2Ph$ or $OSO_2CF_3$.

Compounds 37 readily prepared from 41 as described in the conversion of 29 to 30 (process C-3), may be converted into 38 by a method similar to that described in the conversion of 8 into 10a,b,c (process B). Reaction of 38 with anion of $R^6OCOCHR^{13}CO_2R^6$ as mentioned in synthesis of 31 (process C-3) may provide compounds 39 which may be converted into compounds of formula 7m and 7n, according to a sequence analogous to that used in the conversion of 10a,b,c into the corresponding compounds of formula 7a (process B).

Process D-1

Compounds of formula 7p, may be prepared as illustrated in the following scheme;

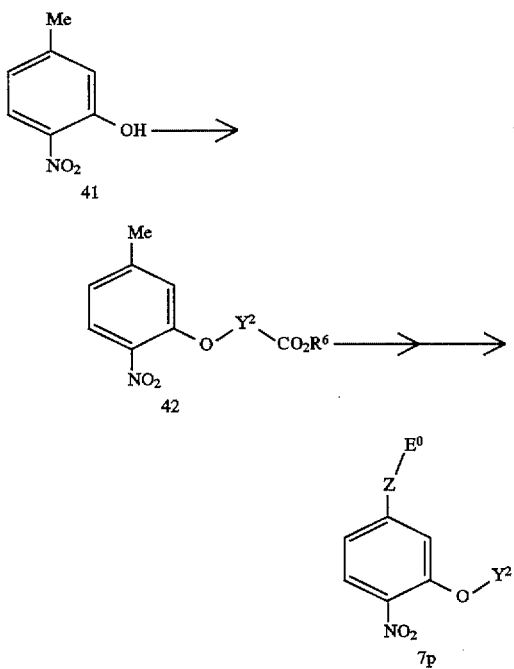

wherein $Y^2$ is alkylene, and Z, $E^0$ and $R^6$ are as defined above.

Compounds of formula 7p may be prepared from compound 41. Reaction of 41 with $BrY^2CO_2R^6$ in the presence of base such as potassium carbonate, potassium t-butoxide, or sodium hydride in an inert solvent such as acetonitrile, THF, DMF, or DMSO at temperature range of 0° to 60° C. may provide compounds 42. Conversion of 42 into compounds of formula 7p may be performed as described in the conversion of 8 into compounds of formula 7a (process B).

Process D-2

Compounds of formula 7q, may be prepared as illustrated in the following scheme;

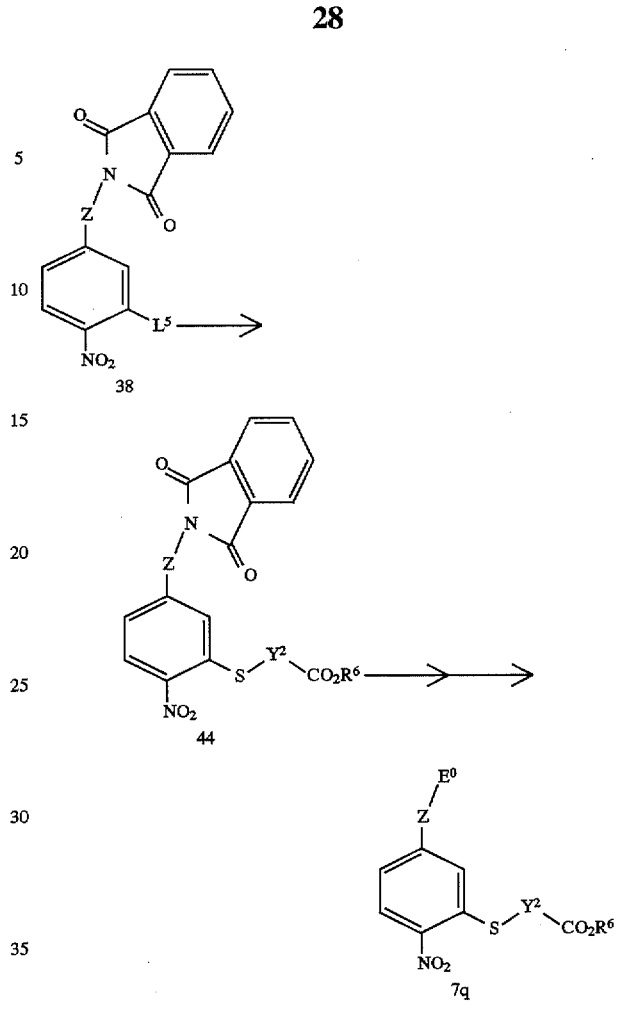

wherein Z, $E^0$, $Y^2$, $L^5$ and $R^6$ are as defined above.

Compounds of formula 7q may be prepared from compounds 38. Reaction of 38 with $HS-Y^2CO_2R^6$ in the presence of a base such as sodium hydride, potassium t-butoxide, and lithium hexamethyldisilazide in an aprotic solvent such as THF, DMF, or DMSO at temperature range of 0° to 60° C. may provide 44. Conversion of 44 into compounds of formula 7q may be performed as described in the conversion of 10a,b,c into the corresponding compounds of formula 7a (process B).

Process E-1

Compounds of formula 7r, may be prepared as illustrated in the following scheme;

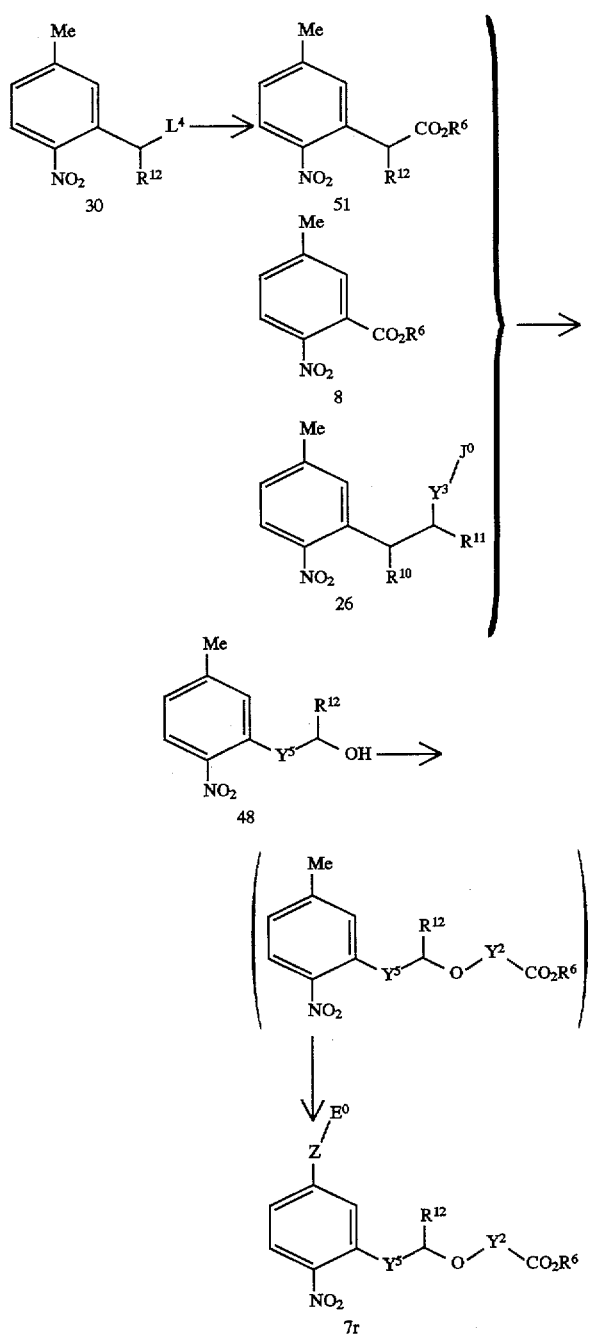

wherein Z, $E^0$, $J^0$, $L^4$, $Y^3$, $Y^2$, $R^{12}$ and $R^6$ are as defined above, and $Y^5$ is a single bond or alkylene.

Reaction of 30 with sodium cyanide in an aprotic solvent such as THF, DMF, or DMSO at ambient temperature to 60° C. followed by acid hydrolysis and esterification may provide compounds 51. Compounds 8, 26, and 51 may readily be converted into compounds of formula 48 as described in the conversion of 8 into 29 (process C-3). Reaction of 48 with $BrY^2CO_2R^6$ as described in the conversion of 41 to 42 (process D-1) followed by transformation similar to that described in the conversion of 8 into compounds of formula 7a (process B) may provide compounds of formula 7r.

Process E-2

Compounds of formula 7s, may be prepared as illustrated in the following scheme;

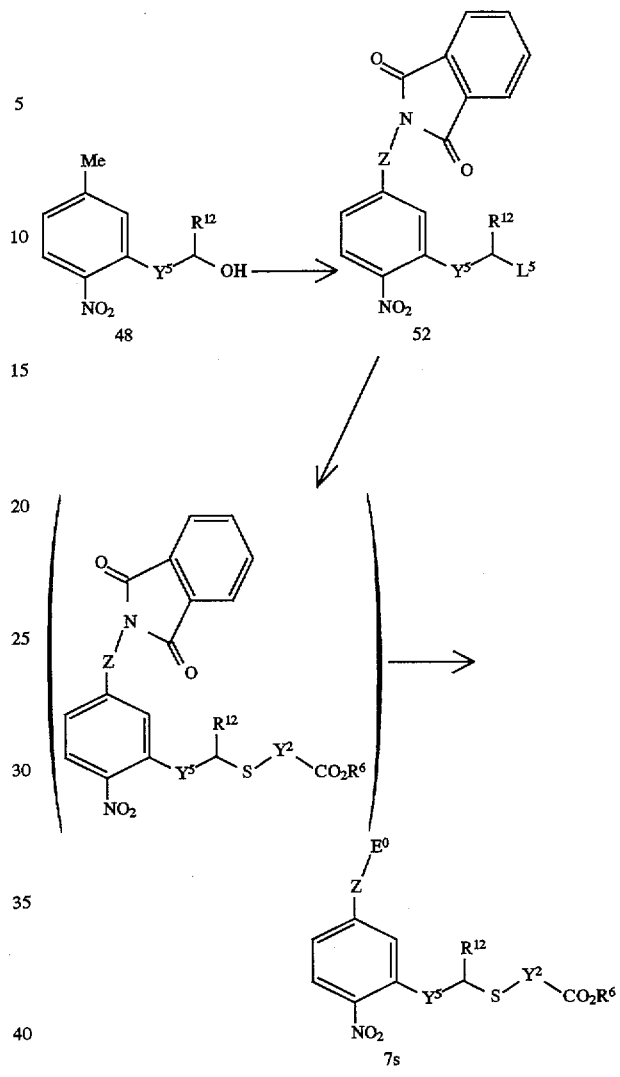

wherein Z, $E^0$, $L^5$, $Y^5$, $y^2$, $R^{12}$ and $R^6$ are as defined above.

Compounds 48 may be converted into compounds 52, as described in the conversion of 41 to 38 (process C-5). Reaction of 52 with $HSY^2CO_2R^6$ as described in the conversion of 38 to 44 (process D-2) followed by transformation similar to that described in the conversion of 10a,b,c into the corresponding compounds of formula 7a (process B) may provide compounds of formula 7s.

Process F-1

Compounds of formula 7t, may be prepared as illustrated in the following scheme;

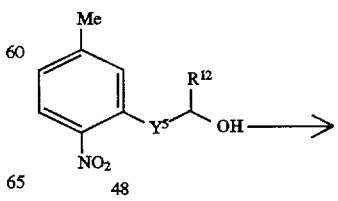

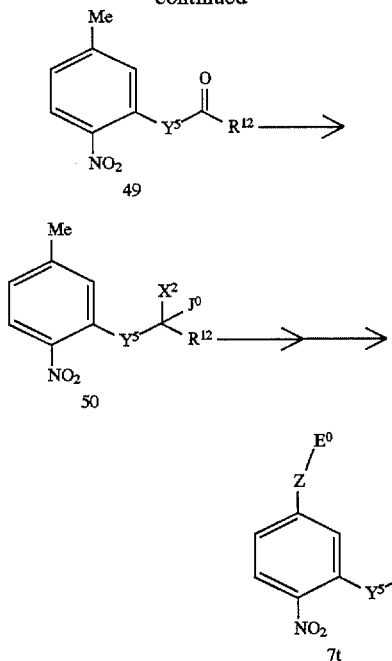

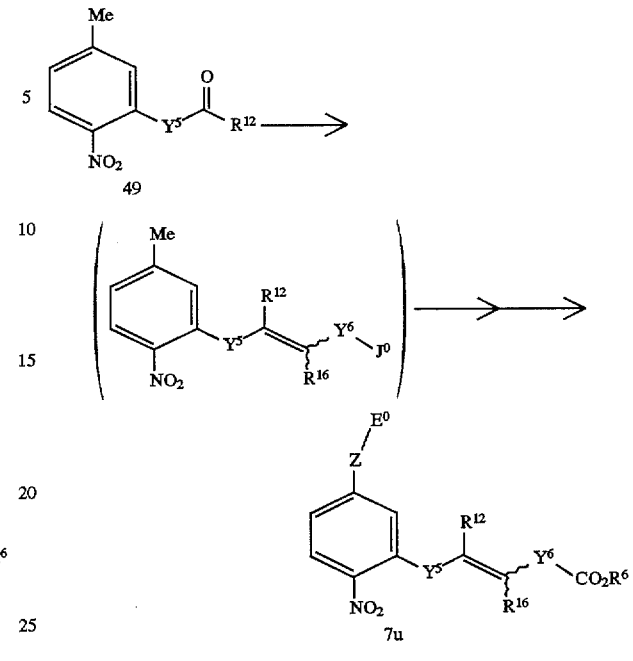

wherein Z, $E^0$, $J^0$, $R^{3S}$, $R^6$, $Y^5$ and $R^{12}$ are as defined above, and $X^2$ is $R^{3S}O—$, $R^{3S}CO_2$, $R^{3S}CONH—$, or $R^{3S}OCONH—$.

Compounds 48 may readily be oxidized into compounds of formula 49, as described in the conversion of 16 to 17 (process B). Treatment of 49 with trimethylsilyl cyanide in the presence of zinc iodide in dichloromethane at temperature range of 0° to 40° C. followed by acid hydrolysis and successive protection of the resulting carboxylic acid into $J^0$ and the alcohol into $X^2$ may provide compounds of formula 50 wherein $X^2$ represents $R^{3S}—$ or $R^{3S}COO—$ wherein $R^{3S}$ is as defined above. The protection of the alcohol to $—OR^{3S}$ may be carried out by treatment with $R^{3S}I$ in the presence of a base such as sodium hydride, potassium carbonate, and lithium hexamethyldisilazide in an aprotic solvent such as DMF, THF, or DMSO at temperature range of 40° to 80° C. The protection of the alcohols to $—OCOR^{3S}$ may be carried out by treatment with $R^{3S}COCl$ or $(R^{3S}CO)_2O$ in the presence of an organic base such as triethylamine and pyridine in an inert solvent such as dichloromethane at ambient temperature.

Similarly, compounds 49 may be converted into compounds of formula 50 wherein $X^2$ represents $R^{3S}CONH—$ and $R^{3S}OCONH—$ by conventional Strecker or Bucherer synthesis followed by protection. The protection of the resulting amine may be carried out by treatment with $R^{3S}COCl$, $(R^{3S}CO)_2O$, $R^{3S}OCOCl$, or $(R^{3S}OCO)_2O$ in the presence of an organic base such as triethylamine or pyridine in an inert solvent such as dichloromethane at ambient temperature.

Compounds 50 may be transformed into compounds of formula 7t, by a route similar to that described in the conversion of 8 into compounds 7a (process B).

Process F-2

Compounds of formula 7u, may be prepared as illustrated in the following scheme;

wherein Z, $E^0$, $J^0$, $Y^5$, $R^{12}$ and $R^6$ are as defined above, $Y^6$ is a single bond or alkylene, $R^{16}$ is hydrogen or alkyl.

Reaction of compounds of formula 49 with Wittig reagent $PPh_3=CR^{16}—Y^6—J^0$ in an inert solvent such as THF at temperature range of −70° to 60° C. followed by transformation similar to that described in the conversion of 8 into compounds 7a (process B) affords compounds of formula 7u.

Process G

Compounds of formula 3b, may be prepared as illustrated in the following scheme;

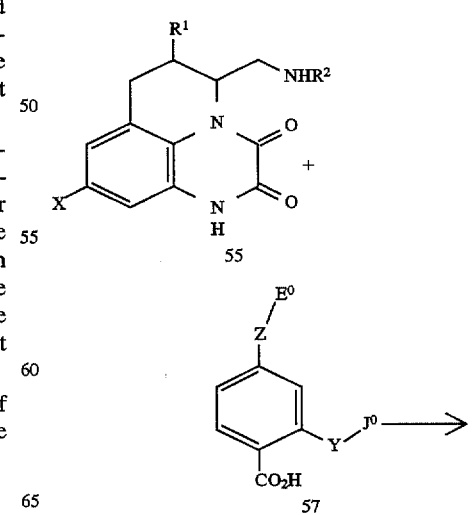

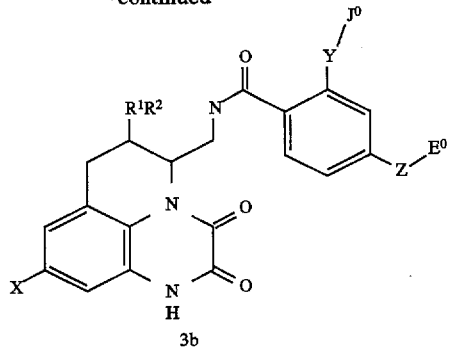

wherein X, R$^1$, R$^2$, Z, E$^0$, Y and J$^0$ are as defined above.

Compounds of formula 1 wherein G is —NR$^2$CO— may also be derived from the key intermediates 3b, which themselves are comprised of the invention. The key intermediates 3b may be prepared by condensation of 55 with 57, as described in that of 4 with 6 (process A-2).

Process H-1

Compounds of formula 55 (55a and 55b), may be prepared starting from compounds 64 as illustrated in the following scheme;

corresponding iodide, and b) replacement of the iodide to the phthalimide with potassium phthalimide in DMF at ambient temperature to around 80° C. to provide 73. Alternatively, compounds 73 are prepared from 62 by three steps sequence: a) treatment of 62 with ammonia in methanol to give the corresponding amides, b) conversion of the amides to the corresponding diamines by using lithium aluminum hydride in THF at reflux temperature, and c) condensation of the diamines with phthalic anhydride in toluene under azeotropic conditions.

2) Transformation of 73 into the compounds 74 can be carried out as described in the conversion of 66 into 70. The compounds of formula 74 wherein X is Br may be especially useful, since the Br substituent of X can be readily displaced to various substituents such as Cl, I, CN, alkyl, and CF$_3$ under conditions such as CuCl-dimethyl sulfoxide-150° C., CuI-KI-hexamethyl-phosphorous triamide-150° C., CuCN-dimethyl sulfoxide-150° C., alkyl-copper reagent-THF-0° C., and CF$_3$CO$_2$Na—CuI-N-methylpyrrolidone-160° C., respectively. Compounds of formula 74 wherein X is hydrogen may be obtained by catalytic hydrogenation of compounds of formula 74 wherein X is Br by using Pd/C in methanol. Compounds of formula 74 wherein X is nitro may be obtained by standard nitration of compounds of formula 74 wherein X is hydrogen.

3) Acid hydrolysis of 74 may afford the compounds of formula 55a. The acid hydrolysis conditions include treat-

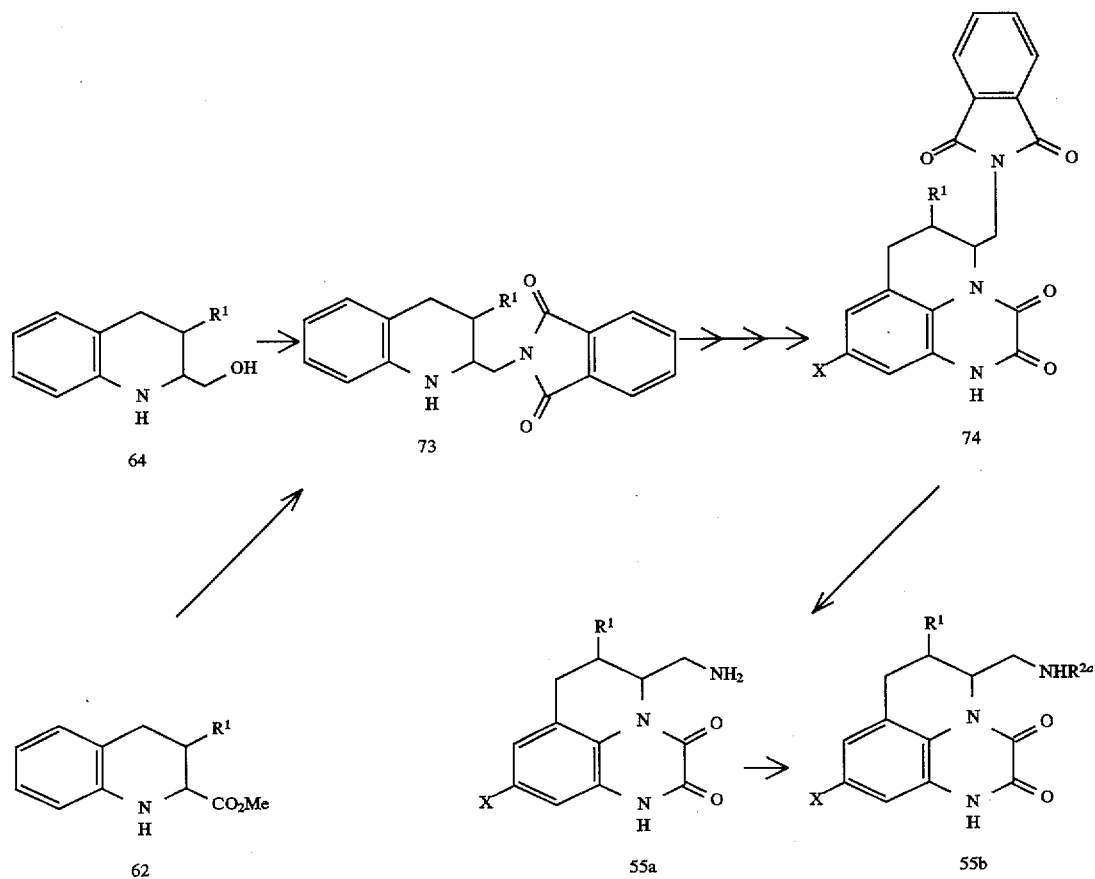

wherein X, R$^1$ and R$^{2a}$ are as defined above.

1) Compounds 64 can be converted into 73 by two steps sequence: a) treatment with triphenyl phosphine-imidazole-iodine in toluene or in a mixed solvent of toluene-acetonitrile at 0° C. to ambient temperature to form the ment with aqueous strong acid such as 6N~12N hydrochloric acid, or 25~48% hydrobromic acid in protic or aprotic solvent such as acetic acid or dioxane at temperature range of 50° to 100° C.

Compounds 55b may be prepared by alkylation of compounds 55a with $R^{2a}I$ in the presence of a base such as potassium carbonate or sodium hydride. Reductive amination using an appropriate aldehydes or ketones in the presence of sodium borohydride or sodium cyanoborohydride in an alcoholic solvent such as methanol at ambient temperature may also be utilized for the alkylation.

Similarly, Optically active 55 wherein $R^1$ is hydrogen may be prepared starting from optically active 62 wherein $R^1$ is hydrogen of which synthesis is described in J. Chem. Soc. Perkin I 1977, 596.

Process H-2

The key intermediates 57 may be prepared from compounds 6a;

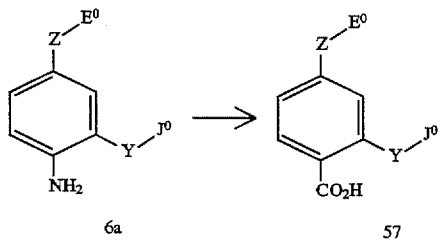

wherein Z, $E^O$, Y and $J^O$ are as defined above.

Reaction of 6a with alkyl nitrite such as isopropyl nitrite in the presence of copper cyanide in an inert solvent such as acetonitrile followed by acid or alkaline hydrolysis of the resulting cyano group and selective re-protection of the carboxylic acid group of the side chain into $J^O$ and the amino or guanidino group (if necessary) into $E^O$ may provide 57. The hydrolytic conditions include treatment with alkaline metal hydroxide or carbonate such as lithium hydroxide, sodium hydroxide, potassium carbonate in a mixed solvent of water and protic or aprotic solvent such as methanol, ethanol, or THF at temperature range of 0° to 50° C., or treatment with aqueous strong acid such as 1N~12N hydrochloric acid, or 5~48% hydrobromic acid in protic or aprotic solvent such as acetic acid or dioxane at temperature range of ambient temperature to 100° C.

Process J

Compounds 3 of the invention may be hydrolyzed to compounds of formula 1 wherein E is $E^O$ and J is $CO_2H$ by treatment of aqueous alkaline hydroxide such as lithium hydroxide and sodium hydroxide in a mixed solvent of methanol and THF at ambient temperature. Compounds of formula 1 wherein E is $E^O$ and J is $CO_2H$ may be condensed with $NH_3$, $NH_2R^{3J}$, $HNR^{3J}R^{4J}$, $HN(OH)R^{3J}$, $HN(OR^{5J})R^{3J}$, $H_2NOH$ and $HOR^{3J}$ to give compounds of formula 1 wherein J is $CONH_2$, $CONHR^{3J}$, $CONR^{3J}R^{4J}$, $CON(OH)R^{3J}$, $CON(OR^{5J})R^{3J}$, $CON(OH)H$ and $CO_2R^{3J}$, respectively, wherein $R^{3J}$, $R^{4J}$ and $R^{5J}$ are as defined above and E is $E^O$. The condensation may be carried out in the presence of condensation reagent such as 1-ethyl-3-(3'-dimethylaminopropyl)carboximide-hydroxybenztriazole, isobutyric anhydride-triethylamine, and N,N-bis(2-oxo-3-oxazolidinyl)-phosphinic chloride-triethylamine in an inert solvent such as DMF, THF, or dichloromethane at temperature range of 0° C. to ambient temperature.

Similar condensation of compounds of formula 1 wherein E is $E^O$ and J is $CO_2H$ with 3-aminopropionitorile followed by treatment of triphenylphosphine, diethyl azodicarboxylate, and trimethylsilyl cyanide in THF at ambient temperature and alkaline hydrolysis may provide compounds of formula 1 wherein J is tetrazolyl and E is $E^O$.

Compounds of formula 1 wherein E is $E^O$ may be selectively deprotected to compounds of formula 1 wherein E is $-NH_2$ or $-NHC(=NH)NH_2$ by mild acid hydrolysis. The hydrolytic conditions includes treatment with 0.1~4N hydrogen chloride in an inert solvent such as 1,4-dioxane and ethyl acetate at ambient temperature.

Compounds of formula 1 wherein E is $NHR^{3E}$ or $-NHC(=NH)NHR^{3E}$ may be prepared by alkylation of compounds of formula 1 wherein E is $-NH_2$ or $-NHC(=NH)NH_2$ with $R^{3E}I$ wherein $R^{3E}$ is as defined above in the presence of a base such as potassium carbonate or sodium hydride. Compounds of formula 1 wherein E is $NR^{3E}R^{4E}$ or $-NHC(=NH)NR^{3E}R^{4E}$ may also be prepared by further alkylation of compounds of formula 1 wherein E is $NHR^{3E}$ or $-NHC(=NH)NHR^{3E}$ with $R^{4E}I$ as described above, wherein $R^{3E}$ and $R^{4E}$ are as defined above. Compounds of formula 1 wherein E is $NR^{3E}R^{4E}$ or $-NHC(=NH)NR^{3E}R^{4E}$ wherein $R^{3E}$ and $R^{4E}$ are joined to form a cyclic amine may also be prepared by alkylation of compounds of formula 1 wherein E is $NH_2$ or $-NHC(=NH)NH_2$ with $I—Q^2—I$ as described above, wherein $Q^2$ represents alkylene containing 2 to 6 carbon atoms which may be a straight-chained or alkylene containing 4 to 6 carbon atoms and an oxygen or nitrogen atom which may be straight-chained. The oxygen or nitrogen atom of $Q^2$ is always bonded to the adjacent alkylene group. Reductive amination using an appropriate aldehydes or ketones in the presence of sodium borohydride or sodium cyanoborohydride in an alcoholic solvent such as methanol at ambient temperature may also be utilized for introducing $R^{3E}$ and $R^{4E}$ groups. Compounds of formula 1 wherein E is $-NH_2$, $-NHR^{3E}$, $-NH—C(=NH)—NH_2$, $-NH—C(=NH)—NHR^{3E}$, and $-NH—C(=NH)—NR^{3E}R^{4E}$ may be converted into compounds of formula 1 wherein E is $-NHL$, $-NLR^{3E}$, $-NH—C(=NL)—NH_2$, $-NH—C(=NL)—NHR^{3E}$, and $-NH—C(=NL)—NR^{3E}R^{4E}$ wherein L is $R^{17}CO$ or $R^{17}OCO$ wherein $R^{17}$ is alkyl, and $R^{3E}$ and $R^{4E}$ are as defined above. The conversion may be carried out by treatment with $R^{17}COCl$, $(R^{17}CO)_2O$, $R^{17}OCOCl$, or $(R^{17}OCO)_2O$ in the presence of an organic base such as triethylamine or pyridine in an inert solvent such as dichloromethane at ambient temperature.

According to the methods as described above, the compounds of the invention may be prepared as racemic form. However, the compounds of the invention may be obtained as enantiomeric pure form by resolving an appropriate racemic intermediate during the synthesis, or the compounds of the invention themselves. The resolution includes salt-formation of the compound having a basic moiety with optically pure acid such as (+)-tartaric acid, and also salt-formation of the compound having an acidic moiety with optically pure amine such as quinine or quinidine, followed by fractional recrystallization and regeneration of the parent compound. The resolution technique also includes amide or ester formation of the compound having carboxylate, amine, or alcohol with chiral-auxiliary, followed by chromatographic separation and removal of the auxiliary. Alternative resolution technique includes enzymatic hydrolysis of the ester or amide of the intermediate during the synthesis or the compound in the invention.

A certain compound in the invention may be obtained by using conventional protection-deprotection techniques, if necessary or desirable, during synthesis as described above. Such techniques are described in T. W. Greene, Protective Groups in Organic Synthesis, John Wiley & Sons, 1981.

The compounds of the present invention strongly inhibit both [$^3$H] 5,7-dichlorokynurenic acid (DCKA) and [$^3$H] glycine binding to the rat brain synaptic membrane preparation, implying that these compounds possess the potent affinities for strychnine-insensitive glycine modulatory site of NMDA (N-methyl D-aspartate) receptors (see, for example, Y. Yoneda, et al., J. Neurochem., 60, 634 (1993)). The activities of the compounds were measured by [$^3$H] DCKA and [$^3$H] glycine binding inhibition studies as illustrated below.

[$^3$H] glycine binding studies

A crude rat brain synaptic membrane preparation was washed three times by centrifugation at 50,000×g for 30 min with 50 mM tris acetate (pH 7.4). The pellets obtained were suspended in 0.23M sucrose solution and stored at −80° C. For binding studies, the frozen suspension was thawed, treated with 0.08% triton X-100 at 2° C. for 10 min, and washed twice by the centrifugation as mentioned above. The synaptic membrane thus prepared (ca. 150~200 μg of protein) was incubated with 10 nM [$^3$H] glycine (1.11 TBq/mmol) and the test compound (10 ng/mL~0.1 ng/mL) at 2° C. for 10 min in 50 mM tris acetate (pH 7.4). The incubation was terminated by suction filtration using Whatman GF/B glass filter. The radioactivities bound to the membrane on the filter was measured by scintillation counting. Non-specific binding was calculated by the radioactivities measured under the incubations in the presence of 0.1 mM D-serine. The [$^3$H] glycine binding was not inhibited by addition of 0.1 mM strychnine.

[$^3$H] DCKA binding studies

A crude rat brain synaptic membrane preparation was washed three times by centrifugation at 50,000×g for 30 min with 50 mM tris acetate (pH 7.4). The pellets obtained were suspended in 0.23M sucrose solution and stored at −80° C. For binding studies, the frozen suspension was thawed, treated with 0.08% triton X-100 at 2° C. for 10 min, and washed twice by the centrifugation as mentioned above. The synaptic membrane thus prepared (ca. 100 μg of protein) was incubated with 10 nM [$^3$H] (DCKA) (603 GBq/mmol) and the test compound (10 ng/mL~0.1 ng/mL) at 2° C. for 10 min in 50 mM tris acetate (pH 7.4). The incubation was terminated by suction filtration using Whatman GF/B glass filter. The radioactivities bound to the membrane on the filter was measured by scintillation counting. Non-specific binding was calculated by the radioactivities measured under the incubations in the presence of 0.1 mM glycine.

The compounds of the present invention attenuated strongly NMDA-induced seizure under systemic administrations in the following in vivo model.

NMDA-induced seizure model

Thirty min later following intraperitoneal administration of the test compound (0.3~30 mg/kg) into each of ten mice tested, NMDA (5 nmol) was administered intracerebroventricularly (i.c.v.). Under the conditions without pretreatment of the test compound, all of the mice exhibit tonic seizures. The number of mice which did not exhibit tonic seizures after i.c.v. administration of NMDA was counted as considered to be protected. The activity of the test compound may be shown by the $ED_{50}$ value. As favourable examples, the compounds of Example 31, 35, and 11 inhibited the seizures with $ED_{50}$ values of 1.0, 2.1 and 3.1 mg/kg, respectively.

Reference Example 1

9-Bromo-5-methoxycarbonylmethyl-6,7-dihydro-1H, 5H-pyrido[1,2,3-de]quinoxaline-2,3-dione 1) 2-Hydroxymethyltetrahydroquinoline To a suspension of LiAlH$_4$ (8.3 g, 0.22 mol) in THF (200 mL) was added dropwise 2-methoxycarbonyltetrahydroquinoline (42 g, 0.22 mol) in THF (200 mL) at 0° C. The mixture was stirred for 3 h at room temperature and refluxed for 0.5 h. The excess reagent was decomposed by addition of aqueous sodium hydroxide in THF. To the mixture was added 1N aqueous NaOH, water, and diethyl ether, successively. The organic layer was separated, washed with brine, dried over magnesium sulfate, and concentrated to give 38.4 g of 2-hydroxymethyltetrahydroquinoline (quant).

$^1$H NMR (270 MHz, CDCl$_3$) δ6.95~7.00 (m, 2H), 6.63 (t, 1H, J=7.4 Hz), 6.54 (d, 1H, J=7.4 Hz), 3.74 (dd, 1H, J=10.2, 3.6 Hz), 3.56 (dd, 1H, J=10.2, 8.6 Hz), 3.41~3.49 (m, 1H), 2.70~2.85 (m, 2H), 1.85~1.90 (m, 1H), 1.68~1.77 (m, 1H).

2) 2-Cyanomethyltetrahydroquinoline

To a solution of 2-hydroxymethyltetrahydroquinoline (35.9 g, 0.22 mol), imidazole (35.95 g, 0.528 mol), and triphenylphosphine (69.24 g, 0.264 mol) in a mixed solvent of 5:1 toluene/acetonitrile (750 mL) was added iodine (61.42 g, 0.242 mol) at 0° C. The mixture was stirred for 15 min at 0° C. and for 30 min at room temperature. Aqueous sodium thiosulfate solution (200 mL) was added. The organic layer was separated, washed with brine, dried over magnesium sulfate, and concentrated. The residue was triturated with diethyl ether and the insoluble materials were removed by filtration. The filtrate was concentrated and the residual oil was dissolved in DMF (200 mL). To the solution was added sodium cyanide (43.2 g, 0.881 mol) and the mixture was heated at 80° C. for 10 h. The resulting mixture was poured into ice-water and extracted with a mixture of toluene and ethyl acetate. The organic layer was washed with brine, dried over magnesium sulfate, and concentrated. The residue was purified by silica gel column chromatography with 1:1 hexane/dichloromethane to 100% dichloromethane as eluents to give 31.6 g of the title compound (94%).

$^1$H NMR (270 MHz, CDCl$_3$) δ6.97~7.04 (m, 2H), 6.68 (t, 1H, J=7.4 Hz), 6.54 (d, 1H, J=7.4 Hz), 4.03 (br, 1H), 3.70 (m, 1H), 2.70~2.86 (m, 2H), 2.54 (d, 1H, J=6.6 Hz), 2.02~2.13 (m, 1H), 1.78~1.91 (m, 1H).

3) 2-Methoxycarbonylmethyltetrahydroquinoline

2-Cyanomethyltetrahydroquinoline (28.0 g, 0.163 mol) was dissolved in concentrated hydrochloric acid (200 mL) and the mixture was refluxed for 4 h. The resulting mixture was concentrated and the residue was dissolved in methanol (500 mL). Thionyl chloride (36 mL, 0.49 mol) was added slowly at 0° C. The mixture was refluxed for 5 h and concentrated. To the residual solid was added slowly saturated sodium bicarbonate (1 L) and the mixture was extracted with ethyl acetate. The organic layer was washed with brine, dried over magnesium sulfate, and concentrated to give 31.6 g of the title compound (94%). 2-Methoxycarbonylmethyltetrahydroquinoline hydrochloride.

$^1$H NMR (270 MHz, CDCl$_3$) δ7.69~7.72 (m, 1H), 7.23~7.38 (m, 3H), 3.96~4.05 (m, 1H), 3.75 (s, 3H), 3.48~3.55 (m, 1H), 2.96~3.12 (m, 3H), 2.19~2.41 (m, 1H).

4) 6-Bromo-2-methoxycarbonylmethyltetrahydroquinoline

To a solution of 2-methoxycarbonylmethyltetrahydroquinoline (31.5 g, 0.153 mol) in DMF (750 mL) was added dropwise a solution of N-bromosuccinimide (27.41 g, 0.154 mol) in DMF (550 mL) at 0° C. The mixture was stirred for 2 h at the same temperature, poured into water (2 L), and extracted with a mixture of toluene and ethyl acetate. The organic layer was washed with water, dried over magnesium sulfate, and concentrated to give 44.72 g of the title compound (quant).

$^1$H NMR (270 MHz, CDCl$_3$) δ7.02~7.06 (m, 2H), 6.38 (dd, 1H, J=1.7, 7.3 Hz), 4.53 (br, 1H), 3.75 (s, 3H), 3.72~3.75 (m, 4H), 2.70~2.85 (m, 2H) 2.49~2.53 (m, 1H), 1.89~1.99 (m, 1H), 1.61~1.75 (m, 1H).

5) 6-Bromo-2-methoxycarbonylmethyl-N-ethoxalyltetrahydroquinoline

To a solution of 6-bromo-2-methoxycarbonylmethyltetrahydroquinoline (43.8 g, 0.153 mol) and triethylamine (37.5 g, 0.371 mol) in dichloromethane (700 mL) was added slowly ethyl chlorooxalate (25.5 g, 0.187 mol) at 0° C. The mixture was stirred for 3 h at 0° C., poured into 0.3N hydrochloric acid (750 mL) and extracted with dichloromethane. The organic layer was washed with brine, dried over magnesium sulfate, and concentrated. The residue was purified by silica gel column chromatography with 4:1 to 3:1 hexane/ethyl acetate to give 56.9 g of the title compound (97%).

$^1$H NMR (270 MHz, CDCl$_3$) δ7.36 (s, 1H), 7.30 (d, 1H, J=8.3 Hz), 6.92 (d, 1H, J=8.3 Hz), 4.94~5.01 (m, 1H), 4.13~4.16 (m, 2H), 3.64 (s, 3H), 2.4~2.75 (m, 6H), 1.11~1.26 (m, 3H).

6) 6-Bromo-2-methoxycarbonylmethyl-8-nitro-N-ethoxalyltetrahydroquinoline

A solution of 6-bromo-2-methoxycarbonylmethyl-N-ethoxalyltetrahydroquinoline (56.0 g, 0.146 mol) in dichloromethane (500 mL) was added dropwise to a suspension of nitronium tetrafluoroborate (25.0 g, 0.179 mol) in dichloromethane (500 mL) at 0° C. The mixture was stirred for 3 h at 0° C., poured into ice-water and extracted with dichloromethane. The organic layer was washed with brine, dried over magnesium sulfate, and concentrated. The residue was purified by silica gel column chromatography with 3:1 to 2:1 hexane/ethyl acetate to give 52.0 g of the title compound (83%).

$^1$H NMR (270 MHz, CDCl$_3$) δ8.11 and 7.99 (d and d, 1H, J=2 Hz), 7.66 and 7.61 (d and d, 1H, J=2 Hz), 5.03~5.16 and 4.74~4.85 (m and m, 1H), 4.37~4.49 and 4.13 (m and q, 2H, J=7.2 Hz), 3.72 and 3.62 (s and s, 3H), 2.44~3.02 (m, 5H), 1.65~1.80 and 1.50~1.60 (m and m, 1H), 1.42 and 1.23 (t and t, 3H, J=7.2 and 7.2 Hz).

7) 9-Bromo-5-methoxycarbonylmethyl-6,7-dihydro-1H, 5H-pyrido[1,2,3-de]quinoxaline-2,3-dione To a mixture of 20% aqueous titanium trichloride (670 g, 0.867 mol), water (500 mL), and acetone (500 mL) was added dropwise a solution of 6-bromo-2-methoxycarbonylmethyl-8-nitro-N-ethoxalyltetrahydroquinoline (52.0 g, 0.121 mol) in acetone (600 mL) at 0° C. The mixture was stirred overnight at room temperature, concentrated to ca. 1 L and diluted with water (1 L). The precipitates formed were collected by filtration, washed with water, and dried in vacuo to give 35.2 g of the title compound. The filtrate was extracted with ethyl acetate. The organic layer was washed with brine, dried over magnesium sulfate, and concentrated. The residue was purified by silica gel column chromatography with ethyl acetate to give 6.0 g of the title compound (total 89%).

mp 185°~187° C.

$^1$H NMR (270 MHz, DMSO-d$_6$) δ12.04 (bs, 1H), 7.20 (d, 1H, J=2 Hz), 7.15 (d, 1H, J=2 Hz), 5.04~5.13 (m, 1H), 3.62 (s, 3H), 2.94 (ddd, 1H, J=17.1, 13.5, 4.5 Hz), 2.78 (dm, 1 H, J=17.1 Hz), 2.63 (dd, 1H, J=18, 7.2 Hz), 2.57 (dd, 1H, J=18, 3.6 Hz), 2.09 (dm, 1H, J=13.5 Hz), 1.80~1.95 (m, 1H).

8) 9-Bromo-5-carboxymethyl-6,7-dihydro-1H, 5H-pyrido[1,2,3-de]quinoxaline-2,3-dione To a solution of 9-bromo-5-methoxycarbonylmethyl-6,7-dihydro-1H, 5H-pyrido[1,2,3-de]quinoxaline-2,3-dione (25.0 g, 0.071 mol) in a mixture of THF (350 mL) and methanol (350 mL) was added aqueous 1N NaOH (440 mL). The mixture was stirred for 2 h at room temperature, concentrated to ca. 500 mL, and acidified by addition of aqueous 1N HCl. The precipitates formed were collected by filtration, washed with distilled water, and dried in vacuo to give 22.9 g of the title compound (95%).

mp>270° C.

$^1$H NMR (270 MHz, DMSO-d$_6$) δ12.06 (bs, 1H), 7.20 (d, 1H, J=2 Hz), 7.15 (d, 1H, J=2 Hz), 5.02~5.12 (m, 1H), 2.95 (ddd, 1H, J=17.1, 13.5, 4.5 Hz), 2.79 (dm, 1H, J=17.1 Hz), 2.43~2.61 (m, 2H), 2.12 (dm, 1H, J=13.5 Hz), 1.78~1.96 (m, 1H).

Reference Example 2

9-Chloro-5-carboxymethyl-6,7-dihydro-1H, 5-pyrido[1,2,3-de]quinoxaline-2,3-dione 1) 9-Chloro-5-methoxycarbonylmethyl-6,7-dihydro-1H, 5H-pyrido[1,2,3-de]quinoxaline-2,3-dione A mixture of 9-bromo-5-methoxycarbonylmethyl-6,7-dihydro-1H, 5H-pyrido[1,2,3-de]quinoxaline-2,3-dione (530 mg, 1.50 mmol) and cuprous chloride (1.0 g, 10.1 mmol) in dimethyl sulfoxide (5 mL) was heated at 160° C. for 4.5 h and poured into 1N aqueous ammonium chloride (200 mL). The mixture was extracted with a mixed solvent of THF and ethyl acetate (600 mL). The extract was washed with 1N aqueous ammonium chloride (200 mL×2) and brine (200 mL), dried over magnesium sulfate, and concentrated. The residue was recrystallized from ethanol to give 125 mg of the title compound (27%).

mp 218~220° C. (dec)

$^1$H NMR (270 MHz, DMSO-d$_6$) δ12.08 (bs, 1H), 7.08 (d, 1H, J=2 Hz), 7.02 (d, 1H, J=2 Hz), 5.04~5.13 (m, 1H), 3.62 (s, 3H), 2.94 (ddd, 1H, J=17.1, 13.5, 4.5 Hz), 2.78 (dm, 1H, J=17.1 Hz), 2.63 (dd, 1H, J=18, 7.2 Hz), 2.57 (dd, 1H, J=18, 3.6 Hz), 2.09 (dm, 1H, J=13.5 Hz), 1.80~1.95 (m, 1H).

2) 9-Chloro-5-carboxymethyl-6,7-dihydro-1H, 5H-pyrido[1,2,3-de]quinoxaline- 2,3-dione Hydrolysis of 9-chloro-5-methoxycarbonylmethyl-6,7-dihydro-1H, 5H-pyrido[1,2,3-de]quinoxaline-2,3-dione (246 mg, 0.8 mmol) was carried out as described in Reference Example 1–8) to give 210 mg of the title compound (89%).

mp>280° C.

$^1$H NMR (270 MHz, DMSO-d$_6$) δ12.06 (bs, 1H), 7.08 (d, 1H, J=2 Hz), 7.02 (d, 1H, J=2 Hz), 5.02~5.13 (m, 1H), 2.95 (ddd, 1H, J=17.1, 13.5, 4.5 Hz), 2.78 (dm, 1H, J=17.1 Hz), 2.41~2.60 (m, 2H), 2.14 (dm, 1H, J=13.5 Hz), 1.88~1.95 (m, 1H).

EXAMPLE 1

(S)-9-Chloro-5-[p-tert-butoxycarbonylaminomethyl-o-(methoxycarbonyl)phenylcarbamoylmethyl]-6,7-dihydro-1H, 5H-pyrido[1,2,3-de]quinoxaline-2,3-dione

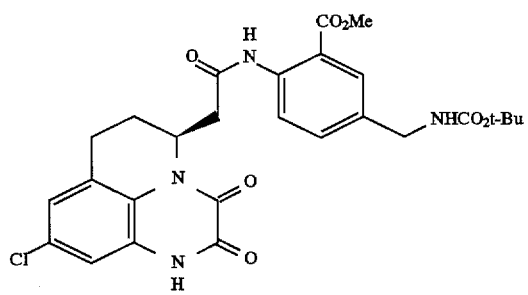

1) (S)-9-Chloro-5-carboxymethyl-6,7-dihydro-1H, 5H-pyrido[1,2,3-de]quinoxaline-2,3-dione The title compound was prepared starting from (S)-2-methoxycarbonyltetrahydroquinoline ($[\alpha]_D$=+41.4°) according to the method described in Reference Example 1 and 2. $[\alpha]_D$=−126.1 (c=0.1, MeOH).

2) Methyl 5-azidomethyl-2-nitrobenzoate

A mixture of methyl 5-methyl-2-nitrobenzoate (5.5 g, 30 mmol), N-bromosuccinimide (NBS, 5.87 g, 33 mmol), and azobisisobutyronitrile (AIBN, 200 mg) in carbon tetrachloride (60 mL) was refluxed for 3 h. The insoluble material formed was removed by filtration and the filtrate was concentrated. The residue was dissolved in DMF (10 mL) and sodium azide (2.92 g, 45 mmol) was added. The mixture was stirred for 2 h at 50° C., poured into brine, and extracted with a 1:1 mixture of toluene and ethyl acetate. The organic layers were washed with brine, dried over magnesium sulfate, and concentrated. The residue was purified by silica gel column chromatography with 4:1 hexane/ethyl acetate to give 3.97 g of the title compound (56%).

$^1$H NMR (CDCl$_3$) δ7.95 (d, 1H, J=8.1 Hz), 7.69 (d, 1H, J=2 Hz), 7.57 (dd, 1H, J=8.1, 2 Hz), 4.52 (s, 2H), 3.96 (s, 3H).

3) Methyl 5-tert-butoxycarbonylaminomethylanthranylate

A solution of methyl 5-azidomethyl-2-nitrobenzoate (8.19 g, 34.7 mmol) in ethyl acetate (300 mL) in the presence of di-tert-butyl dicarbonate (8.3 g, 38.1 mmol) and 10% Pd/C (1 g) was hydrogenated for 10 h under atmospheric pressure of hydrogen at room temperature. The catalyst was removed by filtration through celite and the filtrate was concentrated. The residue was purified by silica gel column chromatography with 4:1 hexane/ethyl acetate to give 6.5 g of the title compound (67%).

$^1$H NMR (CDCl$_3$) δ7.75 (d, 1H, J=2 Hz), 7.21 (dd, 1H, J=8.1,2 Hz), 6.64 (d, 1H, J=8.1 Hz), 5.64~5.76 (br, 2H), 4.66~4.72 (br, 1H), 4.17 (bd, 2H, J=6.3 Hz), 3.88 (s, 3H), 1.47 (s, 9H).

4) (S)-9-Chloro-5-[p-tert-butoxycarbonylaminomethyl-o-(methoxycarbonyl)phenylcarbamoylmethyl]-6,7-dihydro-1H, 5H-pyrido[1,2,3-de]quinoxaline-2,3-dione A mixture of methyl 5-tert-butoxycarbonylaminomethylanthranylate (802 mg, 2.85 mmol), (S)-9-chloro-5-carboxymethyl-6,7-dihydro-1H, 5H-pyrido[1,2,3-de]quinoxaline-2,3-dione (756 mg, 2.57 mmol), triethylamine (0.86 mL, 6.16 mmol), and N,N-bis(2-oxo-3-oxazolidinyl)-phosphinic chloride (Bop-Cl, 726 mg, 2.85 mmol) in dichloromethane (8 mL) was stirred for 3.5 h at room temperature. Bop-Cl (726 mg) was added and the mixture was stirred further for 2 h. The mixture was diluted with ethyl acetate (800 mL). The mixture was washed with 5% potassium hydrogen sulfate, water, 1/15 phosphate buffer (pH 7.5), water, and brine, successively, dried over magnesium sulfate, and concentrated. The residue was recrystallized from acetone-ethyl acetate to give 445 mg of the title compound. The mother liquid was concentrated and the residue was purified by silica gel column chromatography with ethyl acetate to 100% THF to give additionally 63 mg of the title compound (36%).

$^1$H NMR (DMSO-d6) δ12.0~12.5 (br, 1H), 10.46 (s, 1H), 8.03 (d, 1H, J=8.6 Hz), 7.75 (d, 1H, J=2 Hz), 7.45 (bt, 1H, J=5.9 Hz), 7.45 (dd, 1H, J=8.6, 2 Hz), 7.11 (d, 1H, J=2 Hz), 7.04 (d, 1H, J=2 Hz), 5.18 (m, 1H), 4.11 (d, 2H, J =5.9 Hz), 3.84 (s, 3H), 3.0~3.15 (m, 1H), 2.83 (dm, 1H, J=17.1 Hz), 2.60~2.78 (m, 2H), 2.17 (dm, 1H, J=14 Hz), 1.80~2.00 (m, 1H), 1.40 (s, 9H).

EXAMPLE 2

(S)-9-Chloro-5-(p-tert-butoxycarbonylaminomethyl-o-carboxyphenylcarbamoylmethyl)-6,7-dihydro-1H, 5H-pyrido[1,2,3-de]quinoxaline-2,3-dione A solution of (S)-9-chloro-5-[p-tert-butoxycarbonylaminomethyl-o-(methoxycarbonyl) phenylcarbamoylmethyl]-6,7-dihydro-1H, 5H-pyrido[1,2,3-de]quinoxaline-2,3-dione (445 mg) in a mixture of 1N sodium hydroxide (5 mL), THF (5 mL), and methanol (5 mL) was stirred for 3.5 h at room temperature and the solvent was concentrated to ca. 5 mL. To the residue was added 5% potassium hydrogen sulfate and the precipitates formed were collected by filtration, washed with water, and dried to give 453 mg of the title compound.

EXAMPLE 3

(S)-9-Chloro-5-(p-aminomethyl-o-carboxyphenylcarbamoylmethyl)-6,7-dihydro-1H, 5H-pyrido[1,2,3-de]quinoxaline-2,3-dione hydrochloride A suspension of (S)-9-chloro-5-(p-tert-butoxycarbonylaminomethyl-o-carboxyphenylcarbamoylmethyl)-6,7-dihydro-1H, 5H-pyrido[1,2,3-de]-quinoxaline-2,3-dione (430 mg) in 2N hydrogen chloride in 1,4-dioxane (14 mL) was stirred overnight at room temperature and diluted with diethyl ether. The precipitates were collected by filtration and recrystallized from water to give 350 mg of the title compound.

$^1$H NMR (DMSO-d6) δ12.0~13.0 (br, 1H), 12.12 (bs, 1H), 11.06 (bs, 1H), 8.36 (d, 1H, J=8.6 Hz), 8.20~8.40 (br, 3H), 8.10 (d, 1H, J=2.3 Hz), 7.69 (dd, 1H, J=8.6, 2.3 Hz), 7.10 (d, 1H, J=2.3 Hz), 7.07 (d, 1H, J=2.3 Hz), 5.20 (m, 1H), 4.03 (bd, 2H, J=6.6 Hz), 3.00~3.15 (m, 1H), 2.78~2.90 (dm, 1H, J=14.0 Hz), 2.71 (bd, 2H, J=7.3 Hz), 2.15~2.28 (dm, 1H, J=14.0 Hz), 1.82~2.00 (m, 1H).

EXAMPLE 4

(S)-9-Bromo-5-[p-tert-butoxycarbonylaminomethyl-o-(methoxycarbonyl)phenylcarbamoylmethyl]- 6,7-dihydro-1H, 5H-pyrido[1,2,3-de]quinoxaline-2,3-dione 1) (S)-9-Bromo-5-carboxymethyl-6,7-dihydro-1H, 5H-pyrido[1,2,3-de]quinoxaline-2,3-dione The title compound was prepared starting from (S)-2-methoxycarbonyltetrahydroquinoline ($[\alpha]_D$=+41.4°) according to the method described in Reference Example 1. $[\alpha]_D$=−108.3° (c=0.1, MeOH).

2) (S)-9-Bromo-5-[p-tert-butoxycarbonylaminomethyl-o-(methoxycarbonyl)phenylcarbamoylmethyl]-6,7-dihydro-1H, 5H-pyrido[1,2,3-de]quinoxaline-2,3-dione A procedure similar to that described in Example 1-4) was performed with (S)-9-bromo-5-carboxymethyl-6,7-dihydro-1H, 5H-pyrido[1,2,3-de]quinoxaline-2,3-dione (760 mg, 2.24 mmol) and methyl 5-tert-butoxycarbonylaminomethylanthranylate (700 mg, 2.49 mmol) to give 640 mg of the title compound (48%).

$^1$H NMR (DMSO-d6) δ12.06 (bs, 1H), 10.44 (s, 1H), 8.01 (d, 1H, J=8.1 Hz), 7.76 (d, 1H, J=2 Hz), 7.42~7.50 (m, 2H), 7.24 (d, 1H, J=2 Hz), 7.17 (d, 1H, J=2 Hz), 5.11~5.27 (m, 1H), 4.12 (d, 2H, J=6.3 Hz), 3.84 (s, 3H), 3.05 (ddd, 1H, J=17.1, 13.5, 4.5 Hz), 2.83 (dm, 1H, J=17.1 Hz), 2.60~2.76 (m, 2H), 2.17 (dm, 1H, J=13.5 Hz), 1.78~1.97 (m, 1H), 1.39 (s, 9H).

EXAMPLE 5

(S)-9-Bromo-5-(p-tert-butoxycarbonylaminomethyl-o-carboxyphenylcarbamoylmethyl)-6,7-dihydro-1H, 5H-pyrido[1,2,3-de]quinoxaline-2,3-dione A solution of (S)-9-bromo-5-[p-tert-butoxycarbonylaminomethyl-o-(methoxycarbonyl)

phenylcarbamoylmethyl]-6,7-dihydro-1H, 5H-pyrido[1,2,3-de]quinoxaline-2,3-dione (680 mg, 1.06 mmol) in a mixture of 1N sodium hydroxide (6 mL), THF (6 mL), and methanol (6 mL) was stirred for 3.5 h at room temperature and the solvent was concentrated to ca. 6 mL. To the residue was added 5% potassium hydrogen sulfate and extracted with ethyl acetate. The organic layer was washed with water, dried over magnesium sulfate, and concentrated to give 608 mg of the title compound.

$^1$H NMR (DMSO-d6) δ12.06 (bs, 1H), 11.93 (s, 1H), 8.31 (d, 1H, J=8.6 Hz), 7.85 (d, 1H, J=2 Hz), 7.30~7.46 (m, 2H), 7.10~7.30 (m, 4H), 7.17 (d, 1H, J =2 Hz), 5.11~5.27 (m, 1H), 4.08 (d, 2H, J=6.3 Hz), 3.05 (ddd, 1H, J=17.1, 13.5, 4.5 Hz), 2.80 (dm, 1H, J=17.1 Hz), 2.60~2.76 (m, 2H), 2.17 (dm, 1H, J =13.5 Hz), 1.78~1.97 (m, 1H), 1.39 (s, 9H).

EXAMPLE 6

(S)-9-Bromo-5-(p-aminomethyl-o-carboxyphenylcarbamoylmethyl)-6,7-dihydro-1H, 5H-pyrido[1,2,3-de]quinoxaline-2,3-dione hydrochloride A procedure similar to that described in Example 3 was performed with (S)-9-bromo-5-(p-tert-butoxycarbonylaminomethyl-o-carboxyphenylcarbamoylmethyl)-6,7-dihydro-1H, 5H-pyrido[1,2,3-de]quinoxaline-2,3-dione (350 mg) to give 275 mg of the title compound.

$^1$H NMR (CD$_3$OD) δ8.58 (d, 1H, J=8.1 Hz), 8.20 (d, 1H, J=2 Hz), 7.64 (dd, 1H, J=8.1,2 Hz), 7.24 (bs, 1H), 7.22 (bs, 1H), 5.35~5.46 (m, 1H), 4.13 (s, 2H), 3.15 (ddd, 1H, J=17.1, 13.5, 4.5 Hz), 2.92 (dm, 1H, J=17.1 Hz), 2.84 (dd, 1H, J=6.3, 13.5 Hz), 2.75 (dd, 1H, J=8.1, 13.5 Hz), 2.34 (dm, 1H, J=13.5 Hz), 1.97~2.15 (m, 1H). [α]$_D$=−37.6° (c=0.1, MeOH).

EXAMPLE 7

(±)-9-Bromo-5-[p-tert-butoxycarbonylaminomethyl-o-(methoxycarbonyl)phenylcarbamoylmethyl]-6,7-dihydro-1H, 5H-pyrido[1,2,3-de]quinoxaline-2,3-dione The title compound was prepared from (±)-9-bromo-5-carboxymethyl-6,7-dihydro-1H, 5H-pyrido[1,2,3-de]quinoxaline-2,3-dione (300 mg, 1.17 mmol) and methyl 5-tert-butoxycarbonylaminomethylanthranylate (361 mg, 1.28 mmol) according to a method described in Example 1-4.

EXAMPLE 8

(±)-9-Bromo-5-[p-aminomethyl-o-(methoxycarbonyl)phenylcarbamoylmethyl]-6,7-dihydro-1H, 5H-pyrido[1,2,3-de]quinoxaline-2,3-dione A procedure similar to that described in Example 3 was performed with (±)-9-bromo-5-[p-tert-butoxycarbonylaminomethyl-o-(methoxycarbonyl)phenylcarbamoylmethyl]-6,7-dihydro-1H, 5H-pyrido[1,2,3-de]quinoxaline-2,3-dione (35 mg) to give 31 mg of the title compound (89%).

$^1$H NMR (CD$_3$OD) δ8.50 (d, 1H, J=8.1 Hz), 8.16 (d, 1H, J=2 Hz), 7.66 (dd, 1 H, J=2, 8.1 Hz), 7.25 (bs, 1H), 7.23 (bs, 1H), 5.37~5.47 (m, 1H), 4.16 (s, 2H), 3.95 (s, 3H), 3.16 (ddd, 1H, J=17.1, 13.5, 4.5 Hz), 2.91 (dm, 1H, J=17.1 Hz), 2.86 (dd, 1H, J=6.3, 13.5 Hz), 2.75 (dd, 1H, J=8.1, 13.5 Hz), 2.39 (dm, 1H, J=13.5 Hz), 1.99~2.14 (m, 1H).

EXAMPLE 9

(S)-9-Chloro-5-[p-tert-butoxycarbonylaminomethyl-o-(methoxycarbonylmethyl)phenylcarbamoylmethyl]-6,7-dihydro-1H, 5H-pyrido[1,2,3-de]quinoxaline-2,3-dione

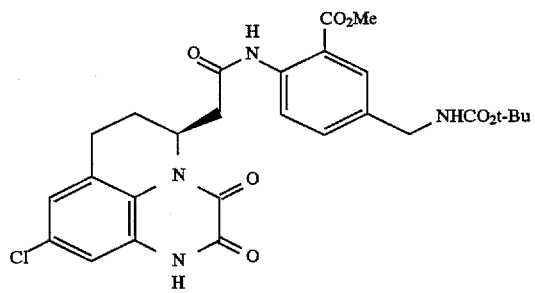

1) 4-Nitro-3-trifluoromethanesulfonyloxytoluene

To a solution of 3-methyl-6-nitrophenol (3.06 g, 20 mmol) and 2,4,6-colidine (4.0 mL, 30 mmol) in dichloromethane (100 mL) was added slowly trifluoromethanesulfonic anhydride (7.05 g, 25 mmol) at room temperature. The mixture was stirred overnight at the same temperature, poured into water, and extracted with ethyl acetate. The organic layer was washed successively with 0.2N hydrochloric acid, water, saturated aqueous sodium bicarbonate, and brine, dried over magnesium sulfate, and concentrated to give 5.0 g of the title compound (88%).

$^1$H NMR (CDCl$_3$) δ8.03 (d, 1H, J=8.3 Hz), 7.36 (d, 1H, J=8.3 Hz), 7.24 (s, 1H), 2.52 (s, 3H).

2) 1-Nitro-4-phthalimidomethyl-2-trifluoromethanesulfonyloxybenzene

A mixture of 4-nitro-3-trifluoromethanesulfonyloxytoluene (5.7 g, 20 mmol), N-bromosuccinimide (5.7 g, 32 mmol), and benzoyl peroxide (1 g) in carbon tetrachloride (75 mL) was refluxed for 18 h. The insoluble material formed was removed by filtration and the filtrate was concentrated. The residue was dissolved in DMF (40 mL) and potassium phthalimide (2.6 g, 14 mmol) was added. The mixture was stirred for 5 h at room temperature, poured into brine, and extracted with a 1:1 mixture of toluene and ethyl acetate. The organic layers were washed with brine, dried over magnesium sulfate, and concentrated. The residue was purified by silica gel column chromatography with 9:1 to 1:1 hexane/ethyl acetate to give 3.4 g of the title compound (39%).

$^1$H NMR (CDCl$_3$) δ8.14 (d, 1H, J=8.3 Hz), 7.86~7.91 (m, 2H), 7.75~7.79 (m, 2H), 7.63 (dd, 1H, J=8.3, 1.6 Hz), 7.54 (d, 1H, J=1.6 Hz), 4.93 (s, 2H).

3) Diethyl 2-nitro-5-phthalimidomethylphenylmalonate

To a suspension of 60% sodium hydride (5.8 g, 145 mmol) in DMF (150 mL) was added diethyl malonate (26.4 mL, 175 mmol) at room temperature, while the sodium hydride was washed with dry hexane before use. The mixture was heated at 40° C. for 1.5 h, allowed to cool at room temperature and 1-nitro-4-phthalimidomethyl-2-trifluoromethanesulfonyloxybenzene (25 g, 58 mmol) was added. The mixture was stirred overnight at room temperature, poured into 3% potassium hydrogen sulfate, and extracted with a 1:1 toluene/ethyl acetate. The extract was washed successively with 5% potassium hydrogen sulfate, water, saturated aqueous sodium bicarbonate, and brine, dried over magnesium sulfate, and concentrated. The unreacted diethyl malonate was distilled out in vacuo and the residual solid was washed with 1:1 diethyl ether/hexane to give 24.5 g of the title compound.

¹H NMR (CDCl₃) δ8.04 (d, 1H, J=8.9 Hz), 7.85~7.90 (m, 2H), 7.72~7.78 (m, 2H), 7.56 (d, 1H, J=8.9 Hz), 7.54 (s, 1H), 5.24 (s, 1H), 4.90 (s, 2H), 4.27 (q, 4H, J=7.3 Hz), 1.28 (t, 6H, J=7.3 Hz).

4) Methyl 5-aminomethyl-2-nitrophenylacetate hydrochloride

A solution of diethyl 2-nitro-5-phthalimidomethylphenylmalonate in a mixture of concentrated hydrochloric acid (150 mL) and 1,4-dioxane (150 mL) was heated at 120° C. for 24 h. The solvents was removed in vacuo and the residual solid was dissolved in methanol (100 mL). To the solution was added thionyl chloride (11.8 g) dropwise at 0° C. The mixture was stirred for 2 h at 40° C. and the solvent and the excess reagent was removed in vacuo. The residue was washed with diethyl ether and dried to give 6.5 g of the title compound (quant).

¹H NMR (CD₃OD) δ8.18 (d, 1H, J=8.6 Hz), 7.63 (dd, 1H, J=8.6, 1.6 Hz), 7.56 (d, 1H, J=1.6 Hz), 4.23 (s, 2H), 4.09 (s, 2H), 3.69 (s, 3H).

5) Methyl 5-tert-butoxycarbonylaminomethyl-2-nitrophenylacetate

To a solution of methyl 5-aminomethyl-2-nitrophenylacetate hydrochloride (6.80 g, 26.1 mmol) and triethylamine (12 mL) in dichloromethane (100 mL) was added di-tert-butyl dicarbonate (9 mL, 39.2 mmol) at room temperature. The mixture was stirred for 1.5 h and diluted with ethyl acetate. The mixture was washed successively with 5% potassium hydrogen sulfate, water, saturated aqueous sodium bicarbonate, and brine, dried over magnesium sulfate, and concentrated. The residue was purified by silica gel column chromatography with 6:1 to 2:1 hexane/ethyl acetate to give 8.55 g of the title compound (quant).

¹H NMR (CDCl₃) δ8.11 (d, 1H, J'8.3 Hz), 7.38 (d, 1H, J=8.3 Hz), 7.25 (s, 1H), 4.98 (br, 1H), 4.39 (d, 2H, J=6.3 Hz), 4.02 (s, 2H), 1.49 (s, 9H).

6) 4-tert-Butoxycarbonylaminomethyl-2-methoxycarbonylmethylaniline

A solution of methyl 5-tert-butoxycarbonylaminomethyl-2-nitrophenylacetate (6.8 g, 21 mmol) in methanol (250 mL) in the presence of 10% Pd/C was hydrogenated under atmospheric pressure of hydrogen at room temperature. The catalyst was removed by filtration through celite and the filtrate was concentrated to give 5.8 g of the title compound.

¹H NMR (CDCl₃) δ7.02 (d, 1H, J=7.6 Hz), 7.00 (s, 1H), 6.67 (d, 1H, J=7.6 Hz), 4.72 (br, 1H), 4.18 (d, 2H, J=5.7 Hz), 4.05 (br, 2H), 3.55 (s, 2H), 1.46 (s, 9H).

7) (S)-9-Chloro-5-[p-tert-butoxycarbonylaminomethyl-o-(methoxycarbonylmethyl)phenylcarbamoylmethyl]-6,7-dihydro-1H, 5H-pyrido[1,2,3-de]-quinoxaline-2,3-dione A mixture of methyl 4-tert-butoxycarbonylaminomethyl-2-methoxycarbonylmethylaniline (1.20 g, 4.27 mmol), (S)-9-chloro-5-carboxymethyl-6,7-dihydro-1H, 5H-pyrido[1,2,3-de]quinoxaline-2,3-dione (1.26 g, 4.27 mmol), triethylamine (1.49 mL, 10.7 mmol), and Bop-Cl (1.19 g, 4.69 mmol) in dichloromethane (26 mL) was stirred for 4.5 h at 0° C. to room temperature and diluted with ethyl acetate. The mixture was washed successively with 5% potassium hydrogen sulfate, water, 1/15 phosphate buffer (pH 7.5), water, and brine, dried over magnesium sulfate, and concentrated. The residual solid was washed with a 1:1 mixture of diethyl ether and dichloromethane, and dried to give 1.82 g of the title compound (74%).

¹H NMR (DMSO-d6) δ12.06 (s, 1H), 9.48 (s, 1H), 7.39 (t, 1H, J=7.2 Hz), 7.26 (d, 1H, J=9.0 Hz), 7.15~7.05 (m, 3H), 7.04 (bs, 1H), 5.26~5.14 (m, 1H), 4.08 (d, 2H, J=7.2 Hz), 3.66 (s, 2H), 3.57 (s, 3H), 3.06 (ddd, 1H, J=17.1, 13.5, 4.5 Hz), 2.83 (dm, 1H, J=17.1 Hz), 2.66~2.52 (m, 2H), 2.11 (dm, 1H, J=13.5 Hz), 1.97~1.77 (m, 1H), 1.41 (s, 9H).

EXAMPLE 10

(S)-9-Chloro-5-[p-tert-butoxycarbonylaminomethyl-o-(carboxymethyl)phenylcarbamoylmethyl]-6,7-dihydro-1H, 5H-pyrido[1,2,3-de]quinoxaline-2,3-dione A solution of (S)-9-chloro-5-[p-tert-butoxycarbonylaminomethyl-o-(methoxycarbonylmethyl)phenylcarbamoylmethyl]-6,7-dihydro-1H, 5H -pyrido[1,2, 3-de]quinoxaline-2,3-dione (1.82 g, 3.18 mmol) in a mixture of 1N aqueous sodium sulfate (20 mL), THF (20 mL), and methanol (20 mL) was stirred for 4 h at room temperature. The mixture was acidified to pH 3 by addition of 5% potassium hydrogen sulfate and extracted with a 1:1 mixture of ethyl acetate and THF. The organic layers were washed with brine, dried over magnesium sulfate, and concentrated. The residual solid was washed with dichloromethane, and dried in vacuo to give 1.499 g of the title compound.

EXAMPLE 11

(S)-9-Chloro-5-[p-aminomethyl-o-(carboxymethyl)phenylcarbamoylmethyl]-6,7-dihydro-1H, 5H-pyrido[1,2,3-de]quinoxaline-2,3-dione hydrochloride A suspension of (S)-9-chloro-5-[p-tert-butoxycarbonylaminomethyl-o-(carboxymethyl)phenylcarbamoylmethyl]-6,7-dihydro-1H, 5H-pyrido[1,2,3-de]quinoxaline-2,3-dione (1.499 g) in 2N hydrogen chloride in 1,4-dioxane (30 mL) was stirred overnight at room temperature and diluted with diethyl ether. The precipitates were collected and recrystallized from water to give 1.247 g of the title compound (79%).

¹H NMR (DMSO-d6) δ12.40 (bs, 1H), 12.12 (s, 1H), 9.63 (s, 1H), 8.25 (br, 3H), 7.46 (d, 1H, J=9 Hz), 7.36 (d, 1H, J=9.0 Hz), 7.34 (s, 1H), 7.13 (s, 1H), 7.06 (s, 1H), 5.28~5.14 (m, 1H), 4.05~3.93 (m, 2H), 3.64 (d, 1H, J=16 Hz), 3.62 (d, 1H, J=16 Hz), 3.08 (ddd, 1H, J=17.1, 13.5, 4.5 Hz), 2.82 (dm, 1H, J=17.1 Hz), 2.72~2.55 (m, 2H), 2.11 (dm, 1H, J=17.1 Hz), 1.96~1.76 (m, 1H).

EXAMPLE 12

(S)-9-Bromo-5-[p-tert-butoxycarbonylaminomethyl-o-(methoxycarbonylmethyl)phenylcarbamoylmethyl]-6,7-dihydro-1H, 5H-pyrido[1,2,3-de]quinoxaline-2,3-dione A procedure similar to that described in Example 9–7) was performed with methyl 4-tert-butoxycarbonylaminomethyl-2-methoxycarbonylmethylaniline (7.63 g, 22.51 mmol) and (S)-9-bromo-5-carboxymethyl-6,7-dihydro-1H, 5H-pyrido[1,2,3-de]quinoxaline-2,3-dione (6.03 g, 21.43 mmol) to give 8.02 g of the title compound (61%).

¹H NMR (DMSO-d6) δ12.06 (bs, 1H), 9.48 (s, 1H), 8.01 (d, 1H, J=8.1 Hz), 7.38 (t, 1H, J=7.2 Hz), 7.20~7.30 (m, 2H), 7.09~7.20 (m, 3H), 5.13~5.23 (m, 1H), 4.08 (d, 2H, J=7.2 Hz), 3.67 (s, 2H), 3.60 (s, 3H), 2.97~3.14 (m, 1H), 2.82 (dm, 1H, J=17.1 Hz), 2.56~2.64 (m, 2H), 2.04~2.14 (m, 1H), 1.79~1.93 (m, 1H).

EXAMPLE 13

(S)-9-Bromo-5-[p-tert-butoxycarbonylaminomethyl-o-(carboxymethyl)phenylcarbamoylmethyl]-6,7-dihydro-1H, 5H-pyrido[1,2,3-de]quinoxaline-2,3-dione A procedure similar to that described in Example 10 was performed with (S)-9-bromo-5-[p-tertbutoxycarbonylaminomethyl-o-(methoxycarbonylmethyl) phenylcarbamoylmethyl]-6,7-dihydro-1H, 5H-pyrido[1,2,3-de]quinoxaline-2,3-dione (8.02 g, 13.03 mmol) to give 6.52 g of the title compound.

EXAMPLE 14

(S)-9-Bromo-5-[p-aminomethyl-o-(carboxymethyl) phenylcarbamoylmethyl]-6,7-dihydro-1H, 5H-pyrido[1,2,3-de]quinoxaline-2,3-dione hydrochloride A procedure similar to that described in Example 11 was performed with (S)-9-bromo-5-[p-tert-butoxycarbonylaminomethyl-o-(carboxymethyl) phenylcarbamoylmethyl]-6,7-dihydro-1H, 5H-pyrido[1,2,3-de]quinoxaline-2,3-dione (6.5 g) to give 5.438 g of the title compound (80%).

$^1$H NMR (CD$_3$OD) δ7.54 (d, 1H, J=9 Hz), 7.40 (bs, 1H), 7.37 (bd, 1H, J=9 Hz), 7.25 (bs, 1H), 7.22 (bs, 1H), 5.38~5.50 (m, 1H), 4.11 (s, 2H), 3.71 (s, 2 H), 3.16 (ddd, 1H, J=17.1, 13.5, 4.5 Hz), 2.91 (dm, 1H, J=17.1 Hz), 2.79 (dd, 1H, J=5.4, 13.5 Hz), 2.71 (dd, 1H, J=8.1, 13.5 Hz), 2.34 (dm, 1H, J=13.5 Hz), 1.95~2.12 (m, 1H). [α]$_D$=−60.0° (c=0.1, MeOH).

EXAMPLE 15

(±)-9-Bromo-5-[p-(2,3-di-tert-butoxycarbonylguanidinomethyl)-o-(methoxycarbonylmethyl)phenylcarbamoylmethyl]-6,7-dihydro-1H, 5H-pyrido[1,2,3-de]quinoxaline-2,3-dione

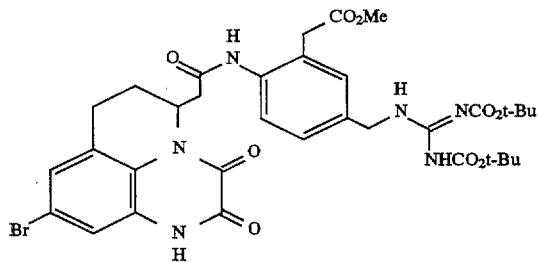

1) Methyl 3-(2,3-di-tert-butoxycarbonylguanidinomethyl)-6-nitrophenylacetate

A solution of methyl 3-(aminomethyl)-6-nitrophenylacetate hydrochloride (652 mg, 2.5 mmol), 1,3-di-tert-butoxycarbonyl-2-methylisothiourea (850 mg, 2.9 mmol), and triethylamine (708 mg, 7.9 mmol) in DMF (10 mL) was stirred for 7 h at 50°~55° C. The mixture was diluted with water and extracted with a 1:1 mixture of toluene/ethyl acetate. The organic layer was washed with brine, dried over magnesium sulfate, and concentrated. The residue was purified with silica gel column chromatography with 6:1 to 4:1 hexane/ethyl acetate to give 705 mg of the title compound (65%).

$^1$H NMR (CDCl$_3$) δ11.54 (bs, 1H), 8.74 (bt, 1H, J=5.6 Hz), 8.12 (d, 1H, J=8.6 Hz), 7.41 (dd, 1H, J=8.6, 1.7 Hz), 7.27 (d, 1H, J=1.7 Hz), 4.72 (d, 1H, J=5.6 Hz), 4.03 (s, 2H), 3.72 (s, 3H), 1.50 (s, 18H).

2) 4-(2,3-Di-tert-butoxycarbonylguanidinomethyl)-2-methoxycarbonylmethylaniline

A procedure similar to that described in Example 9–6) was performed with methyl 3-(2,3-di-tert-butoxycarbonylguanidinomethyl)-6-nitrophenylacetate (400 mg, 0.92 mmol) to give 362 mg of the title compound (97%).

3) (±)-9-Bromo-5-[p-(2,3-di-tert-butoxycarbonylguanidinomethyl)-o-(methoxycarbonylmethyl)phenylcarbamoylmethyl]-6,7-dihydro-1H, 5H-pyrido[1,2,3-de]quinoxaline- 2,3-dione A procedure similar to that described in Example 9–7) was performed with 4-(2,3-di-tert-butoxycarbonylguanidinomethyl)-2-methoxycarbonylmethylaniline (220 mg, 0.54 mmol) and (±)-9-Bromo-5-carboxymethyl-6,7-dihydro-1H, 5H-pyrido [1,2,3-de]quinoxaline-2,3-dione (190 mg, 0.56 mmol) to give 185 mg of the title compound after silica gel column chromatography with 0.3% acetic acid/ethyl acetate (47%).

$^1$H NMR (DMSO-d6) δ12.07 (br, 1H), 11.53 (br, 1H), 9.50 (br, 1H), 8.66 (bt, 1H, J=5.9 Hz), 7.32 (d, 1H, J=8.6 Hz), 7.13~7.28 (m, 4H), 5.13~5.28 (m, 1H), 4.48 (bd, 2H, J=8.6 Hz), 3.68 (bs, 2H), 3.59 (s, 3H), 3.00~3.18 (m, 1H), 2.78~2.89 (dm, 1H, J=14.0 Hz), 2.59 (bd, 2H, J=7.3 Hz), 2.05~2.17 (dm, 1H, J=14.0 Hz), 1.79~1.95 (m, 1H), 1.48 (s, 9H), 1.39 (s, 9H).

EXAMPLE 16

(±)-9-Bromo-5-[p-(2,3-di-tert-butoxycarbonylguanidinomethyl)-o-(carboxymethyl) phenylcarbamoylmethyl]-6,7-dihydro-1H, 5H-pyrido[1,2,3-de]quinoxaline-2,3-dione A procedure similar to that described in Example 10 was performed with (±)-9-Bromo-5-[p-(2,3-di-tert-butoxycarbonylguanidinomethyl)-o-(methoxycarbonylmethyl)phenylcarbamoylmethyl]-6,7-dihydro-1H, 5H-pyrido[1,2,3-de]quinoxaline-2,3-dione (160 mg, 0.22 mmol) to give 129 mg of the title compound (82%).

EXAMPLE 17

(±)-9-Bromo-5-[p-guanidinomethyl-o-(carboxymethyl)phenylcarbamoylmethyl]-6,7-dihydro-1H, 5H-pyrido[1,2,3-de]quinoxaline-2,3-dione A procedure similar to that described in Example 11 was performed with (±)-9-bromo-5-[p-(2,3-di-tert-butoxycarbonylguanidinomethyl)-o-(methoxycarbonylmethyl)phenylcarbamoylmethyl]-6,7-dihydro-1H, 5H-pyrido[1,2,3-de]quinoxaline-2,3-dione (125 mg, 0.176 mmol) to give 88 mg of the title compound (90%).

$^1$H NMR (DMSO-d6) δ12.09 (bs, 1H), 9.55 (bs, 1H), 7.93 (bt, 1H, J=5.9 Hz), 7.41 (d, 1H, J=8.9 Hz), 7.05~7.39 (m, 8H), 5.18~5.27 (m, 1H), 4.33 (bd, 2H, J=5.9 Hz), 3.61 (d, 2H, J=2.6 Hz), 3.00~3.18 (m, 1H), 2.77~2.90 (dm, 1 H, J=14 Hz), 1.78~1.95 (m, 1H).

EXAMPLE 18

(S)-9-Chloro-5-[p-tert-butoxycarbonylaminomethyl-o-(2-methoxycarbonylethyl) phenylcarbamoylmethyl]-6,7-dihydro-1H, 5H-pyrido[1,2,3-de]quinoxaline-2,3-dione 1) 3-Methyl-2-nitrobenzylalcohol To a refluxed solution of methyl 5-methyl-2-nitrobenzoate (50 g, 0.256 mol) and sodium borohydride (29 g, 0.768 mol) in THF (400 mL) was added dropwise methanol (60 mL) over 2.5 h. After the addition was completed, the mixture was refluxed for 1 h and allowed to cool at room temperature. The excess reagent was decomposed by addition of diluted hydrochloric acid (300 mL) and the mixture was extracted with ethyl acetate. The organic layer was washed with brine, dried over magnesium sulfate, and concentrated to give 43.0 g of the title compound (100%).

¹H NMR (CDCl₃) δ8.03 (d, 1H, J=8.6 Hz), 7.51 (s, 1H), 7.26 (d, 1H, J=8.6 Hz), 4.94 (bs, 2H), 2.63 (br, 1H), 2.47 (s, 3H).

2) Diethyl 3-methyl-6-nitrobenzylmalonate

A mixture of 3-methyl-2-nitrobenzylalcohol (30.0 g, 0.18 mol) and thionyl chloride (30 mL, 0.42 mol) in diethyl ether (200 mL) was refluxed for 4 h and concentrated. The residual reagent and hydrogen chloride was removed by azeotropic evaporation with toluene to give 37.0 g of the crude benzylic chloride. To a solution of sodium diethyl malonate (0.36 mol) prepared from diethyl malonate (0.46 mol) and 60% sodium hydride (14.5 g, 0.36 mol) in DMF (300 mL) was added the crude benzylic chloride (37 g) in toluene (60 mL) at room temperature. The mixture was stirred for 2 h at 5°~60° C., poured into 0.2N hydrochloric acid (1.5 L), and extracted with a 1:1 mixture of toluene and ethyl acetate. The organic layers were washed with brine, dried over magnesium sulfate, and concentrated. The residue was purified by silica gel column chromatography with toluene to 50:1 toluene/ethyl acetate to give 25.4 g of the title compound (46%).

¹H NMR (CDCl₃) δ7.95 (d, 1H, J=8.3 Hz), 7.19 (d, 1H, J=8.3 Hz), 7.17 (bs, 1H), 4.17 (q, 2H, J=7.3 Hz), 4.16 (q, 2H, J=7.3 Hz), 3.86 (t, 1H, J=7.6 Hz), 3.49 (d, 2H, J=7.6 Hz), 2.39 (s, 3H), 1.21 (t, 6H, J=7.3 Hz).

3) Diethyl 3-phthalimidomethyl-6-nitrobenzylmalonate

A mixture of diethyl 3-methyl-6-nitrobenzylmalonate (25.0 g, 80.8 mmol), N-bromosuccinimide (18.5 g, 103.9 mmol), and azobisisobutyronitrile (AIBN, 1.1 g) in carbon tetrachloride (400 mL) was refluxed for 11 h, while 3×100 mg of AIBN were added every 3 h during the reaction. The insoluble material formed was removed by filtration and the filtrate was concentrated. The residue was dissolved in DMF (100 mL) and potassium phthalimide (13.5 g, 72.9 mmol) was added. The mixture was stirred for 3 h at 5°~60° C., poured into saturated sodium bicarbonate, and extracted with a 1:1 mixture of toluene and ethyl acetate. The organic layers were washed with brine, dried over magnesium sulfate, and concentrated. The residue was purified by silica gel column chromatography with 4:1 hexane/ethyl acetate to give 18.66 g of the title compound (51%).

¹H NMR (CDCl₃) δ7.96 (d, 1H, J=8.3 Hz), 7.83~7.90 (m, 2H), 7.71~7.78 (m, 2H), 7.43 (dd, 1H, J=8.3, 2.0 Hz), 7.40 (d, 1H, J=2.0 Hz), 4.86 (s, 2H), 4.14 (q, 2H, J=7.3 Hz), 4.13 (q, 2H, J=7.3 Hz), 3.82 (t, 1H, J=7.6 Hz), 3.48 (d, 2H, J=7.6 Hz), 1.20 (t, 6H, J=7.3 Hz).

4) Methyl 3-(3-tert-butoxycarbonylaminomethyl-6-nitrophenyl)propionate

A solution of diethyl 3-phthalimidomethyl-6-nitrobenzylmalonate (18.0 g, 39.6 mmol) in a mixture of conc.hydrochloric acid (100 mL) and dioxane (100 mL) was refluxed for 30 h and concentrated. The residual water and hydrochloric acid were azeotropically distilled out with toluene. The residue was dissolved in methanol (250 mL) and thionyl chloride (50 mL) was added. The mixture was refluxed for 3 h and concentrated. The residual reagent and hydrogen chloride were azeotropically distilled out with toluene. The residue was dissolved in dichloromethane (10 mL) and di-tert-butyl dicarbonate (0.35 mL) and triethylamine (0.5 mL) were added. The mixture was stirred for 1 h at room temperature, diluted with ethyl acetate, and washed with 5% potassium hydrogen sulfate, water, saturated sodium bicarbonate, water, and brine, successively. The organic layer was dried over magnesium sulfate and concentrated. The residue was purified by silica gel column chromatography with 7:1 to 4:1 hexane/ethyl acetate to give 8.03 g of the title compound (60%).

¹H NMR (CDCl₃) δ7.94 (d, 1H, J=8.9 Hz), 7.29 (d, 1H, J=2.0 Hz), 7.28 (dd, 1H, J=8.9, 2.0 Hz), 4.90~5.10 (br, 1H), 4.36 (bd, 2H, J=5.9 Hz), 3.68 (s, 3H), 3.22 (t, 2H, J=7.6 Hz), 2.71 (t, 2H, J=7.6 Hz), 1.47 (s, 9H).

5) 2-(2-Methoxycarbonylethyl)-4-tert-butoxycarbonylaminomethylaniline

A solution of methyl 3-(3-tert-butoxycarbonylaminomethyl-6-nitrophenyl)propionate (3.2 g, 9.5 mmol) in ethyl acetate (35 mL) in the presence of 10% Pd/C was hydrogenated under atmospheric pressure of hydrogen at room temperature. The catalyst was removed by filtration by using celite and the filtrate was concentrated to give 3.4 g of the title compound.

¹H NMR (CDCl₃) δ6.95 (dd, 1H, J=8.3, 2.0 Hz), 6.94 (d, 1H, J=2.0 Hz), 6.40 (d, 1H, J=8.3 Hz), 4.70~4.80 (br, 1H), 4.17 (bd, 2H, J=5.3 Hz), 3.68 (s, 3H), 2.81 (t, 2H, J=7.3 Hz), 2.62 (t, 2H, J=7.3 Hz), 1.46 (s, 9H).

6) (S)-9-Chloro-5-[p-tert-butoxycarbonylaminomethyl-o-(2-methoxycarbonylethyl) phenylcarbamoylmethyl]-6,7-dihydro-1H, 5H-pyrido[1,2,3-de]quinoxaline-2,3-dione A mixture of 2-(2-methoxycarbonylethyl)-4-tert-butoxycarbonylaminomethylaniline (3.4 g), (S)-9-chloro-5-carboxymethyl-6,7-dihydro-1H, 5H-pyrido[1,2,3-de] quinoxaline-2,3-dione (2.80 g, 9.5 mmol), triethylamine (2.43 g, 24 mmol), and Bop-Cl (2.42 g, 9.5 mmol) in dichloromethane (40 mL) was stirred for 2 h at room temperature and diluted with ethyl acetate (800 mL). The mixture was washed with 5% potassium hydrogen sulfate, water, 1/15 phosphate buffer (pH 7.5), water, and brine, successively, dried over magnesium sulfate, and concentrated. The residue was recrystallized from acetone-ethyl acetate to give 3.22 g of the title compound. The mother liquid was concentrated and the residue was purified by silica gel column chromatography with ethyl acetate to 1% AcOH/ethyl acetate to give additionally 0.8 g of the title compound (72%).

¹H NMR (DMSO-d6) δ12.08 (bs, 1H), 9.45 (bs, 1H), 7.35 (bt, 1H, J=6.3 Hz), 7.24 (d, 1H, J=7.9 Hz), 7.00~7.18 (m, 4H), 5.18~5.30 (m, 1H), 4.07 (d, 2H, J=6.3 Hz), 3.61 (s, 3H), 3.03~3.20 (m, 1H), 2.74~2.90 (m, 3H), 2.63 (d, 2H, J=7.3 Hz), 2.55 (d, 2H, J=7.3 Hz), 2.05~2.20 (dm, 1H, J=14.0 Hz), 1.80~2.00 (m, 1H), 1.40 (s, 9H).

EXAMPLE 19

(S)-9-Chloro-5-[p-tert-butoxycarbonylaminomethyl-o-(2-carboxyethyl)phenylcarbamoylmethyl]-6,7-dihydro-1H, 5H-pyrido[1,2,3-de]quinoxaline-2,3-dione A procedure similar to that described in Example 2 was performed with (S)-9-chloro-5-[p-tert-butoxycarbonylaminomethyl-o-(2-methoxycarbonylethyl) phenylcarbamoylmethyl]-6,7-dihydro-1H, 5H-pyrido[1,2,3-de]quinoxaline-2,3-dione (3.05 g) to give 2.86 g of the title compound (96%).

¹H NMR (DMSO-d6) δ11.50~12.50 (br, 2H), 9.52 (bs, 1H), 7.34 (bt, 1H, J=5.9 Hz), 7.26 (d, 1H, J=8.3 Hz), 7.03~7.09 (m, 4H), 5.19~5.29 (m, 1H), 4.07 (d, 2H, J=6.3 Hz), 3.03~3.20 (m, 1H), 2.74~2.89 (m, 3H), 2.63 (d, 2H, J=7.3 Hz), 2.42 (d, 2H, J=7.3 Hz), 2.07~2.20 (dm, 1H, J=14.0 Hz), 1.80~1.98 (m, 1H), 1.40 (s, 9H).

EXAMPLE 20

(S)-9-Chloro-5-[p-aminomethyl-o-(2-carboxyethyl) phenylcarbamoylmethyl]-6,7-dihydro-1H, 5H-pyrido[1,2,3-de]quinoxaline-2,3-dione hydrochloride A procedure similar to that described in Example 11 was performed with (S)-9-chloro-5-[p-tertbutoxycarbonylaminomethyl-o-(2-carboxyethyl) phenylcarbamoylmethyl]-6,7-dihydro-1H, 5H-pyrido[1,2,3-de]quinoxaline-2,3-dione (2.86 g) to give 2.50 g of the title compound (98%).

$^1$H NMR (DMSO-d6) δ11.60~12.50 (br, 1H), 12.13 (bs, 1H), 9.61 (bs, 1H), 8.10~8.45 (br, 3H), 7.41 (d, 1H, J=7.9 Hz), 7.37 (d, 1H, J=2.0 Hz), 7.30 (dd, 1H, J=7.9, 2.0 Hz), 7.10 (d, 1H, J=2.0 Hz), 7.10 (d, 1H, J=2.0 Hz), 5.20~5.30 (m, 1H), 3.97 (d, 2H, J=5.6 Hz), 3.05~3.20 (m, 1H), 2.74~2.91 (m, 3H), 2.61~2.73 (m, 2H), 2.10~2.20 (dm, 1H, J=14.0 Hz), 1.82~1.98 (m, 1H).

EXAMPLE 21

(S)-9-Bromo-5-[p-tert-butoxycarbonylaminomethyl-o-(3-methoxycarbonylpropyl) phenylcarbamoylmethyl]-6,7-dihydro-1H, 5H-pyrido[1,2,3-de]quinoxaline-2,3-dione 1) 3-Methyl-6-nitrobenzaldehyde A mixture of 3-methyl-6-nitrobenzylalcohol (10 g, 59.8 mmol) and manganese dioxide (80 g) in dichloromethane (100 mL) was stirred for 9 h and passed through a celite short column. The eluent was concentrated and the residue was purified by silica gel column chromatography with 8:1 hexane/ethyl acetate to give 8.25 g of the title compound (84%).

$^1$H NMR (CDCl$_3$), δ10.44 (s, 1H), 8.05 (d, 1H, J=8.3 Hz), 7.72 (d, 1H, J=1.7 Hz), 7.53 (dd, 1H, J=8.3, 1.7 Hz), 2.53 (s, 3H).

2) 3-Methyl-6-nitrostyrene

To a suspension of methyltriphenylphosphnium bromide (18.86 g, 52.8 mmol) in THF (120 mL) was added 0.5M potassium hexamethyldisilazide in toluene (106 mL, 53.0 mmol) at −10° C. The mixture was stirred for 40 min at the same temperature and 3-methyl-6-nitrobenzaldehyde (8.0 g, 48 mmol) in THF (60 mL) was added. The mixture was stirred for 1 h at −10° C. and 0.2N hydrochloric acid (400 mL) was added. The mixture was extracted with ethyl acetate, washed with brine, dried over magnesium sulfate, and concentrated. The residue was purified by silica gel column chromatography with 15:1 hexane/ethyl acetate to give 5.10 g of the title compound (65%).

$^1$H NMR (CDCl$_3$), δ7.88 (d, 1H, J=8.3 Hz), 7.39 (d, 1H, J=1.7 Hz), 7.21 (dd, 1H, J=17.2, 11.2 Hz), 7.19 (dd, 1H, J=8.3, 1.7 Hz), 5.71 (dd, 1H, J=17.2, 1.0 Hz), 5.46 (dd, 1H, J=11.2 Hz), 2.46 (s, 3H).

3) Diethyl 2-(3-methyl-6-nitrophenyl)ethylmalonate

To a suspension of 60% sodium hydride (1.36 g, 34 mmol) in DMF (35 mL) was added diethyl malonate (7.00 g, 43.7 mmol). The mixture was heated at 60° C. for 1.5 h, allowed to cool at room temperature and 3-methyl-6-nitrostyrene (4.80 g, 29.4 mmol) in DMF (10 mL) was added dropwise. The mixture was again heated at 4°~50° C. for 4 h, poured into 0.1N hydrochloric acid, and extracted with a 1:1 toluene/ethyl acetate. The extract was washed with brine, dried over magnesium sulfate, and concentrated. The residue was purified by silica gel column chromatography with 10:1 hexane/ethyl acetate to give 2.70 g of the title compound (28%).

$^1$H NMR (CDCl$_3$) δ7.89 (d, 1H, J=8.9 Hz), 7.16 (s, 1H), 7.15 (d, 1H, J=8.9 Hz), 4.22 (q, 4H, J=7.3 Hz), 3.42 (t, 1H, J=7.3 Hz), 2.94 (t, 2H, J=7.9 Hz), 2.41 (s, 3H), 2.25 (q, 2H, J=7.9 Hz), 1.29 (t, 6H, J=7.3 Hz).

4) Diethyl 2-(3-phthalimidomethyl-6-nitrophenyl)ethylmalonate

A mixture of diethyl 2-(3-methyl-6-nitrophenyl)ethylmalonate (2.7 g, 8.35 mmol), N-bromosuccinimide (1.63 g, 9.19 mmol), and azobisisobutyronitrile (100 mg) in carbon tetrachloride (35 mL) was refluxed for 14 h, while 3×50 mg of AIBN were added every 3 h during the reaction. The insoluble material formed was removed by filtration and the filtrate was concentrated. The residue was dissolved in DMF (100 mL) and potassium phthalimide (1.3 g, 7.02 mmol) was added. The mixture was stirred for 5 h at 4°~50° C., poured into saturated sodium bicarbonate, and extracted with a 1:1 mixture of toluene and ethyl acetate. The organic layers were washed with brine, dried over magnesium sulfate, and concentrated. The residue was purified by silica gel column chromatography with 4:1 hexane/ethyl acetate to give 580 mg of the title compound (15%).

5) Methyl 4-(3-tert-butoxycarbonylaminomethyl-6-nitrophenyl)butanoate

A solution of diethyl 2-(3-phthalimidomethyl-6-nitrophenyl)ethylmalonate (580 mg, 1.24 mmol) in a mixture of dioxane (10 mL) and concentrated hydrochloric acid (10 mL) was refluxed for 30 h and concentrated. The residual water and hydrochloric acid were azeotropically distilled out with toluene. The residue was dissolved in methanol (10 mL) and thionyl chloride (2 mL) was added dropwise. The mixture was refluxed for 2 h and concentrated. The residual reagent and hydrogen chloride were azeotropically distilled out with toluene. The residue was dissolved in dichloromethane (150 mL) and di-tert-butyl dicarbonate (11 mL, 48 mmol) and triethylamine (15 mL) were added. The mixture was stirred for 5 h at room temperature, diluted with ethyl acetate, and washed with 5% potassium hydrogen sulfate, water, saturated sodium bicarbonate, water, and brine, successively. The organic layer was dried over magnesium sulfate and concentrated. The residue was purified by silica gel column chromatography with 7:1 to 5:1 hexane/ethyl acetate to give 8.03 g of the title compound (60%).

$^1$H NMR (CDCl$_3$) δ7.90 (d, 1H, J=8.9 Hz), 7.26 (dd, 1H, J=8.9, 1.7 Hz), 7.25 (d, 1H, J=1.7 Hz), 4.92~5.13 (br, 1H), 4.36 (bd, 2H, J=6.3 Hz), 3.68 (s, 3H), 2.92 (t, 2H, J=7.3 Hz), 2.41 (t, 2H, J=7.3 Hz), 1.99 (5et, 2H, J=7.3 Hz), 1.47 (s, 9H).

6) 4-tert-Butoxycarbonylaminomethyl-2-(3-methoxycarbonylpropyl)aniline

A procedure similar to that described in Example 9-6) was performed with methyl 4-(3-tert-butoxycarbonylaminomethyl-6-nitrophenyl)butanoate (140 mg, 0.4 mmol) to give the title compound.

$^1$H NMR (CDCl$_3$) δ6.94 (dd, 1H, J=8.3, 2.0 Hz), 6.92 (d, 1H, J=2.0 Hz), 6.61 (d, 1H, J=8.3 Hz), 4.65~4.77 (br, 1H), 4.15 (bd, 2H, J=5.3 Hz), 3.77 (s, 3H), 2.50 (t, 2H, J=7.3 Hz), 2.40 (t, 2H, J=7.3 Hz), 1.90 (5et, 2H, J=7.3 Hz), 1.45 (s, 9H).

7) (S)-9-Bromo-5-[p-tert-butoxycarbonylaminomethyl-o-(3-methoxycarbonylpropyl) phenylcarbamoylmethyl]-6,7-dihydro-1H, 5H-pyrido[1,2,3-de]quinoxaline-2,3-dione A procedure similar to that described in Example 9-7) was performed with 4-tert-butoxycarbonylaminomethyl-2-(3-methoxycarbonylpropyl)aniline (130 mg, 0.4 mmol) and (S)-9-bromo-5-carboxymethyl-6,7-dihydro-1H, 5H-pyrido[1,2,3-de]quinoxaline-2,3-dione (136 mg, 0.4 mmol) to give 118 mg of the title compound (62%).

$^1$H NMR (DMSO-d6) δ12.07 (bs, 1H), 9.37 (bs, 1H), 7.36 (bt, 1H, J=1.7 Hz), 7.24~7.31 (m, 2H), 7.17 (d, 1H, J=2.0 Hz), 7.07 (d, 1H, J=2.0 Hz), 7.02~7.10 (m, 1H), 5.19~5.30 (m, 1H), 4.07 (d, 2H, J=2.0 Hz), 3.58 (s, 3H), 3.00~3.20 (m, 1H), 2.89~2.91 (dm, 1H, J=14.0 Hz), 2.65~2.70 (m, 2H), 2.32 (t, 2H, J=7.3 Hz), 2.08~2.19 (dm, 1H, J=14.0 Hz), 1.80~1.98 (m, 1H), 1.73 (5et, 2H, J=7.3 Hz), 1.40 (s, 9H).

EXAMPLE 22

(S)-9-Bromo-5-[p-tert-butoxycarbonylaminomethyl-o-(3-carboxypropyl)phenylcarbamoylmethyl-6,7-dihydro-1H, 5H-pyrido[1,2,3-de]quinoxaline-2,3-dione A solution of (S)-9-bromo-5-[p-tert-butoxycarbonylaminomethyl-o-(3-methoxycarbonylpropyl)

phenylcarbamoylmethyl]-6,7-dihydro-1H, 5H-pyrido[1,2,3-de]quinoxaline-2,3-dione (110 mg, 0.17 mmol) in a mixture of 1N aqueous sodium hydroxide (1.5 mL), THF (1.5 mL), and methanol (1.5 mL) was stirred for 3 h at room temperature. The mixture was concentrated to ca. 2 mL and acidified with 5% aqueous potassium hydrogen sulfate. The precipitates formed were collected and dried in vacuo to give 103 mg of the title compound (96%).

EXAMPLE 23

(S)-9-Bromo-5-[p-aminomethyl-o-(3-carboxypropyl)phenylcarbamoylmethyl]-6,7-dihydro-1H, 5H-pyrido[1,2,3-de]quinoxaline-2,3-dione hydrochloride To a solution of (S)-9-Bromo-5-[p-tert-butoxycarbonylaminomethyl-o-(3-carboxypropyl)phenylcarbamoylmethyl]-6,7-dihydro-1H, 5H-pyrido[1,2,3-de]quinoxaline-2,3-dione (103 mg, 0.164 mmol)in 1,4-dioxane (5 mL) was added 4N hydrogen chloride in 1,4-dioxane (5 mL) at room temperature. The mixture was stirred for 20 h at room temperature and concentrated. The residual solid was dried in vacuo to give 90 mg of the title compound (97%).

$^1$H NMR (DMSO-d6), δ12.12 (br, 1H), 11.40~11.90 (br, 1H), 9.51 (br, 1H), 8.05~8.50 (br, 3H), 7.43 (d, 1H, J=7.6 Hz), 7.33 (d, 1H, J=2.0 Hz), 5.18~5.30 (m, 1H), 3.98 (bs, 2H), 3.03~3.21 (m, 1H), 2.81~2.90 (dm, 1H, J=14.0 Hz), 2.50~2.75 (m, 4H), 2.27 (t, 2H, J=7.3 Hz), 2.06~2.18 (dm, 1H, J=14.0 Hz), 1.80~1.95 (m, 1H), 1.73 (5et, 2H, J=7.3 Hz).

EXAMPLE 24

(5S)-9-Bromo-5-[p-tert-butoxycarbonylaminomethyl-o-(1-methoxycarbonyl-1-acetoxymethyl) phenylcarbamoylmethyl]-6,7-dihydro-1H, 5H-pyrido[1,2,3-de]quinoxaline-2,3-dione

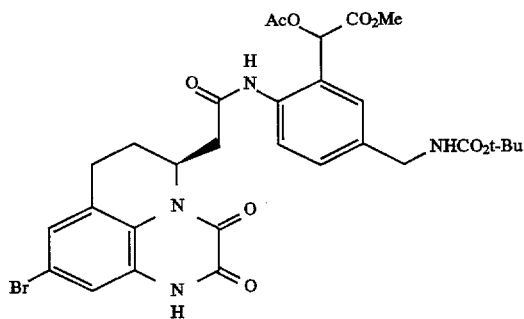

1) 1-(3-Methyl-6-nitrophenyl)-1-trimethylsiloxyacetonitrile

To a solution of 3-methyl-6-nitrobenzaldehyde (4.3 g, 26.0 mmol) in dichloromethane (40 mL) in the presence of zinc iodide (200 mg) was added trimethylsilyl cyanide (5.2 g, 52.0 mmol) at room temperature. The mixture was stirred for 2 h at room temperature, diluted with ethyl acetate, washed with brine, dried over magnesium sulfate, and concentrated to give 7.38 g of the title compound.

2) Methyl 1-(3-methyl-6-nitrophenyl)-1-hydroxyacetate

A solution of 1-(3-methyl-6-nitrophenyl)-1-trimethylsiloxyacetnitrile (7.3 g) in concentrated hydrochloric acid (60 mL) was heated at 80° C. for 2.5 h and a mixed solution of methanol and toluene was added. The solvents and hydrogen chloride were removed azeotropically by evaporation. The residue was dissolved in ethyl acetate, washed with brine, dried over magnesium sulfate, and concentrated to give 5.80 g of the title compound (99%).

$^1$H NMR (CDCl$_3$) δ7.95 (d, 1H, J=8.3 Hz), 7.46 (d, 1H, J=1.7 Hz), 7.29 (dd, 1H, J=8.3, 1.7 Hz), 5.81 (s, 1H), 3.76 (s, 3H), 2.46 (s, 3H).

3) Methyl 1-(3-methyl-6-nitrophenyl)-1-acetoxyacetate

A mixture of methyl 1-(3-methyl-6-nitrophenyl)-1-hydroxyacetate (5.70 g, 25.3 mmol), acetic anhydride (3.62 g, 35.5 mmol), triethylamine (3.60 g, 35.5 mmol), and 4-dimethylaminopyridine (500 mg) in dichloromethane (50 mL) was stirred for 1 h at room temperature and concentrated. The residue was dissolved in a mixture of ethyl acetate and 0.5N hydrochloric acid. The organic layer was separated, washed with brine, dried over magnesium sulfate, and concentrated. The residue was purified by column chromatography with 4:1 to 3:1 hexane/ethyl acetate to give 5.7 g of the title compound (84%).

$^1$H NMR (CDCl$_3$) δ7.99 (d, 1H, J=8.6 Hz), 7.40 (d, 1H, J=1.3 Hz), 7.33 (dd, 1H, J=8.6, 1.3 Hz), 6.86 (s, 1H), 3.76 (s, 3H), 2.47 (s, 3H), 2.21 (s, 3H).

4) Methyl 1-(3-azidomethyl-6-nitrophenyl)-1-acetoxyacetate

A mixture of methyl 1-(3-methyl-6-nitrophenyl)-1-acetoxyacetate (3.5 g, 13.8 mmol), N-bromosuccinimide (NBS, 2.70 g, 15.2 mmol), and azobisisobutyronitrile (AIBN, 100 mg) in carbon tetrachloride (65 mL) was refluxed for 13 h, while 3×50 mg of AIBN were added every 3 h during the reaction. NBS (1.35 g, 7.6 mmol) and AIBN (100 mg) were added further and the mixture was refluxed additionally for 7 h. The insoluble material formed was removed by filtration and the filtrate was concentrated. The residue was dissolved in DMF (50 mL) and sodium azide (1.0 g, 15.4 mmol) was added. The mixture was stirred for 1 h at room temperature, poured into a mixture of toluene, ethyl acetate, and 5% aqueous potassium hydrogen sulfate. The organic layer was separated, washed with brine, dried over magnesium sulfate, and concentrated. The residue was purified by silica gel column chromatography with 5:1 to 4:1 hexane/ethyl acetate to give 1.97 g of the title compound (46%).

$^1$H NMR (CDCl$_3$) δ8.09 (d, 1H, J=8.3 Hz), 7.57 (d, 1H, J=2.0 Hz), 7.51 (dd, 1H, J=8.3, 2.0 Hz), 6.88 (s, 1H), 4.52 (s, 2H), 3.77 (s, 3H), 2.23 (s, 3H).

5) 4-tert-Butoxycarbonylaminomethyl-2-(1-methoxycarbonyl-1-acetoxymethyl)aniline A solution of methyl 1-(3-azidomethyl-6-nitrophenyl)-1-acetoxyacetate (1.9 g, 6.16 mmol) in ethyl acetate (35 mL) in the presence of di-tert-butyl dicarbonate (1.48 g, 6.78 mmol) and 10% Pd/C was hydrogenated for 4 h under atmospheric pressure of hydrogen at room temperature. The catalyst was removed by filtration by using celite and the filtrate was concentrated to give 1.1 g of the crude title compound. The product was used for the next step without further purification.

$^1$H NMR (CDCl$_3$) δ7.15 (d, 1H, J=2.0 Hz), 7.11 (dd, 1H, J=8.3, 2.0 Hz), 6.67 (d, 1H, J=8.3 Hz), 6.02 (s, 1H), 4.68~4.82 (br, 1H), 4.20 (bd, 2H, J=5.6 Hz), 4.10~4.20 (br, 2H), 3.74 (s, 3H), 2.20 (s, 3H), 1.46 (s, 9H).

6) (5S)-9-Bromo-5-[p-tert-butoxycarbonylaminomethyl-o-(1-methoxycarbonyl-1acetoxymethyl)phenylcarbamoylmethyl]-6,7-dihydro-1H, 5H-pyrido[1,2,3-de]quinoxaline-2,3-dione A mixture of 4-tert-butoxycarbonylaminomethyl-2-(1-methoxycarbonyl-1-acetoxymethyl)aniline (500 mg, 1 mmol), (S)-9-bromo-5-carboxymethyl-6,7-dihydro-1H, 5H-pyrido[1,2,3-de]quinoxaline-2,3-dione (475 mg, 1.4 mmol), triethylamine (0.55 mL), and Bop-Cl (360 mg, 1.4 mmol) in dichloromethane (15 mL) was stirred for 48 h at room temperature and diluted with ethyl acetate (200 mL). The mixture was washed with 5% potassium hydrogen sulfate, water, 1/15 phosphate buffer (pH 7.5), water, and brine, successively, dried over magnesium sulfate, and concentrated. The residue was purified by silica gel column chromatography with 0.3% acetic acid/ethyl acetate to give 340 mg of the title compound (50%).

$^1$H NMR (DMSO-d6) δ12.07 (bs, 1H), 9.67 (bs, 1H), 7.44 (bt, 1H, J=5.6 Hz), 7.36 (d, 1H, J=8.9 Hz), 7.27 (d, 1H, J=8.9 Hz), 7.26 (s, 1H), 7.25 (d, 1H, J=2.0 Hz), 7.18 (d, 1H, J=2.0 Hz), 6.20, 6.17 (s, 1H), 5.15~5.28 (m, 1H), 4.11 (bd, 2H, J=5.6 Hz), 3.65 (s, 3H), 2.99~3.17 (m, 1H), 2.76~2.90 (dm, 1H, J=14.0 Hz), 2.55~2.68 (m, 2H), 2.04~2.20 (m, 1H), 2.11, 2.12 (s, 3H), 1.80~1.99 (m, 1H), 1.40 (s, 9H).

EXAMPLE 25

(5S)-9-Bromo-5-[p-tert-butoxycarbonylaminomethyl-o-(1-carboxy-1-hydroxymethyl) phenylcarbamoylmethyl]-6,7-dihydro-1H, 5H-pyrido[1,2,3-de]quinoxaline-2,3-dione A solution of (5S)-9-bromo-5-[p-tert-butoxycarbonylaminomethyl-o-(1-methoxycarbonyl-1-acetoxymethyl)phenylcarbamoylmethyl]-6,7-dihydro-1H, 5H-pyrido[1,2,3-de]quinoxaline-2,3-dione (310 mg, 0.46 mmol) in a mixture of 1N aqueous sodium hydroxide (6 mL), THF (5 mL), and methanol (5 mL) was stirred for 6 h at room temperature. The mixture was concentrated to ca. 6 mL and acidified with 5% aqueous potassium hydrogen sulfate. The precipitates formed were collected and dried to give 276 mg of the title compound (97%).

EXAMPLE 26

(5S)-9-Bromo-5-[p-aminomethyl-o-(1-carboxy-1-hydroxymethyl)phenyl carbamoylmethyl]-6,7-dihydro-1H, 5H-pyrido[1,2,3-de]quinoxaline-2,3-dione hydrochloride To a solution of (5S)-9-bromo-5-[p-tert-butoxycarbonylaminomethyl-o-(1-carboxy-1-hydroxymethyl)phenylcarbamoylmethyl]-6,7-dihydro-1H, 5H-pyrido[1,2,3-de]quinoxaline-2,3-dione (260 mg, 0.42 mmol) in 1,4-dioxane (10 mL) was added 4N hydrogen chloride in 1,4-dioxane (10 mL) at room temperature. The mixture was stirred for 14 h at room temperature and concentrated. The residual solid was washed with diethyl ether and dried in vacuo to give 240 mg of the title compound (100%).

$^1$H NMR (DMSO-d6) δ12.13 (br, 1H), 9.55, 9.58 (bs, 1H), 8.25~8.45 (br, 3H), 7.66, 7.71 (d, 1H, J=8.3 Hz), 7.52 (d, 1H, J=1.7 Hz), 7.42 (dd, 1H, J=8.3, 1.7 Hz), 7.21 (bs, 2H), 5.28, 5.30 (s, 1H), 5.15~5.25 (m, 1H), 3.99 (bd, 2, H, J=5.6 Hz), 3.01~3.21 (m, 1H), 2.65~2.95 (m, 3H), 2.10~2.20 (dm, 1H, J=14.0 Hz), 1.80~1.95 (m, 1H).

EXAMPLE 27

(5S)-9-Chloro-5-[p-tert-butoxycarbonylaminomethyl-o-(1-methoxycarbonyl-1-acetoxymethyl) phenylcarbamoylmethyl]-6,7-dihydro-1H, 5H-pyrido[1,2,3-de]quinoxaline-2,3-dione A procedure similar to that described in Example 9-7) was performed with 4-tert-butoxycarbonylaminomethyl-2-(1-methoxycarbonyl-1-acetoxymethyl) aniline (500 mg, 1 mmol) and (S)-9-chloro-5-carboxymethyl-6,7-dihydro-1H, 5H-pyrido[1,2,3-de]quinoxaline-2,3-dione (413 mg, 1.4 mmol) to give 275 mg of the title compound (43.7%).

$^1$H NMR (DMSO-d6) δ12.08 (bs, 1H), 9.67 (bs, 1H), 7.44 (bt, 1H, J=5.9 Hz), 7.36 (d, 1H, J=8.3 Hz), 7.26 (d, 1H, J=8.3 Hz), 7.22 (s, 1H), 7.11 (d, 1H, J=2.0 Hz), 7.03 (d, 1H, J=2.0 Hz), 6.20, 6.17 (s, 1H), 5.15~5.28 (m, 1H), 4.10 (bd, 2H, J=5.9 Hz), 3.65 (s, 3H), 2.98~3.18 (m, 1H), 2.75~2.89 (dm, 1H, J=14.0 Hz),2.56~2.67 (m, 2H),2.05~2.21 (m, 1H), 2.11, 2.12 (s, 3H), 1.80~1.99 (m, 1H), 1.40 (s, 9H).

EXAMPLE 28

(5S)-9-Chloro-5-[p-tert-butoxycarbonylaminomethyl-o-(1-carboxy-1-hydroxymethyl) phenylcarbamoylmethyl]-6,7-dihydro-1H, 5H-pyrido[1,2,3-de]quinoxaline-2,3-dione A procedure similar to that described in Example 25 was performed with (5S)-9-chloro-5-[p-tert-butoxycarbonylaminomethyl-o-(1-methoxycarbonyl-1-acetoxymethyl) phenylcarbamoylmethyl]-6,7-dihydro-1H, 5H-pyrido[1,2,3-de]quinoxaline-2,3-dione (260 mg, 0.41 mmol) to give 210 mg of the title compound (89%).

EXAMPLE 29

(5S)-9-Chloro-5-[p-aminomethyl-o-(1-carboxy-1-hydroxymethyl)phenyl carbamoylmethyl]-6,7-dihydro-1H, 5H-pyrido[1,2,3-de]quinoxaline-2,3-dione hydrochloride A procedure similar to that described in Example 26 was performed with (5S)-9-Chloro-5-[p-tert-butoxycarbonylaminomethyl-o-(1-carboxy-1-hydroxymethyl) phenylcarbamoylmethyl]-6,7-dihydro-1H, 5H-pyrido[1,2,3-de]quinoxaline-2,3-dione (195 mg, 0.34 mmol) to give 180 mg of the title compound (100%).

$^1$H NMR (DMSO-d6) δ12.14 (br, 1H), 9.54, 9.57 (bs, 1H), 8.20~8.45 (br, 3H), 7.66, 7.71 (d, 1H, J=8.3 Hz), 7.52 (d, 1H, J=1.7 Hz), 7.41 (dd, 1H, J=8.3, 1.7 Hz), 7.11 (bs, 2H), 5.27, 5.30 (s, 1H), 5.15~5.30 (m, 1H), 3.99 (bd, 2H, J=5.6 Hz), 3.03~3.20 (m, 1H), 2.60~2.90 (m, 3H), 2.10~2.20 (dm, 1H, J=14.0 Hz), 1.80~1.95 (m, 1H).

EXAMPLE 30

(S)-9-Chloro-5-[p-tert-butoxycarbonylaminomethyl-o-(tert-butoxycarbonylmethoxy) phenylcarbamoylmethyl]-6,7-dihydro-1H, 5H-pyrido[1,2,3-de]quinoxaline-2,3-dione

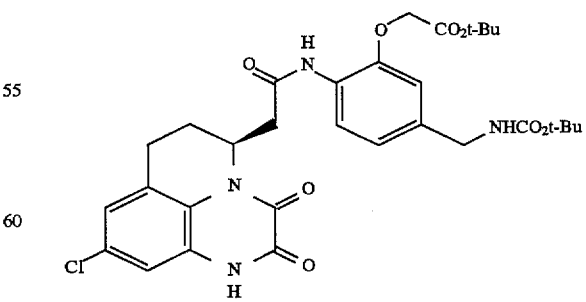

1) 3-tert-Butoxycarbonylmethoxy-4-nitrotoluene

A mixture of 3-methyl-6-nitrophenol (30.62 g, 200 mmol) and tert-butyl bromacetate (46.8 g, 240 mmol) in acetonitrile (700 mL)in the presence of potassium carbonate (69.1 g, 500 mmol) was refluxed for 2 h. Inorganic materials were removed by filtration and the filtrate was concentrated. The residue was diluted with ethyl acetate, washed with brine, dried over magnesium sulfate, and extensively concentrated in vacuo to give 54.2 g of the title compound (quant).

$^1$H NMR (CDCl$_3$) δ7.82 (d, 1H, J=8.3 Hz), 6.87 (d, 1H, J=8.3 Hz), 6.74 (s, 1H), 4.65 (s, 2H), 2.40 (s, 3H), 1.47 (s, 9H).

2) 4-Azidomethyl-2-tert-butoxycarbonylmethoxynitrobenzene

A mixture of 3-tert-butoxycarbonylmethoxy-4-nitrotoluene (36.1 g, 120 mmol), N-bromosuccinimide (21.3 g, 120 mmol), and benzoyl peroxide (4 g) in carbon tetrachloride (500 mL) was refluxed for 18 h. The insoluble material formed was removed by filtration and the filtrate was concentrated. The residue was dissolved in DMF (10 mL) and sodium azide (5.2 g, 80 mmol) was added. The mixture was stirred for 2 h at 50° C., poured into brine, and extracted with a 1:1 mixture of toluene and ethyl acetate. The organic layers were washed with brine, dried over magnesium sulfate, and concentrated. The residue was purified by silica gel column chromatography with 9:1 to 7:3 hexane/ethyl acetate to give 13.4 g of the title compound (36%).

$^1$H NMR (CDCl$_3$) δ7.89 (d, 1H, J=8.3 Hz), 7.01 (dd, 1H, J=8.3, 1.7 Hz), 6.93 (d, 1H, J=1.7 Hz), 4.70 (s, 2H), 4.43 (s, 2H), 1.48 (s, 9H).

3) 4-tert-Butoxycarbonylaminomethyl-2-tert-butoxycarbonylmethoxyaniline

A solution of 4-azidomethyl-2-tert-butoxycarbonylmethoxynitrobenzene (2.96 g, 10 mmol) in ethyl acetate (50 mL) in the presence of di-tert-butyl dicarbonate (2.40 g, 11 mmol) and 10% Pd/C (1 g) was hydrogenated for 12 h under atmospheric pressure of hydrogen at room temperature. The catalyst was removed by filtration through celite and the filtrate was concentrated. The residue was purified by silica gel column chromatography with 3:1 to 1:1 hexane/ethyl acetate to give 1.75 g of the title compound (50%).

$^1$H NMR (CDCl$_3$) δ6.73 (dd, 1H, J=8.3 Hz), 6.68 (d, 1H, J=8.3, 1.7 Hz), 6.66 (d, 1H, J=8.3 Hz), 4.65~4.75 (br, 1H), 4.52 (s, 2H), 4.16 (d, 2H, J=5.6 Hz), 3.90~4.00 (br, 2H), 1.49 (s, 9H), 1.46 (s, 9H).

4) (S)-9-Chloro-5-[p-tert-butoxycarbonylaminomethyl-o-(tert-butoxycarbonylmethoxy) phenylcarbamoylmethyl]-6,7-dihydro-1H, 5H-pyrido[1,2,3-de]quinoxaline-2,3-dione A mixture of 4-tert-butoxycarbonylaminomethyl-2-tert-butoxycarbonylmethoxyaniline (930 mg, 2.61 mmol), (S)-9-chloro-5-carboxymethyl-6,7-dihydro-1H, 5H-pyrido[1,2,3-de]quinoxaline-2,3-dione (807 mg, 2.74 mmol), Bop-Cl (770 mg, 2.99 mmol), and triethylamine (2 mL) in dichloromethane (20 mL) was stirred for 4 days at room temperature. The mixture was diluted with ethyl acetate (500 mL) and washed with 5% aqueous potassium hydrogen sulfate, water, phosphate buffer (pH 7.5), water, and brine, successively, dried over magnesium sulfate, and concentrated. The residual solid was recrystallized from acetone-ethyl acetate to give 1.04 g of the title compound. The mother liquid was concentrated and the residue was purified by silica gel column chromatography with 0.3% acetic acid/ethyl acetate to give additionally 360 mg of the title compound. A total amount of 1.40 g of the title compound was obtained (85%).

$^1$H NMR (DMSO-d6) δ12.08 (bs, 1H), 9.30 (bs, 1H), 7.79 (d, 1H, J=8.3 Hz), 7.32 (bt, 1H, J=5.9 Hz), 7.10 (d, 1H, J=2.0 Hz), 7.03 (d, 1H, J=8.3 Hz), 6.80 (dd, 1H, J=8.3, 1.7 Hz), 6.78 (d, 1H, J=1.7 Hz), 5.15~5.25 (m, 1H), 4.64 (s, 2H), 4.05 (bd, 2H, J=5.9 Hz), 3.05~3.20 (m, 1H), 2.70~2.88 (m, 2H), 2.55~2.70 (bd, 1H, J=14.0 Hz), 2.03~2.20 (dm, 1H, J=14.0 Hz), 1.80~1.95 (m, 1H), 1.43 (s, 9H), 1.39 (s, 9H).

EXAMPLE 31

(S)-9-Chloro-5-[p-aminomethyl-o-(carboxymethoxy) phenylcarbamoylmethyl]-6,7-dihydro-1H, 5H-pyrido[1,2,3-de]quinoxaline-2,3-dione hydrochloride A suspension of (S)-9-chloro-5-[p-tert-butoxycarbonylaminomethyl-o-(tert-butoxycarbonylmethoxy) phenylcarbamoylmethyl]-6,7-dihydro-1H, 5H pyrido[1,2,3-de]quinoxaline-2,3-dione (1.30 g) in 4N hydrogen chloride in 1,4-dioxane (50 mL) was stirred for 20 h at room temperature and 2N hydrochloric acid (35 mL) was added. The mixture was stirred further for 1 h and concentrated in vacuo. The residue was recrystallized from water to give 900 mg of the title compound.

$^1$H NMR (DMSO-d6) δ12.50~13.50 (br, 1H), 12.13 (bs, 1H), 9.44 (bs, 1H), 8.15~8.45 (br, 3H), 8.10 (d, 1H, J=8.3 Hz), 7.19 (d, 1H, J=1.7 Hz), 7.10 (d, 1H, J=1.7 Hz), 7.07 (d, 1H, J=1.7 Hz), 7.05 (dd, 1H, J=8.3, 1.7 Hz), 5.15~5.30 (m, 1H), 4.73 (s, 2H), 3.95 (bd, 1H, J=5.3 Hz), 3.05~3.20 (m, 1H), 2.75~2.88 (m, 2H), 2.63 (dd, 1H, J=5.3, 14 Hz), 2.09~2.20 (dm, 1H, J=14 Hz), 1.80~1.95 (m, 1H).

EXAMPLE 32

(S)-9-Chloro-5-[p-tert-butoxycarbonylaminomethyl-o-(ethoxycarbonylmethoxy) phenylcarbamoylmethyl]-6,7-dihydro-1H, 5H-pyrido[1,2,3-de]quinoxaline-2,3-dione A mixture of (S)-9-chloro-5-[p-aminomethyl-o-(carboxymethoxy)phenylcarbamoylmethyl]-6,7-dihydro-1H, 5H-pyrido[1,2,3-de]quinoxaline-2,3-dione hydrochloride (1.50 g, 2.86 mmol), triethylamine (2 mL), and di-tert-butyl dicarbonate (750 mg, 3.44 mmol) in dichloromethane was stirred for 6 h at room temperature and concentrated. To the residue was added 2% aqueous potassium hydrogen sulfate (200 mL) and the precipitates were collected by filtration. The precipitates were dried in vacuo and suspended in dichloromethane (20 mL). Bop-Cl (884 mg, 3.43 mmol), ethanol (264 mg, 5.72 mmol), and triethylamine (2.5 mL) were added and the mixture was stirred for 20 h at room temperature. The mixture was diluted with ethyl acetate, washed successively with 5% potassium hydrogen sulfate and brine, dried over magnesium sulfate, and concentrated. The residue was purified by silica gel column chromatography with 5:1 ethyl acetate/hexane to 5:1 0.3% acetic acid in ethyl acetate/hexane to give 310 mg of the title compound (18%).

$^1$H NMR (DMSO-d6), δ11.90~12.00 (br, 1H), 9.31 (bs, 1H), 7.78 (d, 1H, J=8.3 Hz), 7.33 (bt, 1H, J=5.9 Hz), 7.10 (d, 1H, J=2.0 Hz), 7.03 (d, 1H, J=8.3 Hz), 6.81 (dd, 1H, J=8.3, 1.7 Hz), 6.80 (d, 1H, J=1.7 Hz), 5.18~5.28 (m, 1H), 4.77 (bs, 2H), 4.17 (q, 2H, J=7.3 Hz), 4.05 (bd, 2H, J=6.3 Hz), 3.02~3.20 (m, 1H), 2.70~2.90 (m, 2H), 2.55~2.70 (dd, 1H, J=14.0, 4.0 Hz), 2.05~2.18 (dm, 1H, J=14.0 Hz), 1.78~1.95 (m, 1H), 1.39 (s, 9H), 1.22 (t, 3H, J=7.3 Hz).

EXAMPLE 33

(S)-9-Chloro-5-[p-aminomethyl-o-(ethoxycarbonylmethoxy)phenylcarbamoylmethyl]-6,7-dihydro-1H, 5H-pyrido[1,2,3-de]quinoxaline-2, 3-dione hydrochloride A suspension of (S)-9-chloro-5-[p-tert-butoxycarbonylaminomethyl-o-(ethoxycarbonylmethoxy)

phenylcarbamoylmethyl]-6,7-dihydro-1H, 5H-pyrido[1,2,3-de]quinoxaline-2,3-dione (150 mg) in ethyl acetate (4 mL) was added 4N hydrogen chloride in 1,4-dioxane (2 mL). The mixture was stirred for 3 h at room temperature, and concentrated in vacuo to give 135 mg of the title compound.

$^1$H NMR (DMSO-d6) δ12.13 (bs, 1H), 12.13 (bs, 1H), 9.42 (bs, 1H), 8.10~8.50 (br, 3H), 7.92 (d, 1H, J=7.92 Hz), 7.17 (d, 1H, J=2.0 Hz), 7.11 (d, 1H, J=2.0 Hz), 7.07 (d, 1H, J=2.0 Hz), 7.05 (dd, 1H, J=7.9, 2.0 Hz), 5.18~5.28 (m, 1H), 4.82 (bs, 2H), 4.18 (q, 2H, J=7.3 Hz), 3.95 (bd, 1H, J=5.0 Hz), 3.02~3.20 (m, 1H), 2.72~2.89 (m, 2H), 2.64 (dd, 1H, J=5.0, 14 Hz), 2.05~2.20 (dm, 1H, J=14 Hz), 1.80~1.98 (m, 1H), 1.22 (t, 3H, J=7.3 Hz).

EXAMPLE 34

(S)-9-Bromo-5-[p-tert-butoxycarbonylaminomethyl-o-(tert-butoxycarbonylmethoxy)phenylcarbamoylmethyl]-6,7-dihydro-1H, 5H-pyrido[1,2,3-de]quinoxaline-2,3-dione A procedure similar to that described in Example 18-6) was performed with 4-tert-butoxycarbonylaminomethyl-2-tert-butoxycarbonylmethoxyaniline (990 mg, 2.61 mmol) and (S)-9-bromo-5-carboxymethyl-6,7-dihydro-1H, 5H-pyrido[1,2,3-de]quinoxaline-2,3-dione (1.06 g, 3.12 mmol) to give a total amount of 1.42 g of the title compound (81%).

$^1$H NMR (DMSO-d6) δ12.04 (bs, 1H), 9.29 (bs, 1H), 7.79 (d, 1H, J=8.3 Hz), 7.31 (bt, 1H, J=5.9 Hz), 7.22 (d, 1H, J=1.7 Hz), 7.16 (d, 1H, J=1.7 Hz), 6.80 (dd, 1H, J=8.3, 1.7 Hz), 6.78 (d, 1H, J=8.3 Hz), 5.18~5.28 (m, 1H), 4.64 (s, 2H), 4.05 (bd, 2H, J=5.9 Hz), 3.05~3.20 (m, 1H), 2.70~2.95 (m, 2H), 2.58~2.68 (bd, 1H, J=14.0 Hz), 2.08~2.18 (dm, 1H, J=14.0 Hz), 1.75~1.90 (m, 1H), 1.43 (s, 9H), 1.39 (s, 9H).

EXAMPLE 35

(S)-9-Bromo-5-[p-aminomethyl-o-(carboxymethoxy)phenylcarbamoylmethyl]6,7-dihydro-1H, 5H-pyrido[1,2,3-de]quinoxaline-2,3-dione hydrochloride A procedure similar to that described in Example 31 was performed with (S)-9-bromo-5-[p-tert-butoxycarbonylaminomethyl-o-(tert-butoxycarbonylmethoxy) phenylcarbamoylmethyl]-6,7-dihydro-1H, 5H-pyrido[1,2,3-de]quinoxaline-2,3-dione (1.35 g, 2.0 mmol) to give 997 mg of the title compound.

$^1$H NMR (DMSO-d6) δ11.50~12.50 (br, 1H), 12.11 (bs, 1H), 9.43 (bs, 1H), 8.10~8.40 (br, 3H), 7.92 (d, 1H, J=8.3 Hz), 7.21 (d, 1H, J=1.7 Hz), 7.18 (bs, 1H), 7.16 (d, 1H, J=2.0 Hz), 7.04 (d, 1H, J=8.3 Hz), 5.20~5.30 (m, 1H), 4.73 (s, 2H), 3.96 (d, 1H, J=5.3 Hz), 3.05~3.20 (m, 1H), 2.73~2.88 (m, 2H), 2.60~2.69 (bd, 1H, J=14 Hz), 2.08~2.20 (dm, 1H, J=14 Hz), 1.82~1.98 (m, 1H).

EXAMPLE 36

(S)-9-Bromo-5-[p-tert-butoxycarbonylaminomethyl-o-(4-ethoxycarbonylbutyl)phenylcarbamoylmethyl]-6,7-dihydro-1H, 5H-pyrido[1,2,3-de]quinoxaline-2,3-dione dione 1) Methyl 5-phthalimidomethyl-2-nitrobenzoate A mixture of methyl 5-methyl-2-nitrobenzoate (35.0 g, 179 mmol), N-bromosuccinimide (33.5 g, 188 mmol), and azobisisobutyronitrile (500 mg) in carbon tetrachloride (450 mL) was refluxed for 14 h. The insoluble material formed was removed by filtration and the filtrate was concentrated. The residue was dissolved in DMF (300 mL) and potassium phthalimide (19.41 g, 45 mmol) was added. The mixture was stirred for 2 h at 50° C., poured into brine, and extracted with a 1:1 mixture of toluene and ethyl acetate. The organic layers were washed with brine, dried over magnesium sulfate, and concentrated. The residue was purified by silica gel column chromatography with 4:1 to 2:1 hexane/ethyl acetate to give 20.0 g of the title compound (33%).

$^1$H NMR (CDCl$_3$) δ7.85~7.92 (m, 3H), 7.73~7.80 (m, 3H), 7.68 (dd, 1H, J=8.2, 2.0 Hz), 4.92 (s, 2H), 3.91 (s, 3H).

2) Methyl 5-aminomethyl-2-nitrobenzoate hydrochloride

A solution of methyl 5-phthalimidomethyl-2-nitrobenzoate (10.0 g, 29.4 mmol) in a mixture of 1,4-dioxane (50 mL) and concentrated hydrochloric acid (50 mL) was refluxed for 25 h and concentrated in vacuo. The residue was washed with a mixture of toluene/ethyl acetate and dried in vacuo to give 8.16 g of a solid. The residual solid was dissolved in methanol (100 mL) and thionyl chloride (12 mL) was added slowly. The mixture was refluxed for 1 h and concentrated. The residual solid was dispersed in toluene, collected by filtration, and dried in vacuo to give 6.60 g of the title compound (91%).

$^1$H NMR (DMSO-d6) δ8.40~9.90 (br, 3H), 8.15 (d, 1H, J=8.3 Hz), 8.02 (d, 1H, J=2.0 Hz), 7.95 (dd, 1H, J=8.3, 2.0 Hz), 4.20 (bs, 2H), 3.87 (s, 3H).

3) Methyl 5-tert-butoxycarbonylaminomethyl-2-nitrobenzoate

A mixture of methyl 5-aminomethyl-2-nitrobenzoate hydrochloride (6.50 g, 26.4 mmol), di-tert-butyl dicarbonate (6.8 g, 31.1 mmol), and triethylamine (8 mL) in dichloromethane (150 mL) was stirred for 5 h at room temperature. After being concentrated, the residue was dispersed between ethyl acetate and 5% aqueous potassium hydrogen sulfate and the organic layer was washed successively with saturated aqueous sodium bicarbonate, water, and brine, dried over magnesium sulfate, and concentrated. The residue was purified by silica gel column chromatography with 6:1 to 3:1 hexane/ethyl acetate to give 7.6 g of the title compound (93%).

$^1$H NMR (CDCl$_3$) δ7.91 (d, 1H, J=8.6 Hz), 7.61 (d, 1H, J=2.0 Hz), 7.54 (dd,1H, J=8.6, 2.0 Hz), 4.90~5.12 (br, 1H), 4.41 (bd, 1H, J=5.9 Hz), 3.92 (s, 3H), 1.46 (s, 9H).

4) 5-tert-Butoxycarbonylaminomethyl-2-nitrobenzylalcohol

To a solution of methyl 5-tert-butoxycarbonylaminomethyl-2-nitrobenzoate (2.0 g, 6.45 mmol) and sodium borohydride (740 mg, 19.56 mmol) in THF (11 mL) was added dropwise methanol (1.5 mL) over 1.5 h under reflux. After the addition was completed, the excess reagent was decomposed with 5% aqueous potassium hydrogen sulfate. The mixture was extracted with ethyl acetate. The organic layer was washed with brine, dried over magnesium sulfate, and concentrated. The residue was purified by silica gel column chromatography with 3:1 to 1:1 hexane/ethyl acetate to give 1.16 g of the title compound (64%).

$^1$H NMR (CDCl$_3$) δ8.09 (d, 1H, J=8.3 Hz), 7.65 (d, 1H, J=2.0 Hz), 7.38 (dd, 1H, J=8.3, 2.0 Hz), 4.95~5.15 (br, 1H), 4.98 (d, 2H, J=6.3 Hz), 4.41 (d, 2H, J=5.9 Hz), 2.65 (t, 1H, J=6.3 Hz), 1.47 (s, 9H).

5) 5-tert-Butoxycarbonylaminomethyl-2-nitrobenzylaldehyde

A mixture of 2-nitro-5-tert-butoxycarbonylaminomethylbenzylalcohol (700 mg, 2.48 mmol) and manganese oxide (7.0 g) in dichloromethane (20 mL) was stirred at room temperature for 5 h. The reagent was removed by filtration through celite and the filtrate was concentrated to give 580 mg of the title compound (84%).

¹H NMR (CDCl₃) δ10.43(s, 1H), 8.11 (d, 1H, J=8.6 Hz), 7.83 (d, 1H, J=2.0 Hz), 7.68 (dd, 1H, J=8.6, 2.0 Hz), 5.05~5.25 (br, 1H), 4.45 (bd, 2H, J=5.9 Hz), 1.47 (s, 9H).

6) Ethyl 5-(5-tert-butoxycarbonylaminomethyl-2-nitrophenyl)pent-4-enoate

To a suspension of 3-ethoxycarbonylpropyltriphenylphosphonium bromide (940 mg, 2.05 mmol) in THF (7 mL) at −78° C. was added a 0.5N solution of potassium hexamethyldisilazide (4 mL, 2.0 mmol). The mixture was stirred for 1 h at −78° C. and a solution of 5-tert-butoxycarbonylaminomethyl-2-nitrobenzylaldehyde (580 mg, 2.07 mmol) in THF (10 mL) was added slowly. The mixture was allowed to warm to room temperature, poured into 1% aqueous potassium hydrogen sulfate (100 mL), and extracted with ethyl acetate. The organic layers were washed with brine, dried over magnesium sulfate, and concentrated. The residue was purified by silica gel column chromatography with 3:1 hexane/ethyl acetate to give 590 mg of the title compound (78%) as a 3:1 mixture of cis and trans isomers.

Cis isomer: ¹H NMR (CDCl₃) δ8.02 (d, 1H, J=8.3 Hz), 7.33 (dd, 1H, J=8.3, 2.0 Hz), 7.29 (d, 1H, J=2.0 Hz), 6.76 (d, 1H, J=11.5 Hz), 5.80 (dt, 1H, J=11.5, 7.0 Hz), 5.08~5.22 (br, 1H), 4.39 (bd, 2H, J=6.6 Hz), 4.11 (q, 2H, J=7.3 Hz), 2.30~2.65 (m, 4H), 1.46 (s, 9H), 1.24 (t, 3H, J=7.3 Hz).

Trans isomer: ¹H NMR (CDCl₃) δ7.89 (d, 1H, J=8.6 Hz), 7.44 (d, 1H, J=2.0 Hz), 7.27 (dd, 1H, J=8.6, 2.0 Hz), 6.92 (d, 1H, J=17.2 Hz), 6.23 (dt, 1H, J=17.2, 7.0 Hz), 4.90~5.10 (br, 1H), 4.37 (bd, 2H, J=6.6 Hz), 4.17 (q, 2H, J=7.3 Hz), 2.30~2.65 (m, 4H), 1.46 (s, 9H), 1.27 (t, 3H, J=7.3 Hz).

7) 2-(4-Ethoxycarbonylbutyl)-4-tert-butoxycarbonylaminomethylaniline

A solution of ethyl 5-(5-tert-butoxycarbonylaminomethyl-2-nitrophenyl)pent-4-enoate (560 mg, 1.48 mmol) in ethyl acetate (20 mL) was hydrogenated over platinum oxide (100 mg) under atmospheric pressure of hydrogen at room temperature for 2.5 h. The mixture was passed through celite and the filtrate was concentrated to give 560 mg of the title compound (100%).

¹H NMR (CDCl₃), δ6.90~7.00 (m, 2H), 6.62 (d, 1H, J=8.6 Hz), 4.60~4.80 (br, 1H), 4.17 (bd, 2H, J=8.6 Hz), 4.13 (q, 2H, J=7.3 Hz), 3.30~3.88 (br, 2H), 2.49 (t, 2H, J=7.3 Hz), 2.35 (t, 2H, J=7.3 Hz), 1.58~1.80 (m, 4H) 1.49 (s, 9H), 1.26 (t, 3H, J=7.3 Hz).

8) (S)-9-Bromo-5-[p-tert-butoxycarbonylaminomethyl-o-(4-ethoxycarbonylbutyl)phenylcarbamoylmethyl]-6,7-dihydro-1H, 5H-pyrido[1,2,3-de]quinoxaline-2,3-dione A procedure similar to that described in Example 18-6) was performed with 2-(4-ethoxycarbonylbutyl)-4-tert-butoxycarbonylaminomethylaniline (256 mg, 0.73 mmol) and (S)-9-bromo-5-carboxymethyl-6,7-dihydro-1H, 5H-pyrido[1,2,3-de]quinoxaline-2,3-dione (297 mg, 0.88 mmol) to give 365 mg of the title compound after silica gel column chromatography with 0.3% acetic acid/ethyl acetate (74%).

¹H NMR (DMSO-d6) δ12.08 (bs, 1H), 9.37 (bs, 1H), 7.37 (bt, 1H, J=5.3 Hz), 7.25 (dd, 1H, J=8.3, 2.0 Hz), 7.24 (d, 1H, J=2.0 Hz), 7.17 (d, 1H, J=2.0 Hz), 7.03 (d, 1H, J=8.3 Hz), 5.18~5.30 (m, 1H), 4.05 (bd, 2H, J=5.3 Hz), 4.03 (q, 2H, J=7.3 Hz), 3.05~3.21 (m, 1H), 2.80~2.90 (dm, 1H, J=14 Hz), 2.51~2.69 (m, 4H), 2.30 (t, 2H, J=7.3 Hz), 2.05~2.18 (dm, 1H, J=14.0 Hz), 1.80~1.98 (m, 1H), 1.40~1.65 (m, 4H), 1.39 (s, 9H), 1.16 (t, 3H, J=7.3 Hz).

EXAMPLE 37

(S)-9-Bromo-5-[p-tert-butoxycarbonylaminomethyl-o-(4-carboxybutyl)phenylcarbamoylmethyl]-6,7-dihydro-1H, 5H-pyrido[1,2,3-de]quinoxaline-2,3-dione A procedure similar to that described in Example 10 was performed with (S)-9-bromo-5-[p-tert-butoxycarbonylaminomethyl-o-(4-ethoxycarbonylbutyl)phenylcarbamoylmethyl]-6,7-dihydro-1H, 5H-pyrido[1,2,3-de]quinoxaline-2,3-dione (300 mg, 0.446 mmol) to give the title compound (quant).

EXAMPLE 38

(S)-9-Bromo-5-[p-aminomethyl-o-(4-carboxybutyl)phenylcarbamoylmethyl]-6,7-dihydro-1H, 5H-pyrido[1,2,3-de]quinoxaline-2,3-dione hydrochloride A procedure similar to that described in Example 11 was performed with (S)-9-bromo-5-[p-tert-butoxycarbonylaminomethyl-o-(4-carboxybutyl)phenylcarbamoylmethyl]-6,7-dihydro-1H, 5H-pyrido[1,2,3-de]quinoxaline-2,3-dione (0.446 mmol) to give 250 mg of the title compound (97%).

¹H NMR (DMSO-d6) δ11.0~13.0 (br, 2H), 9.53 (bs, 1H), 7.80~8.80 (br, 3H 7.40 (d, 1H, J=8.3 Hz), 7.32 (d, 1H, J=2.0 Hz), 7.27 (dd, 1H, J=8.3, 2.0 Hz), 7.25 (d, 1H, J=2.0 Hz), 7.19 (d, 1H, J=2.0 Hz), 5.20~5.30 (m, 1H), 3.98 (bs, 2H), 3.05~3.22 (m, 1H), 2.80~2.91 (dm, 1H, J=14.0 Hz), 2.52~2.80 (m, 4H), 2.24 (t, 2H, J=7.3 Hz), 2.06~2.16 (dm, 1H, J=14.0 Hz), 1.80~1.98 (m, 1H), 1.42~1.62 (m, 4H).

EXAMPLE 39

(S)-9-Chloro-5-[p-tert-butoxycarbonylaminomethyl-o-(3,3-diethoxycarbonylpropyl)phenylcarbamoylmethyl]-6,7-dihydro-1H, 5H-pyrido[1,2,3-de]quinoxaline-2,3-dione

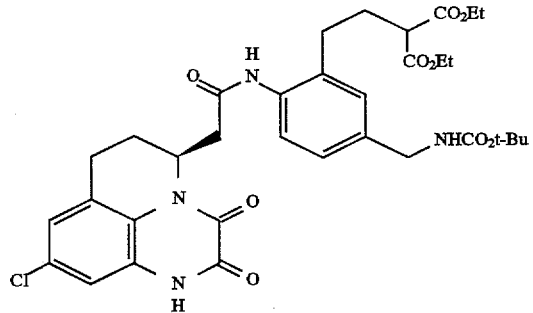

1) 3-tert-Butoxycarbonylaminomethyl-5-nitrostyrene

To a suspension of methyltriphenylphosphonium bromide (4.1 g, 11.5 mmol) in THF (40 mL) at −78° C. was added 0.5N potassium hexamethyldisilazide (24 mL, 12 mmol) in toluene. The mixture was stirred for 3 h at −78° C. and a solution of 5-tert-butoxycarbonylaminomethyl-2-nitrobenzaldehyde (3.2 g, 11.4 mmol) in THF (40 mL) was added slowly. The mixture was allowed to warm to room temperature, poured into 2% aqueous potassium hydrogen sulfate (250 mL), and extracted with ethyl acetate. The organic layers were washed with brine, dried over magnesium sulfate, and concentrated. The residue was purified by silica gel column chromatography with 7:1 to 5:1 hexane/ethyl acetate to give 2.4 g of the title compound (76%).

¹H NMR (CDCl₃) δ7.93 (d, 1H, J=8.3 Hz), 7.50 (d, 1H, J=2.0 Hz), 7.32 (dd, 1H, J=8.3, 2.0 Hz), 7.19 (dd, 1H, J=17.2, 11.2 Hz), 5.73 (dd, 1H, J=17.2, 1.0 Hz), 5.49 (dd, 1H, J=11.2, 1.0 Hz), 4.90~5.11 (br, 1H), 4.39 (bd, 2H, J=5.9 Hz), 1.47 (s, 9H).

2) Ethyl 4-(5-tert-butoxycarbonylaminomethyl-2-nitrophenyl)-2-ethoxycarbonylbutanoate To a suspension of 60% sodium hydride (757 mg, 18.9 mmol) in DMF (80 mL) at room temperature was added slowly diethyl malonate (7.6 g, 47.3 mmol). The mixture was stirred for 2 h at 40°~50° C. and a solution of 3-tert-butoxycarbonylaminomethyl-5-nitrostyrene (2.4 g, 8.6 mmol) in DMF (20 mL) was added slowly. The mixture was allowed to warm to room temperature, poured into 2% aqueous potassium hydrogen sulfate (500 mL), and extracted with a 1:1 mixture of toluene and ethyl acetate. The organic layers were washed with brine, dried over magnesium sulfate, and concentrated. The residue was purified by silica gel column chromatography with 8:1 to 3:1 hexane/ethyl acetate to give 3.24 g of the title compound (86%).

$^1$H NMR (CDCl$_3$) δ7.93 (d, 1H, J=8.3 Hz), 7.28 (dd, 1H, J=8.3, 2.0 Hz), 7.26 (d, 1H, J=2.0 Hz), 4.90~5.10 (br, 1H), 4.36 (bd, 2H, J=6.3 Hz), 4.22 (q, 4H, J=6.9 Hz), 3.41 (t, 1H, J=7.3 Hz), 2.94 (t, 2H, J=7.6 Hz), 2.25 (dt, 2H, J=7.3, 7.6 Hz), 1.47 (s, 9H), 1.29 (t, 6H, J=6.9 Hz).

3) 2-(3,3-Diethoxycarbonylpropyl)-4-tert-butoxycarbonylaminomethylaniline

A solution of ethyl 4-(5-tert-butoxycarbonylaminomethyl-2-nitrophenyl)-2-ethoxycarbonylbutanoate (3.2 g, 7.3 mmol) in ethyl acetate (30 mL) was hydrogenated over palladium/charcoal (500 mg) under atmospheric pressure of hydrogen at room temperature for 2.5 h. The mixture was passed through celite and the filtrate was concentrated to give 2.8 g of the title compound (94%).

$^1$H NMR (CDCl$_3$) δ6.96 (dd, 1H, J=7.9, 2.0 Hz), 6.93 (d, 1H, J=2.0 Hz), 6.63 (d, 1H, J=7.9 Hz), 4.58~4.80 (br, 1H), 4.30~4.60 (br, 2H), 4.22 (q, 4H, J=7.3 Hz), 4.16 (bd, 2H, J=5.9 Hz), 3.41 (t, 1H, J=7.3 Hz), 2.53 (dt, 2H, J=7.6 Hz), 2.12 (q, 2H, J=7.3 Hz), 1.45 (s, 9H), 1.28 (t, 6H, J=6.9 Hz).

4) (S)-9-Chloro-5-[p-tert-butoxycarbonylaminomethyl-o-(3,3-diethoxycarbonylpropyl) phenylcarbamoylmethyl]-6,7-dihydro-1H, 5H-pyrido[1,2,3-de]quinoxaline-2,3-dione A procedure similar to that described in Example 18-6) was performed with 2-(3,3-diethoxycarbonylpropyl)-4-tert-butoxycarbonylaminomethylaniline (559 mg, 1.37 mmol) and (S)-9-chloro-5-carboxymethyl-6,7-dihydro-1H, 5H-pyrido[1,2,3-de]quinoxaline-2,3-dione (445 mg, 1.51 mmol) to give 735 mg of the title compound after silica gel column chromatography with 0.3% acetic acid/ethyl acetate (78%).

$^1$H NMR (DMSO-d6) δ11.80~12.30 (br, 1H), 9.41 (bs, 1H), 7.39 (bt, 1H, J=6.3 Hz), 7.25 (d, 1H, J=8.3 Hz), 7.10 (d, 1H, J=2.0 Hz), 7.09 (dd, 1H, J=8.3, 2.0 Hz), 7.07 (d, 1H, J=2.0 Hz), 7.04 (d, 1H, J=2.0 Hz), 5.15~5.28 (m, 1H), 4.13 (q, 4H, J=7.3 Hz), 4.08 (bd, 2H, J=6.3 Hz), 3.47 (t, 1H, J=7.3 Hz), 3.02 (m, 1H), 2.76~2.88 (dm, 1H, J=14.0 Hz), 2.48~2.67 (m, 4H), 2.06~2.18 (dm, 1H, J=14.0 Hz), 1.75~1.98 (m, 3H), 1.40 (s, 9H), 1.18 (t, 6H, H=7.3 Hz).

EXAMPLE 40

(S)-9-Chloro-5-[p-tert-butoxycarbonylaminomethyl-o-(3,3-dicarboxypropyl)phenylcarbamoylmethyl]-6,7-dihydro-1H, 5H-pyrido[1,2,3-de]quinoxaline-2,3-dione A procedure similar to that described in Example 10 was performed with (S)-9-chloro-5-[p-tert-butoxycarbonylaminomethyl-o-(3,3-diethoxycarbonylpropyl) phenylcarbamoylmethyl]-6,7-dihydro-1H, 5H-pyrido[1,2,3-de]quinoxaline-2,3-dione (700 mg, 1.02 mmol) to give the title compound (quant).

EXAMPLE 41

(S)-9-Chloro-5-[p-aminomethyl-o-(3,3-dicarboxypropyl)phenylcarbamoylmethyl]-6,7-dihydro-1H, 5H-pyrido[1,2,3-de]quinoxaline-2,3-dione hydrochloride A procedure similar to that described in Example 11 was performed with (S)-9-chloro-5-[p-tert-butoxycarbonylaminomethyl-o-(3,3-dicarboxypropyl) phenylcarbamoylmethyl]-6,7-dihydro-1H, 5H-pyrido[1,2,3-de]quinoxaline-2,3-dione (1.02 mmol) to give 530 mg of the title compound (96%).

$^1$H NMR (DMSO-d6) δ12.50~13.50 (br, 2H), 12.15 (bs, 1H), 9.56 (bs, 1H), 8.10~8.40 (br, 3H), 7.41 (d, 1H, J=8.3 Hz), 7.33 (d, 1H, J=2.0 Hz), 7.30 (dd, 1H, J=8.3, 2.0 Hz), 7.12 (d, 1H, J=2.0 Hz), 7.08 (d, 1H, J=2.0 Hz), 5.15~5.30 (m, 1H), 3.90~4.02 (m, 2H), 3.29 (t, 1H, J=7.3 Hz), 3.03~3.20 (m, 1H), 2.80~2.90 (dm, 1H, J=14.0 Hz), 2.50~2.70 (m, 4H), 2.03~2.18 (dm, 1H, J=14.0 Hz), 1.78~1.98 (m, 3H).

EXAMPLE 42

(S)-9-Chloro-5-[p-aminomethyl-o-(3-carboxypropyl) phenylcarbamoylmethyl]-6,7-dihydro-1H, 5H-pyrido[1,2,3-de]quinoxaline-2,3-dione hydrochloride A suspension of (S)-9-chloro-5-[p-aminomethyl-o-(3,3-dicarboxypropyl)phenylcarbamoylmethyl]-6,7-dihydro-1H, 5H-pyrido[1,2,3-de]quinoxaline-2,3-dione hydrochloride (550 mg, 0.98 mmol) in acetic acid (300 mL) was refluxed for 5 h. To the mixture was added 0.5N hydrochloric acid and the solvent was removed in vacuo. The residual solid was recrystallized from water to give 450 mg of the title compound (89%).

$^1$H NMR (DMSO-d6) δ11.50~12.50 (br, 1H), 12.17 (bs, 1H), 9.57 (bs, 1H), 8.10~8.50 (br, 3H), 7.42 (d, 1H, J=8.3 Hz), 7.33 (d, 1H, J=2.0 Hz), 7.30 (dd, 1H, J=8.3, 2.0 Hz), 7.12 (d, 1H, J=2.0 Hz), 7.09 (d, 1H, J=2.0 Hz), 5.18~5.30 (m, 1H), 3.97 (bs, 2H), 3.05~3.25 (m, 1H), 2.80~2.91 (dm, 1H, J=14.0 Hz), 2.50~2.80 (m, 4H), 2.27 (t, 2H, J=7.3 Hz), 2.05~2.18 (dm, 1H, J=14.0 Hz), 1.82~1.98 (m, 1H), 1.74 (5et, 2H, J=7.3 Hz).

EXAMPLE 43

(S)-9-Bromo-5-[p-tert-butoxycarbonylaminomethyl-o-(3,3-diethoxycarbonylpropyl) phenylcarbamoylmethyl]-6,7-dihydro-1H, 5H-pyrido[1,2,3-de]quinoxaline-2,3-dione A procedure similar to that described in Example 18-6) was performed with 2-(3,3-diethoxycarbonylpropyl)-4-tert-butoxycarbonylaminomethylaniline (1.5 g, 3.67 mmol) and (S)-9-bromo-5-carboxymethyl-6,7-dihydro-1H, 5H-pyrido[1,2,3-de]quinoxaline-2,3-dione (1.37 g, 4.04 mmol) to give 1.60 g of the title compound after silica gel column chromatography with 0.3% acetic acid/ethyl acetate (60%).

$^1$H NMR (DMSO-d6) δ11.00~13.00 (br, 1H), 9.41 (bs, 1H), 7.39 (bt, 1H, J=6.3 Hz), 7.25 (d, 1H, J=8.3 Hz), 7.19 (d, 1H, J=2.0 Hz), 7.16 (d, 1H, J=2.0 Hz), 7.07 (d, 1H, J=2.0 Hz), 7.06 (dd, 1H, J=8.3, 2.0 Hz), 5.18~5.30 (m, 1H), 4.13 (q, 4H, J=7.3 Hz), 4.08 (bd, 2H, J=5.6 Hz), 3.47 (t, 1H, J=7.6 Hz), 3.02~3.20 (m, 1H), 2.78~2.90 (dm, 1H, J=14.0 Hz), 2.50~2.70 (m, 4H), 2.07~2.18 (dm, 1H, J=14.0 Hz), 1.80~2.00 (m, 3H), 1.40 (s, 9H), 1.18 (t, 6H, J=7.3 Hz).

EXAMPLE 44

(S)-9-Bromo-5-[p-tert-butoxycarbonylaminomethyl-o-(3,3-dicarboxypropyl)phenylcarbamoylmethyl]-6,7-dihydro-1H, 5H-pyrido[1,2,3-de]quinoxaline-2,3-dione A procedure similar to that described in Example 10 was performed with (S)-9-bromo-5-[p-tertbutoxycarbonylaminomethyl-o-(3,3-diethoxycarbonylpropyl) phenylcarbamoylmethyl]-6,7-dihydro-1H, 5H-pyrido[1,2,3-de]quinoxaline-2,3-dione (1.50 g, 2.06 mmol) to give the title compound (quant).

EXAMPLE 45

(S)-9-Bromo-5-[p-aminomethyl-o-(3,3-dicarboxypropyl)phenylcarbamoylmethyl]-6,7-dihydro-1H, 5H-pyrido[1,2,3-de]quinoxaline-2,3-dione hydrochloride A procedure similar to that described in Example 11 was performed with (S)-9-bromo-5-[p-tert-butoxycarbonylaminomethyl-o-(3,3-dicarboxypropyl) phenylcarbamoylmethyl]-6,7-dihydro-1H, 5H-pyrido[1,2,3-de]quinoxaline-2,3-dione (2.06 mmol) to give 1.45 g of the title compound (quant).

$^1$H NMR (DMSO-d6) δ11.00~13.00 (br, 2H), 12.14 (bs, 1H), 9.55 (bs, 1H), 8.15~8.40 (br, 3H), 7.40 (d, 1H, J=7.9 Hz), 7.33 (d, 1H, J=2.0 Hz), 7.30 (dd, 1H, J=7.9, 2.0 Hz), 7.24 (d, 1H, J=2.0 Hz), 7.20 (d, 1H, J=2.0 Hz), 5.18~5.30 (m, 1H), 3.98 (m, 2H), 3.29 (t, 1H, J=7.3 Hz), 3.04~3.21 (m, 1H), 2.80~2.91 (dm, 1H, J=14.0 Hz), 2.50~2.70 (m, 4H), 2.05~2.18 (dm, 1H, J=14.0 Hz), 1.75~2.00 (m, 3H).

What is claimed is:

1. A tricyclic quinoxalinedione derivative represented by the formula 1:

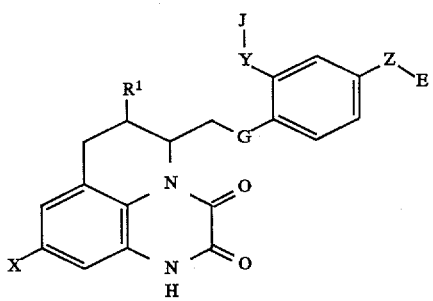

wherein X represents hydrogen, alkyl, halogen, cyano, trifluoromethyl, or nitro;

$R^1$ represents hydrogen, alkyl, cycloalkyl, or cycloalkylalkyl;

G represents —CONR$^2$— or —NR$^2$CO—, wherein $R^2$ represents hydrogen or alkyl;

J represents carboxyl, tetrazolyl, —COOR$^{3J}$, —CONH$_2$, —CON(OH)H, —CONHR$^{3J}$, —CON(OH)R$^{3J}$, —CON(OR$^{5J}$)R$^{3J}$ or —CONR$^{3J}$R$^{4J}$, wherein R$^{3J}$ and R$^{4J}$ independently represent alkyl, cycloalkyl, alkenyl, arylalkyl, arylalkyl substituted by 1 to 3 substituents selected from the group consisting of alkyl, halogen, trifluoromethyl and alkoxy, or cycloalkylalkyl, or R$^{3J}$ and R$^{4J}$ are joined to form an alkylene and are joined together with N to which they are attached to form a 3- to 7-membered cyclic amine that does not contain an additional hetero atom, a piperazine, an N-methyl piperazine or a morpholine, and R$^{5J}$ represents alkyl;

E represents —NH$_2$, —NHR$^{3E}$, —NR$^{3E}$R$^{4E}$, —NH—C(=NH)—NH$_2$, —NH—C(=NH)—NHR$^{3E}$, —NH—C(=NH)—NR$^{3E}$R$^{4E}$, —NHL, —NLR$^{3E}$, —NH—C(=NL)—NH$_2$, —NHC(=NH)—NHR$^{3E}$ or —NH—C—(=NL)R$^{3E}$R$^{4E}$, wherein R$^{3E}$ and R$^{4E}$ independently represent alkyl, cycloalkyl, alkenyl or cycloalkylalkyl, or R$^{3E}$ and R$^{4E}$ are joined to form an alkylene and are joined together with N to which they are attached to form a 3- to 7-membered cyclic amine that does not contain an additional hetero atom, a piperazine, an N-methyl piperazine or a morpholine, and L represents alkanoyl or alkoxycarbonyl;

Y represents a single bond, alkylene, alkenylene, alkylene substituted by a substituent selected from the group consisting of hydroxy, —OR$^{3S}$, —OCOR$^{3S}$, amino, —NHCOR$^{3S}$, —NHCO$_2$R$^{3S}$, carboxyl and —CO$_2$R$^{3S}$, wherein R$^{3S}$ represents alkyl, cycloalkyl, alkenyl or cycloalkylalkyl, or Y represents Y$^1$—Q—Y$^2$, wherein Y$^1$ represents a single bond or alkylene, Y$^2$ represents alkylene, and Q represents a heteroatom selected from oxygen or sulfur; and Z represents alkylene;

wherein the term "alkyl" means an alkyl group containing from 1 to 6 carbon atoms; the term "halogen" means fluorine, chlorine, bromine or iodine; the term "cycloalkyl" means a cycloalkyl group containing from 3 to 7 carbon atoms; the term "cycloalkylalkyl" means a straight-chain or branched-chain alkyl to which a cycloalkyl group is attached, which contains up to 13 carbon atoms; the term "alkylene" means an alkylene group containing from 1 to 6 carbon atoms; the term "alkenylene" means an alkenylene group containing from 2 to 6 carbon atoms; and the term "alkenyl" means an alkenyl group containing from 3 to 6 carbon atoms, of which an olefinic carbon atom may not be connected directly with a nitrogen atom or an oxygen atom, or a pharmaceutically acceptable salt thereof.

2. A compound according to claim 1, wherein X is halogen.

3. A compound according to claim 2, wherein G is —CONR$^2$—.

4. A compound according to claim 3, wherein R$^2$ is hydrogen.

5. A compound according to claim 4, wherein R$^1$ is hydrogen.

6. A compound according to claim 5, wherein Z is methylene.

7. A compound according to claim 6, wherein E is selected from the group consisting of —NH$_2$ and —NHC(=NH)NH$_2$.

8. A compound according to claim 7, wherein J is selected from the group consisting of —COOH and —COOR$^{3J}$ wherein R$^{3J}$ represents alkyl, cycloalkyl, alkenyl, cycloalkylalkyl, arylalkyl, or arylalkyl substituted by up to three substituents selected from the group consisting of alkyl, halogen, trifluoromethyl and alkoxy;

wherein the term "alkyl" means an alkyl group containing from 1 to 6 carbon atoms; the term "halogen" means fluorine, chlorine, bromine or iodine; the term "cycloalkyl" means a cycloalkyl group containing from 3 to 7 carbon atoms; the term "alkenyl" means an alkenyl group containing from 3 to 6 carbon atoms, of which an olefinic carbon atom may not be connected directly with a nitrogen atom or an oxygen atom; the term "cycloalkylalkyl" means an alkyl group attached with a cycloalkyl group, which contains up to 13 carbon atoms; the term "arylalkyl" means an alkyl group attached with an aryl group, which contains up to 15 carbon atoms; and the term "alkoxy" means an alkoxy group containing from 1 to 6 carbon atoms.

9. A compound according to claim 8, wherein Y is selected from the group consisting of a single bond, methylene, dimethylene, trimethylene, and —OCH$_2$—.

10. A pharmaceutical composition comprising a pharmaceutically effective amount of a compound of claim 1 or a pharmaceutically acceptable salt thereof, and a pharmaceutically acceptable carrier or diluent therefor.

11. A method for treating central nervous system damage in a patient which is induced by an ischaemic or a hypoxic condition, which comprises administering a pharmaceutically effective amount of a compound of claim 1 or a pharmaceutically acceptable salt thereof to said patient.

12. A compound represented by the formula:

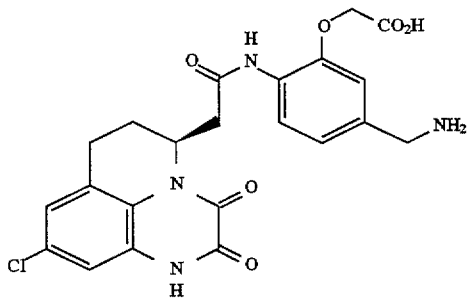

or a pharmaceutically acceptable salt thereof.

13. A method for producing an analgesic, antidepressant, anxiolitic, or antischizophrenic effect in a patient, which comprises administering a pharmaceutically effective amount of a compound of claim 1 or a pharmaceutically acceptable salt thereof to said patient.

14. A method for treating epilepsy or stroke in a patient suffering therefrom, which comprises:

administering a pharmaceutically effective amount of a compound of claim 1 or a pharmaceutically acceptable salt thereof to said patient.

15. A compound according to claim 1, wherein the 3- to 7-membered cyclic amine formed by the groups $R^{3J}$ and $R^{4J}$, or $R^{3E}$ and $R^{4E}$ is a member selected from the group consisting of an azetidine, a pyrrolidine, a piperidine and a piperazine.

16. A compound according to claim 1, wherein X is alkyl, halogen, cyano, trifluoromethyl or nitro, G is a group of the formula: —$CONR^2$—.

* * * * *